(12) United States Patent
John et al.

(10) Patent No.: US 11,478,576 B2
(45) Date of Patent: Oct. 25, 2022

(54) SYSTEMS AND METHODS FOR INDICATING AN AMOUNT OF A FEEDING FLUID THAT IS DISPENSED TO AN INDIVIDUAL

(71) Applicant: Avira Health Incorporated, San Diego, CA (US)

(72) Inventors: Tina John, San Diego, CA (US); Brian Bowman, Carlsbad, CA (US); Clayton Alderson, Solana Beach, CA (US); Aidan J. Fay, La Jolla, CA (US); Henry Warder, San Francisco, CA (US); Conner Magnuson, San Diego, CA (US); Brandon Duquesnel, Temecula, CA (US); Benjamin Arnold, San Diego, CA (US); Ian Fried, San Diego, CA (US)

(73) Assignee: Avira Health Incorporated, San Diego, CA (US)

( * ) Notice: Subject to any disclaimer, the term of this patent is extended or adjusted under 35 U.S.C. 154(b) by 0 days.

(21) Appl. No.: 17/554,746

(22) Filed: Dec. 17, 2021

(65) Prior Publication Data

US 2022/0193313 A1 Jun. 23, 2022

Related U.S. Application Data

(60) Provisional application No. 63/243,908, filed on Sep. 14, 2021, provisional application No. 63/127,085, filed on Dec. 17, 2020.

(51) Int. Cl.
*A61M 1/06* (2006.01)
*F04B 13/00* (2006.01)
(Continued)

(52) U.S. Cl.
CPC ............. *A61M 1/068* (2014.02); *F04B 13/00* (2013.01); *F04B 43/12* (2013.01); *G16H 20/60* (2018.01);
(Continued)

(58) Field of Classification Search
CPC .......... A61M 1/068; A61M 2205/3313; A61M 2205/3317; A61M 2205/3327;
(Continued)

(56) References Cited

U.S. PATENT DOCUMENTS

| 4,265,370 A | 5/1981 | Reilly |
| 9,636,280 B1 | 5/2017 | Althallab |

(Continued)

FOREIGN PATENT DOCUMENTS

| DE | 102011118246 B3 | 5/2013 |
| EP | 2388026 A1 | 11/2011 |
| WO | 2020181544 A1 | 3/2019 |

OTHER PUBLICATIONS

International Search Report and Written Opinion from PCT App. No PCT/US2021/064128 dated Apr. 18, 2022, 12 pages.

*Primary Examiner* — Amber R Stiles
(74) *Attorney, Agent, or Firm* — Acuity IP, LLC; Nathan S. Cassell

(57) ABSTRACT

Methods and breast pump devices for simultaneous pumping and feeding breastmilk in the nursing position and quantification of breastmilk consumption are provided. A breast pump device includes a nipple shield for receiving a nipple, a housing having a throughput aperture and a fluid path, the fluid path extending from the nipple shield to the throughput aperture, and a negative pressure source. In some embodiments, the housing further includes a gate to control the quantity of breastmilk displaced to a baby. In some embodiments, the gate operates to respond to the amount of
(Continued)

breastmilk displaced to the baby, and thereby allows for quantification. In some embodiments, the quantity of breastmilk displaced is also recorded.

26 Claims, 71 Drawing Sheets

(51) Int. Cl.
*F04B 43/12* (2006.01)
*G16H 20/60* (2018.01)
*G16H 40/63* (2018.01)

(52) U.S. Cl.
CPC ..... *G16H 40/63* (2018.01); *A61M 2205/3313* (2013.01); *A61M 2205/3317* (2013.01); *A61M 2205/3327* (2013.01); *A61M 2205/3382* (2013.01); *A61M 2205/3386* (2013.01); *A61M 2205/502* (2013.01)

(58) Field of Classification Search
CPC .. A61M 2205/3382; A61M 2205/3386; A61M 2205/502; F04B 13/00; F04B 43/12; G16H 20/60; G16H 40/63; A61J 15/0076; A61J 15/008; A61J 15/0088
See application file for complete search history.

(56) References Cited

U.S. PATENT DOCUMENTS

| | | | |
|---|---|---|---|
| 10,632,238 | B1 | 4/2020 | Hodges et al. |
| 2014/0242213 | A1* | 8/2014 | McCarty ................ A23L 33/30 222/146.2 |
| 2015/0038945 | A1 | 2/2015 | McCabe |
| 2016/0158437 | A1 | 6/2016 | Biasi et al. |
| 2017/0340147 | A1 | 11/2017 | Hambrock et al. |
| 2018/0055978 | A1 | 3/2018 | Ong |
| 2020/0345907 | A1 | 11/2020 | Makower et al. |
| 2021/0001024 | A1 | 1/2021 | Thuring et al. |

\* cited by examiner

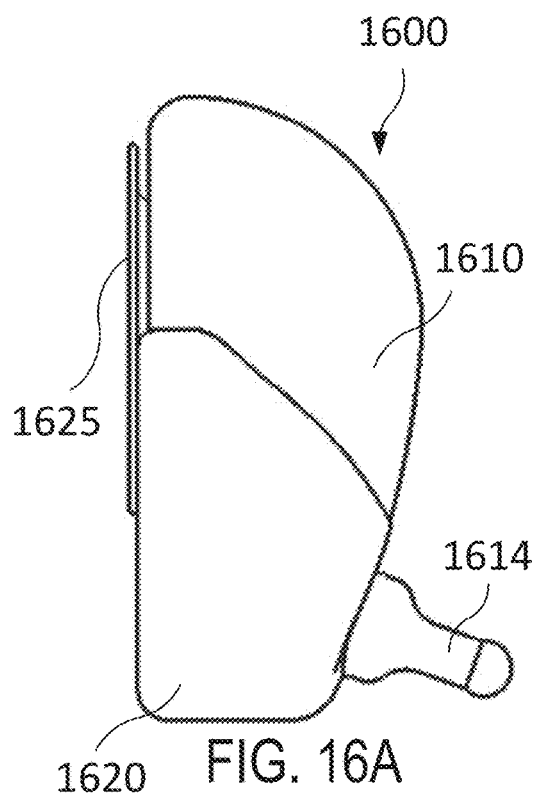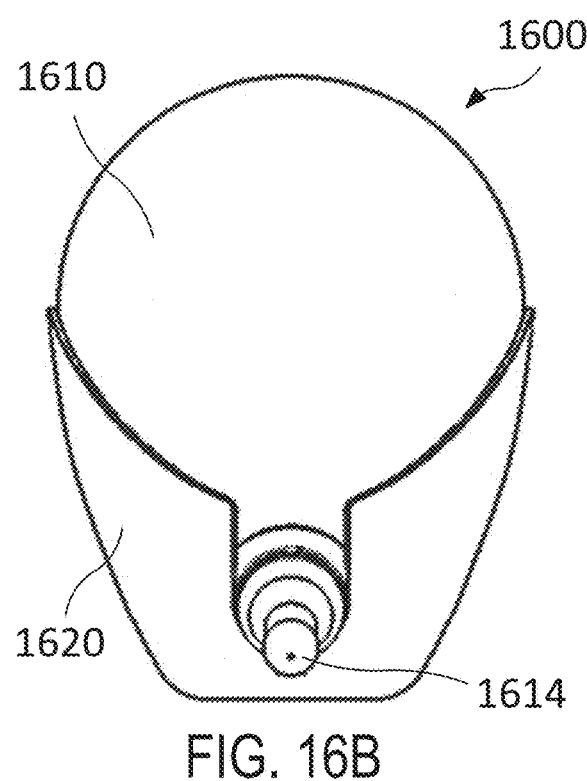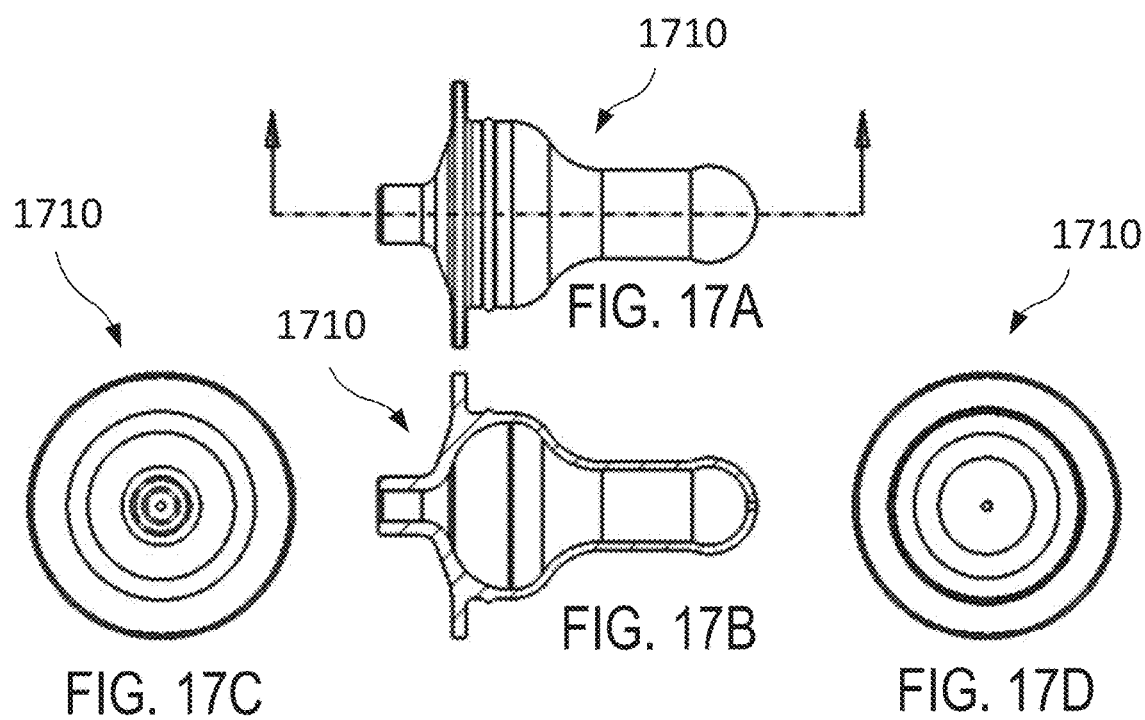

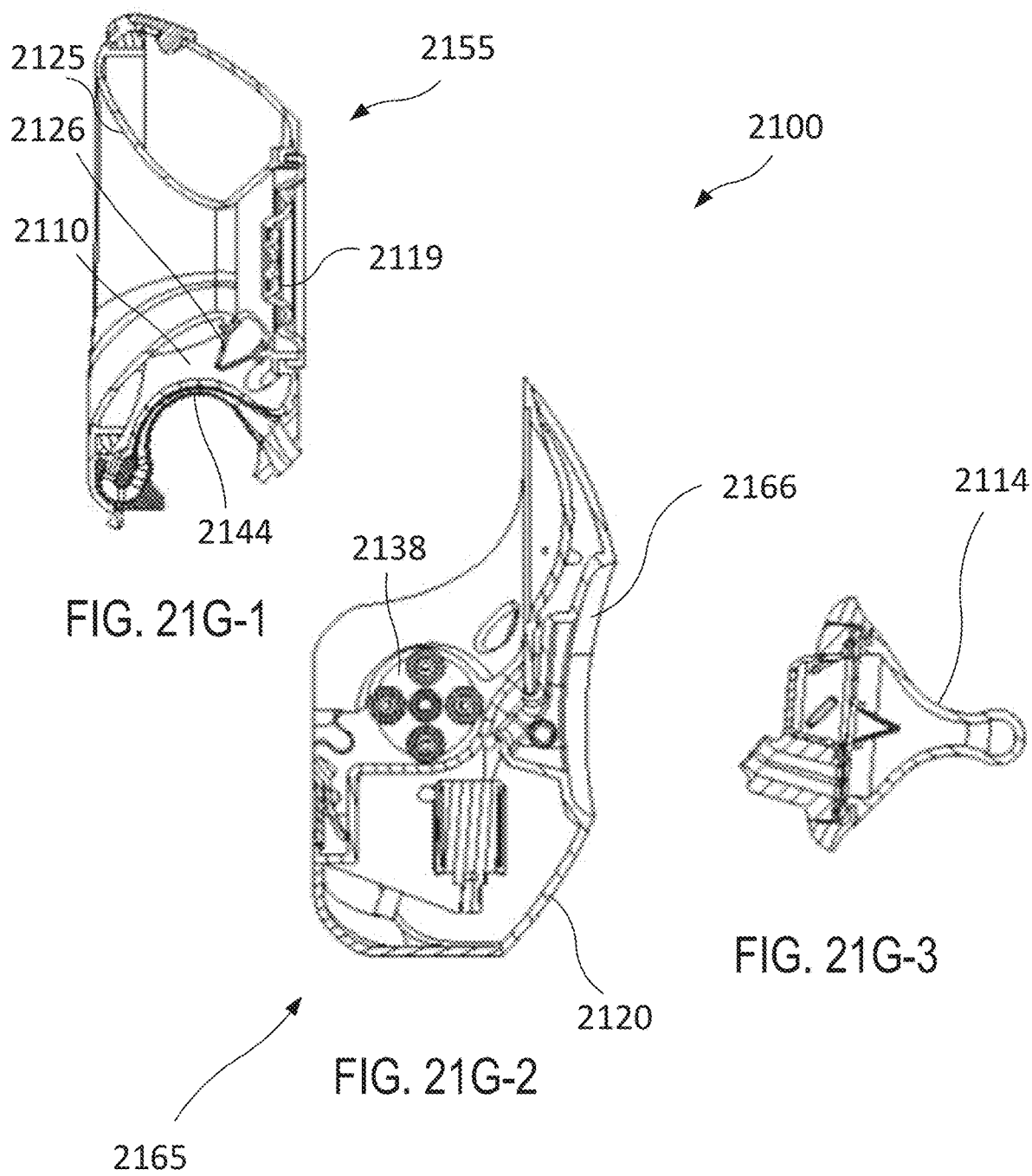

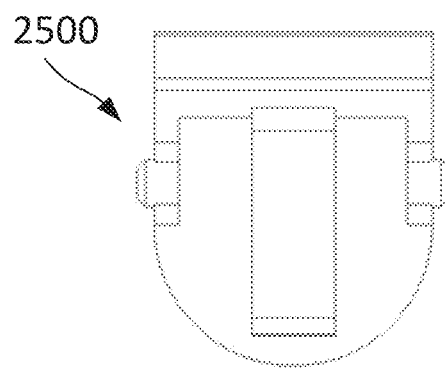
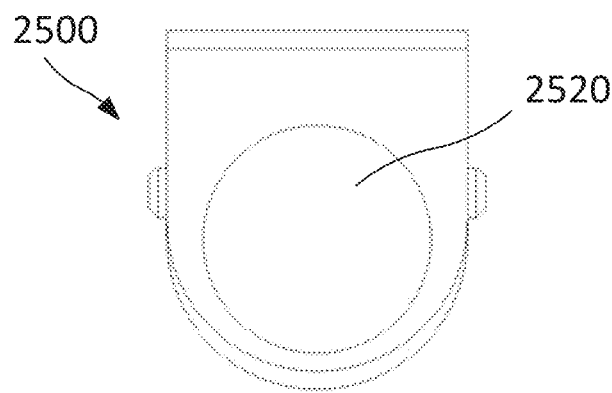
FIG. 25A
FIG. 25B
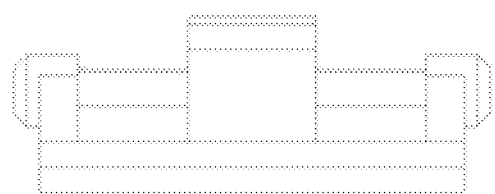
FIG. 25C
FIG. 25D
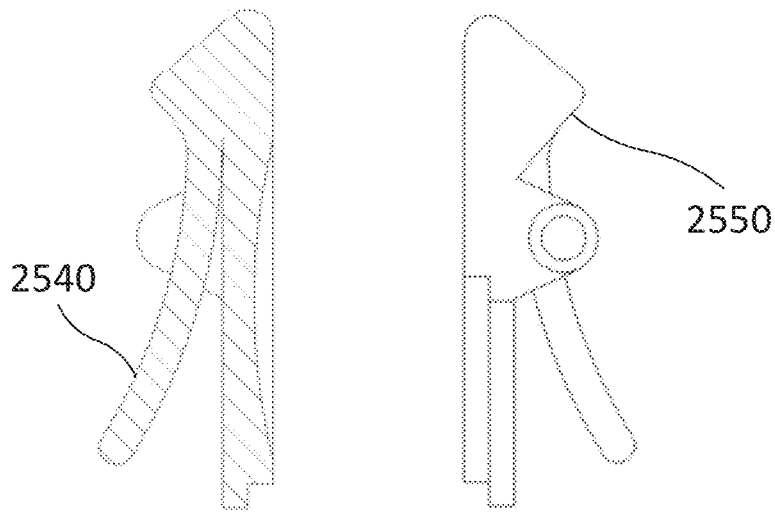
FIG. 25E
FIG. 25F

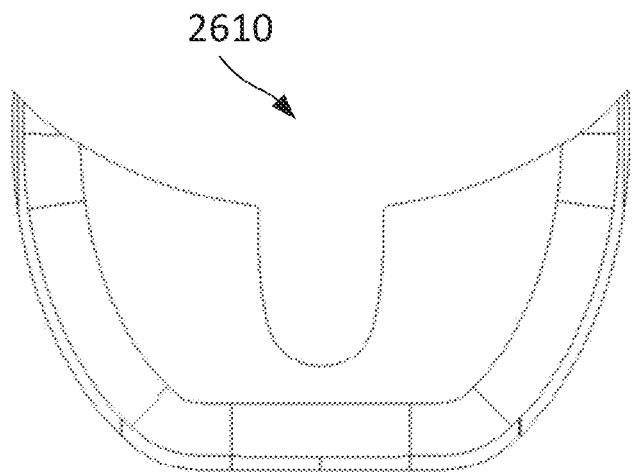
FIG. 26A
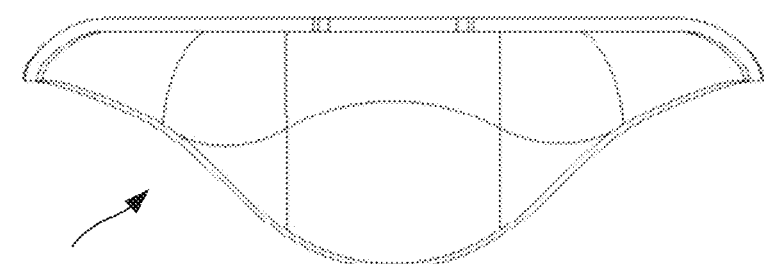
FIG. 26B
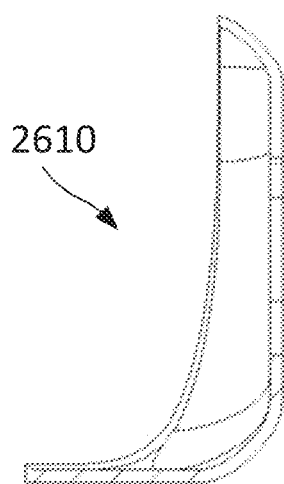 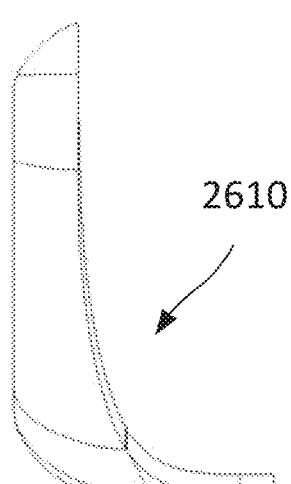
FIG. 26C   FIG. 26D

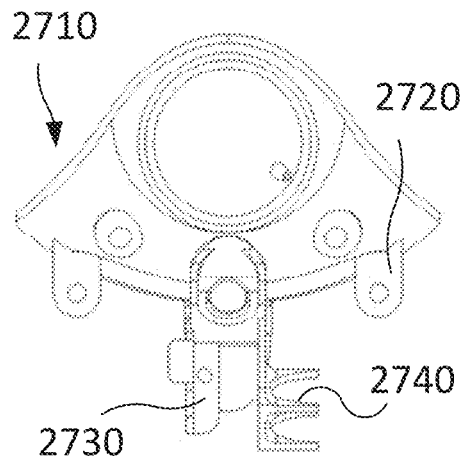
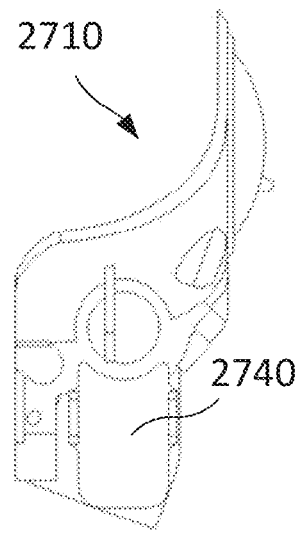
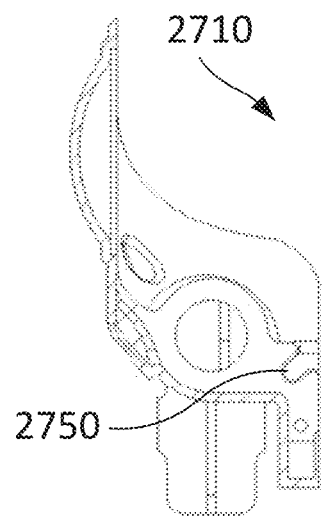
FIG. 27A  FIG. 27B  FIG. 27C
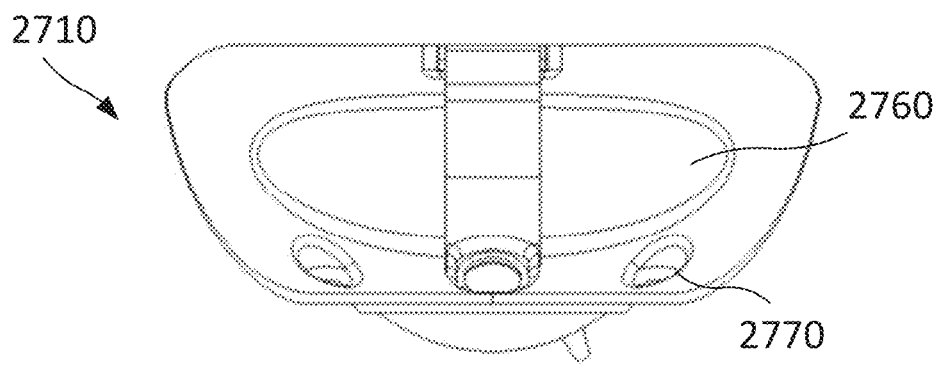
FIG. 27D
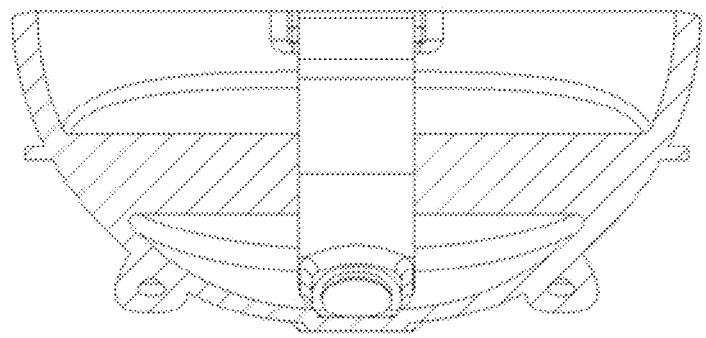
FIG. 27E

SYSTEMS AND METHODS FOR INDICATING AN AMOUNT OF A FEEDING FLUID THAT IS DISPENSED TO AN INDIVIDUAL

CROSS-REFERENCE TO RELATED APPLICATIONS

This application claims the benefit of U.S. Provisional Patent Application Nos. 63/127,085 filed Dec. 17, 2020 and 63/243,908 filed Sep. 14, 2021, the disclosures of which are incorporated herein by reference.

BACKGROUND OF THE INVENTION

Breastfeeding in the first six months of life is highly beneficial to achieving optimal growth, development, and health of the child, and additionally provides numerous benefits to the mother; however, the majority of mothers report having problems breastfeeding within a few days of giving birth. Many mothers report problems establishing or understanding whether the infant is successful in latching to the breast. In addition, many mothers report problems with pain, such as chapped, sore, and bleeding nipples. Further, many mothers experience anxiety around whether the baby is consuming the right amount of breastmilk or whether enough breastmilk is being produced. As a result, despite having every intention to breastfeed, many mothers cease breastfeeding.

Breast pumps provide a solution to breastfeeding difficulties by mechanically extracting breastmilk which can later be fed to the baby. The breast pumping process, however, is tremendously time consuming and hinders the mother's ability to tend to and bond with a newborn.

SUMMARY OF THE INVENTION

The present disclosure generally relates to breast pumps and quantification methods and more particularly relates to breast pumps and consumption quantification methods that allow for simultaneous breastmilk pumping and feeding and quantification of breastmilk consumption in a single nursing session.

Breastfeeding in the first six months of life is highly beneficial to achieving optimal growth, development, and health; however, the majority of mothers report having problems breastfeeding within a few days of giving birth. While breast pumps allow for mothers to pump breastmilk that can be later consumed by a baby from a bottle with volume markings, breast pumps that are currently available fail to allow a mother to simultaneously pump and feed expressed breastmilk to a baby in a nursing position.

As such, it would be beneficial to provide a device that allows for simultaneous pumping and feeding breastmilk in the nursing position, even during obstacles like difficulty forming a proper latch to the breast, occurrence of painful sore or cracked nipples, and concerns of whether appropriate supply of breastmilk is in place. Providing this alternative method of feeding breastmilk is especially important in the early days postpartum when the mother infant dyad is establishing the combined routine and rhythm of breastfeeding, also a time when the dropout rate of breastfeeding among mothers wishing to breastfeed is highest. Further, this device may be of particular benefit to preterm infants who are immunocompromised or incapable of proper sucking or latching until further growth. Simultaneously pumping and feeding through the same device allows the mother to tend to the baby during pumping by being able to feed or hold the infant, as in natural nursing. The proximity of the baby when the baby is drinking from the device at the breast also allows for continued bonding and mimics the gait of nursing, which builds familiarity for the mother and baby for switching to or practicing nursing at the breast. Further, as breastmilk is produced by positive feedback to the amount of milk removed from the breast (not by the amount of suckling), simultaneous pumping and feeding promotes the removal of milk from the breast in quantities mediated by the infant's need, and thereby correctly regulating the production of future milk at the breast. In contrast, feeding formula without pumping per the infant's need would falsely indicate a decreased need of milk production to the breast. Research indicates that the milk removed from the breast in the first weeks postpartum are particularly indicative of the number of milk receptor sites created in the breast, which impacts the maximum quantity of milk production for months to follow. For this reason, promoting ease of removal of milk from the breast during this window and feeding to the infant sets the stage for optimal breastmilk production. The ability to feed breastmilk to the infant during pumping also saves time by allowing the mother to feed the baby without first manually transferring pumped or stored breastmilk to a bottle for consumption at a time separate to the breast pumping process. Accordingly, devices that both pump breastmilk and simultaneously make pumped breastmilk available for the baby to consume from a nipple attachment are provided to address this need.

Embodiments of the present invention encompass breastmilk pumping and feeding systems and methods which provide for the dispensing and sensing of controlled measured amounts of breastmilk. Advantageously, such systems and methods are well suited for use with infants that need intensive medical care, for example infants that are admitted to a neonatal intensive care unit (NICU). According to some embodiments, systems and methods are used to provide NICU infants with dosed milk. With infants monitored in the NICU, it is important to know how much breastmilk or formula the infant receives by oral feeding, to manage weight gain. The NICU infant stands to gain significantly from quantified and facilitated pumping and feeding of breastmilk, as each drop of breastmilk provides much needed defense for ailments that can lead to serious complications, such as GI respiratory infections that lead to surgical intervention. As an example, the American Academy of Pediatrics cites that providing human milk during the length of the NICU stay lowers the risk of Necrotizing Enterocolitis by 77%. For this reason, NICU mothers are often the most encouraged and motivated to exclusively pump (exclusive pumping refers to providing entire nourishment via breastmilk by pumping at 2 to 3-hour intervals throughout the day and night). With devices that quantify the amount of pumped breastmilk is dispensed to or consumed by the infant through the device, the mother and healthcare team can continue to track the amounts received without switching to a bottle or reading volume markings and calculating and recording feeding amounts manually. Further, the side-lying or pace-feeding position which infants would assume to drink from the mother's pumped reservoir, much like facing the breast during cradle or cross cradle hold, promotes safe swallowing for pre-term infants. The side lying position allows milk to pool in the infant's cheek, from which the infant can swallow when ready. In a gestational age where the suck-swallow-breathe system may not be established, this prevents the infant from unwillingly swallowing or choking on milk in the reclined position often used on older infants.

In one aspect of the invention, the device may both pump and feed the baby from the same apparatus at the same time. The device may utilize negative pressure to cause milk expression from a breast. The device may comprise a housing that comprises a nipple shield and a negative pressure source. The housing may further comprise a fluid path from the breast nipple shield to a baby nipple attachment. The housing may be sized and the nipple attachment may be oriented to allow a baby to consume milk from the nipple attachment in the nursing position.

In another aspect of the invention, the device comprises a storage container to receive excess breastmilk not consumed by the baby during a feeding session. The breastmilk storage container may comprise a standard thread for engagement with a nipple attachment to allow for later consumption. Alternatively, the breastmilk storage container may comprise an opening through which breastmilk may be transferred into a bottle or breastmilk storage bag to allow for later consumption. Due to separation of the breastmilk exposed to the infant's saliva from milk stored by the presence of one-way valves or gating mechanisms, maximum safe storage time can be achieved for stored milk, despite simultaneous infant drinking. Storage of milk while infant nutritional demands are simultaneously met also allow the mother to better control and create the supply of milk that will be used for future nutrition, when away from baby or ceasing breastfeeding at the breast.

Further, if a device is used to simultaneously pump and feed a baby from a first breast, then a second device may be used to pump breastmilk from a second breast into a breastmilk storage container for later consumption.

It would also be beneficial to quantify the breastmilk consumed by the baby and transmit and record the consumption data for caregivers and healthcare providers. The live quantification of breastmilk consumed by the baby allows the mother to know whether and how much breastmilk the baby is receiving during a given nursing session and gestational age. It also allows for documentation of breastmilk displaced to a baby during each feeding session and easy sharing of such data with a medical provider. This quantification of milk dispensed to the baby promotes confidence in the mother that the baby received sufficient nutrition. Accordingly, devices that both pump breastmilk and simultaneously make pumped breastmilk available for the baby to consume from a nipple attachment and quantify breastmilk consumption are provided to address this need.

In one aspect of the invention, the device comprises infrared sensors configured to quantify breastmilk displaced to the baby. The breastmilk consumed by the baby may be quantified by a series of incorporated sensors that indicate whether a preliminary breastmilk receptacle or dosing tube of defined volume is full or empty. The sensors may trigger a gate to allow more breastmilk to fill into the receptacle or dosing tube when empty and gate off breastmilk when full. A count of how many times the defined volume is filled may provide the live quantification of breastmilk consumption. The defined volume may range from about 0.1 mL to about 15 mL. Additionally, the infrared sensor may transmit the quantification data via Bluetooth connection to a personal device for viewing by a caregiver or healthcare provider during the nursing session or on a later date. Embodiments of the present invention also encompass systems and methods involving a device having a flexible compartment that collapses with suction from the infant and a peristaltic pump to refill the flexible compartment, that drives quantification of the breastmilk displaced to baby. The collapse of the flexible compartment, which contains a small magnet, is sensed by a hall effect sensor, at which point a bolus of milk is pushed forward into the flexible compartment by a peristaltic motor. The number of rotations of the peristaltic motor and the inner diameter of the tube being acted on by peristalsis determine the amount of milk dispensed to the infant.

In another aspect of the invention, the device may embody the source of negative pressure or may be compatible with market negative pressure devices. According to some embodiments, systems and methods may involve the use of a device for the addition of needed supplements, medicines, or alternate nutrition like formula, wholly or additionally to breastmilk being pumped. This could be used to quantify food or other liquids while still in the position of nursing, to fortify breastmilk with other components such as formula or vitamins, or to add medicines to be consumed solely or along with the other contents of the device. According to some embodiments, systems and methods may involve the use of a device by any individual other than the mother (or individual producing the breastmilk), such as the father or alternate caregiver. The other individual could dispense fluid to the baby and be able to assume the familiar nursing position and receive benefits of the bonding associated, and/or also receive the amount quantified that can be recorded or shared through an application or other software for installation and execution on a computer, tablet, smartphone or other electronic device.

In still another aspect, embodiments of the present invention encompass systems for indicating an amount of a feeding fluid that is dispensed to an individual. Exemplary systems can include a chamber that stores feeding fluid, a dosing mechanism that receives feeding fluid from the chamber and that dispenses discrete packets of feeding fluid, where each discrete packet has a discrete packet volume, a feeding apparatus that receives feeding fluid dispensed by the dosing mechanism and that allows feeding fluid to flow to the individual's mouth through an outlet of the feeding apparatus, a sensor assembly that determines when the feeding apparatus is available to receive a new discrete packet of feeding fluid dispensed from the dosing mechanism, and a counting mechanism that registers a count for each dispensing event performed by the dosing mechanism. In some cases, systems can include a processor that determines the amount of feeding fluid that is dispensed to the individual based on the discrete packet volume and the number of registered counts. In some cases, the dosing mechanism includes a peristaltic pump. In some cases, the sensor assembly includes a hall effect sensor. In some cases, the system further includes a collapsible chamber that receives the discrete packets of feeding fluid dispensed by dosing mechanism and that allows the discrete packets of feeding fluid to flow toward the outlet of the feeding apparatus. In some cases, the system further includes a magnet in operative association with the collapsible chamber. In some cases, the sensor assembly determines that the peristaltic pump should dispense the new discrete packet of feeding fluid when the magnet reaches a first distance away from the hall effect sensor and that the peristaltic pump should pause when the magnet reaches a second distance away from the hall effect sensor, the first distance being greater than the second distance. In some cases, the dosing mechanism includes a gate and a tube, the sensor assembly includes a full sensor and an empty sensor, the gate allows passage of feeding fluid through the tube when the empty sensor indicates the tube is empty of feeding fluid, and the gate prevents passage of feeding fluid through the tube when the full sensor indicates the tube is full of feeding fluid. In some cases, the dosing mechanism includes a first compressible chamber and a second compressible chamber, and the first and second compressible chambers alternate with filling and dispensing of feeding fluid. In some cases, the feeding apparatus includes a first compressible chamber and a second compressible chamber, and the first and second compressible chambers alternate with filling and dispensing of feeding fluid. In some cases, the system includes a first compressible chamber and a second compressible chamber, and the first and second compressible chambers alternate with filling and dispensing of feeding fluid. In some cases, a system can further include a sensor such as a capacitance sensor or an infrared sensor, the sensor is configured to detect a feeding fluid amount present in the chamber. In some cases, the system is configured to signal additional feeding fluid to enter the chamber based on the detected feeding fluid amount.

In another aspect, embodiments of the present invention encompass mobile computing devices configured to display operational information for a feeding fluid system. Exemplary mobile computing devices can include a screen, a processor, an electronic storage location operatively associated with the processor, and processor executable code stored on the electronic storage location and embodied in a tangible non-transitory computer readable medium. The processor executable code, when executed by the processor, can cause the processor to generate a graphical user interface on the screen, the graphical user interface having a representation of feeding fluid dispensed orally to an individual from the feeding fluid system. The representation can be based on a count registered by a counting mechanism of the feeding fluid system, where each count corresponds to a discrete packet of feeding fluid dispensed by a dosing mechanism of the feeding fluid system. In some cases, the representation includes an amount of feeding fluid dispensed to the individual from the feeding fluid system during one feeding session. In some cases, the representation includes an amount of feeding fluid dispensed to the individual from the feeding fluid system during multiple feeding sessions. In some cases, the representation includes a time indicator for a feeding session.

In another aspect, embodiments of the present invention encompass methods for indicating an amount of a feeding fluid that is dispensed to an individual. Exemplary methods can include storing feeding fluid in a chamber, receiving feeding fluid from the chamber at a dosing mechanism, and dispensing discrete packets of feeding fluid, each discrete packet having a discrete packet volume, from the dosing mechanism toward a feeding apparatus. The feeding apparatus can make the feeding fluid available for oral consumption by an individual. Methods can also include determining, with a sensor assembly, when the feeding apparatus is available to receive a new discrete packet of feeding fluid dispensed from the dosing mechanism. Methods can further include registering, with a counting mechanism, a count for each dispensing event performed by the dosing mechanism. In some cases, methods can include determining, with a processor, the amount of feeding fluid that is dispensed to the individual based on the discrete packet volume and the number of registered counts. In some cases, the dosing mechanism can include a peristaltic pump. In some cases, the sensor assembly can include a hall effect sensor. In some cases, methods can further include receiving, at a collapsible chamber, the discrete packets of feeding fluid dispensed by dosing mechanism, and transmitting, from the collapsible chamber, the discrete packets of feeding fluid toward the feeding apparatus. In some cases, the collapsible chamber is coupled with a magnet, and the sensor assembly determines that the peristaltic pump should dispense the new discrete packet of feeding fluid when the magnet reaches a first distance away from the hall effect sensor and that the peristaltic pump should pause when the magnet reaches a second distance away from the hall effect sensor, the first distance being greater than the second distance. In some instances, the dosing mechanism includes a gate and a tube, the sensor assembly includes a full sensor and an empty sensor, and methods further include allowing, with the gate, passage of feeding fluid through the tube when the empty sensor indicates the tube is empty of feeding fluid, and preventing, with the gate, passage of feeding fluid through the tube when the full sensor indicates the tube is full of feeding fluid. In some instances, the dosing mechanism includes a first compressible chamber and a second compressible chamber, and methods further include alternating filling and dispensing of feeding fluid by the first and second compressible chambers. In some instances, the feeding apparatus includes a first compressible chamber and a second compressible chamber, and methods further include alternating filling and dispensing of feeding fluid by the first and second compressible chambers. In some instances, a system includes a first compressible chamber and a second compressible chamber, and methods further include alternating filling and dispensing of feeding fluid by the first and second compressible chambers. In some instances, methods can further include detecting, with a capacitance sensor, a feeding fluid amount present in the chamber, and signaling the entrance of additional feeding fluid into the chamber based on the detected feeding fluid amount. In some instances, methods can further include detecting, with an infrared sensor, a feeding fluid amount present in the chamber, and signaling the entrance of additional feeding fluid into the chamber based on the detected feeding fluid amount. In some instances, methods can further include displaying, on a graphical user interface of a screen of a mobile computing device, a representation of the amount of feeding fluid that is consumed by the infant. In some instances, the representation can include the amount of feeding fluid consumed by the infant during one feeding session. In some instances, the representation can include the amount of feeding fluid consumed by the infant during multiple feeding sessions.

In yet another aspect, embodiments of the present invention encompass breast pump systems and methods for simultaneous breastmilk pumping and feeding. Exemplary breast pumps can include a breast flange for receiving a nipple, a housing having a throughput aperture and a fluid path, the fluid path extending from the breast flange to the throughput aperture, and a negative pressure source. In some cases, the housing further includes the negative pressure source. In some cases, the negative pressure source is external to the housing. In some cases, the breast pump further includes a nipple attachment. In some cases, the housing further includes a nipple attachment indent to receive the nipple attachment. In some cases, a breast pump further includes a first backflow valve adjacent to the negative pressure source and the nipple shield. In some cases, the breast pump further includes a second backflow valve adjacent to the nipple shield and the priming chamber. In some cases, the breast pump further includes a third backflow valve adjacent to the dosing tube and the nipple attachment. In some cases, the fluid path includes a priming chamber and a dosing tube, where the dosing chamber has a first end, a second end, and a lumen. In some cases, a breast pump further includes a milk storage container having an opening. In some cases, the priming chamber includes an overflow aperture configured to allow fluid to flow from the priming chamber, through the opening in the milk storage container, and into the milk storage container. In some cases, the fluid path has a first section adjacent the nipple shield and a second section adjacent the throughput aperture. In some cases, the housing further includes a gate capable of preventing fluid flow between the first section of the fluid path and the second section of the fluid path. In some cases, the housing further includes a first sensor adjacent the gate. In some cases, the housing further includes a second sensor adjacent the throughput aperture.

In another aspect, embodiments of the present invention encompass methods for simultaneous breastmilk pumping and feeding that include expressing breastmilk from a breast using a breast pump having a nipple shield for receiving a nipple, a housing having a fluid path and a throughput aperture, the fluid path extending from the nipple shield to the throughput aperture, a negative pressure source, and a nipple attachment. Methods may also include collecting breastmilk in the fluid path, and positioning a baby to consume the breastmilk via the nipple attachment. Further, methods may include displacing the breastmilk to the baby in discrete quantities. In some methods, the fluid path has a first section adjacent the nipple shield and a second section adjacent the throughput aperture. In some methods, the housing can further include a gate capable of preventing fluid flow between the first section of the fluid path and the second section of the fluid path. In some methods, the gate is controlled manually. In some methods, the gate is controlled electronically. In some methods, the housing further includes a first sensor adjacent the gate, where the first sensor is configured to close the gate if the second section of the fluid path is full and/or open the gate if the second section of the fluid path is not full. In some methods, the housing further includes a second sensor adjacent the throughput aperture, and the second sensor is configured to open the gate if the second section of the fluid path is empty.

In still another aspect, embodiments of the present invention encompass methods for simultaneous breastmilk pumping and feeding that include expressing breastmilk from a breast using a breast pump having a nipple shield for receiving a nipple, a housing having a throughput aperture, a fluid path extending from the nipple shield to the throughput aperture, the fluid path having a first section adjacent the nipple shield and a second section adjacent the throughput aperture, the second section having a defined volume, a gate capable of preventing fluid flow between the first section of the fluid path and the second section of the fluid path, a negative pressure source, and a nipple attachment. Methods can also include collecting breastmilk in the first section of the fluid path, opening the gate to allow breastmilk to fill the second section of the fluid path, closing the gate when the second section of the fluid path is full, positioning a baby to consume the breastmilk via the nipple attachment, and recording the volume of breastmilk consumption. In some cases, methods also include transmitting breastmilk consumption data to an external device. In some cases, a breast pump can also include a mechanism for sensing a collapsing bag with a hall effect sensor system, which causes action of a peristaltic pump dispensing milk to an infant and allowing for quantification. Optionally, the milk container can be used as a part of the peristaltic pump by being a backing to provide counterpressure for the peristaltic rollers. In some cases, a breast pump includes a collapsible compartment with a magnet/hall effect and peristaltic tubing to orally dose on demand. In some cases, the pump is configured to monitor the amount anyone drinks on demand, to very small quantities.

As disclosed herein, a breast pump system can include a nipple attachment that decreases the number of components by incorporating a one way valve into the assembly. System and method embodiments disclosed herein can provide multiple nipple shapes and sizes that the user can switch in and out of the nipple assembly. Pump systems can also include valves in the fluid path that operate to prevent backflow in multiple areas of the fluid path. An increased number of valves can prevent leakage upon disassembly. In some cases, a diaphragm separator that is used to create vacuum suction at the breast can be provided as two pieces (two smaller diaphragms that add up to the same volume). In some cases, a milk container spout can have a cap that allows for venting and that can close off the container to prevent leaks. The cap can have three positions: (1) milk container closed, (2) milk container able to vent air, and (3) milk container completely open and ready to pour expressed milk to bottle.

These and other embodiments are described in further detail in the following description related to the appended drawing figures.

BRIEF DESCRIPTION OF THE DRAWINGS

Specific embodiments of the disclosed device, delivery systems, or methods will now be described with reference to the drawings. Nothing in this detailed description is intended to imply that any particular component, feature, or step is essential to the invention.

FIGS. 16A and 16B illustrate aspects of a breastmilk pumping and feeding device, in accordance with some embodiments.

FIGS. 17A to 17D depict aspects of a nipple attachment of a breastmilk pumping and feeding device, in accordance with some embodiments.

FIGS. 25A to 25F illustrate aspects of a breastmilk pumping and feeding device, in accordance with some embodiments.

FIGS. 26A to 26D illustrate aspects of a breastmilk pumping and feeding device, in accordance with some embodiments.

FIGS. 27A to 27E illustrate aspects of a breastmilk pumping and feeding device, in accordance with some embodiments.

DETAILED DESCRIPTION OF THE INVENTION

Figure 1:
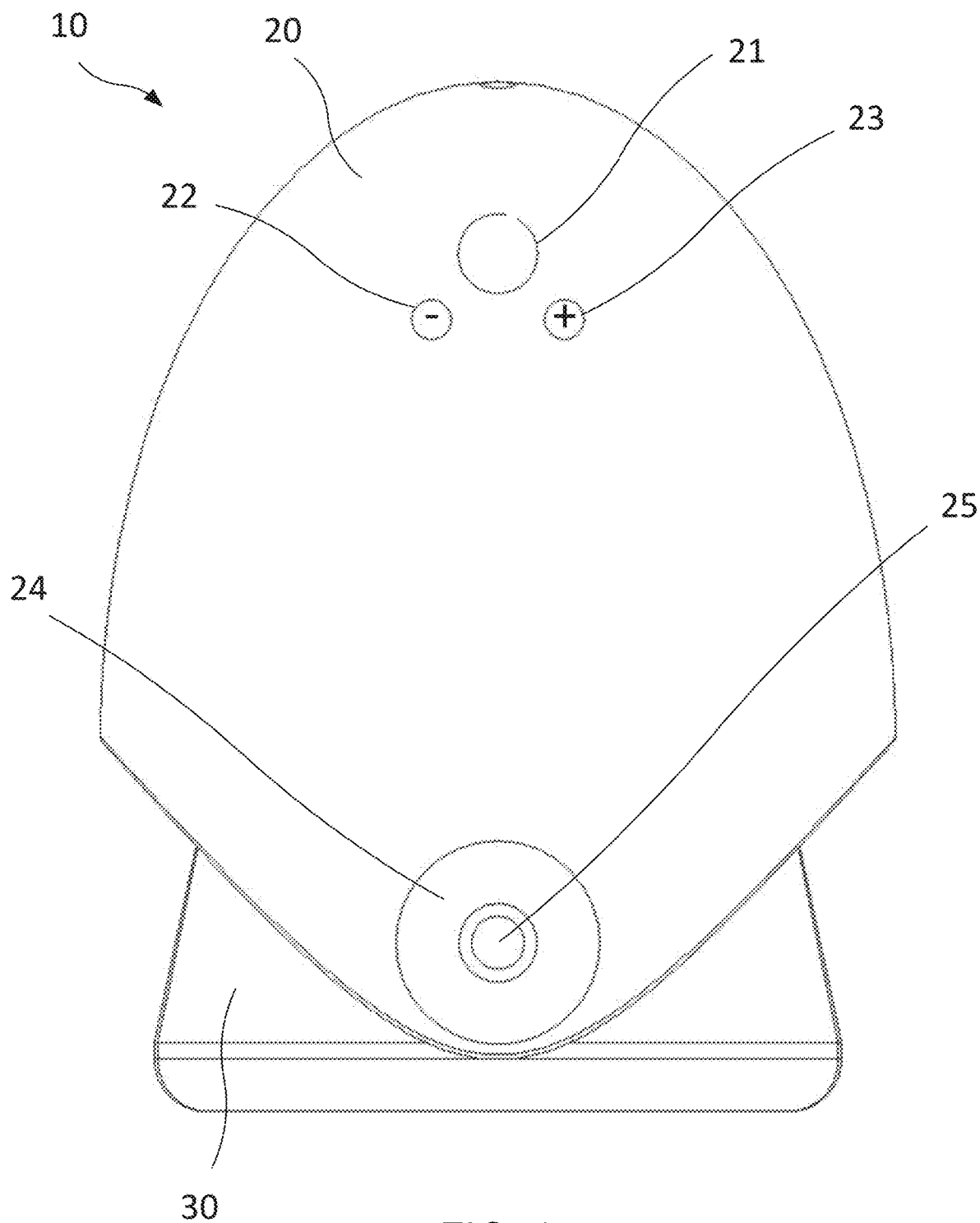
FIG. 1 shows a front view of a breastmilk pumping and feeding device, in accordance with some embodiments.

Specific embodiments of the disclosed device and method of use will now be described with reference to the drawings. Nothing in this detailed description is intended to imply that any particular component, feature, or step is essential to the invention.

It would be desirable to provide improved breast pump devices and methods that overcome some of the challenges of existing devices. For example, it would be desirable to provide a device that may both pump and feed a baby from the same apparatus at the same time. Additionally, it would be desirable to provide a device capable of quantifying the breastmilk displaced to a baby and transmit and record the consumption data for caregivers and healthcare providers. The embodiments described herein address at least some of these challenges and benefits.

Devices and methods as disclosed herein provide a pump capable of pumping breastmilk and simultaneously feeding breastmilk to a baby. Pumps as described herein may be used in a hospital setting or at home. In some embodiments, pumps as provided herein may further quantify breastmilk displaced to a baby. It is understood that although certain descriptions disclosed herein refer to the dispensing of feeding fluid to an infant (e.g. a child who is one year old or younger), embodiments of the present invention encompass the dispensing of feeding fluid to any child who is breastfeeding, or any individual who is consuming a feeding fluid.

In some embodiments, systems encompass an all-in one pumping/feeding/counting device having peristaltic pump, collapsible chamber, and counter features. In some embodiments, systems encompass a peristaltic on-demand dosed bottle. In some embodiments, systems encompass a feeding and pumping device. In some embodiments, systems encompass an air pressure counting mechanism.

In some instances, certain terms may be used interchangeably. For example, in some embodiments, the terms "feedbag", "compressible chamber", "compressible bag", "collapsible chamber", "collapsible compartment", and "compressible compartment" may be used interchangeably. In some embodiments, a "breastmilk pumping and feeding device" may refer to a "breastmilk pumping, feeding, and quantification device" and vice versa, for example depending on the combination of elements contained in the device.

In some embodiments, the terms "nipple ring", "nipple attachment", "smart nipple", and "nipple component" can be used interchangeably. In some embodiments, the terms "nipple shield" and "breast flange" can be used interchangeably. In some embodiments, the terms "nipple", "artificial teat", and "feeding apparatus" can be used interchangeably.

In some embodiments, a system for determining an amount of a feeding fluid that is displaced or dispensed to a baby includes elements such as a chamber that stores feeding fluid, a dosing mechanism that receives discrete packets of feeding fluid from the chamber (each discrete packet having a discrete packet volume), a compressible chamber or feedbag that receives discrete packets of feeding fluid from the dosing mechanism, a nipple that receives feeding fluid from the feedbag and allows feeding fluid to flow to the infant, a sensor that detects when the feedbag is available to receive a new discrete packet of feeding fluid from the dosing mechanism, and a counting mechanism that registers a count each time the dosing mechanism dispenses a new discrete packet of feeding fluid to the feedbag. In some cases, a system further includes a processor that determines the amount of feeding fluid that is dispensed to the infant based on the discrete packet volume and the number of registered counts. In some embodiments, the sensor is not a flow sensor that reads the amount of milk flowing through a line. In some cases, the number of rotations can be counted using a manual method of counting and/or an analog method of counting. In some embodiments, the number of rotations of the peristaltic pump is counted using a hall effect sensor. In some embodiments, the number of rotations of the peristaltic pump can be counted by a magnetic encoder. Embodiments of the present invention encompass the use of any of a variety of counting mechanisms for counting the number of rotations (or partial rotations) of the peristaltic pump, which may cause the dispensing of a discrete volume of feeding fluid from the dosing mechanism.

Figure 4:
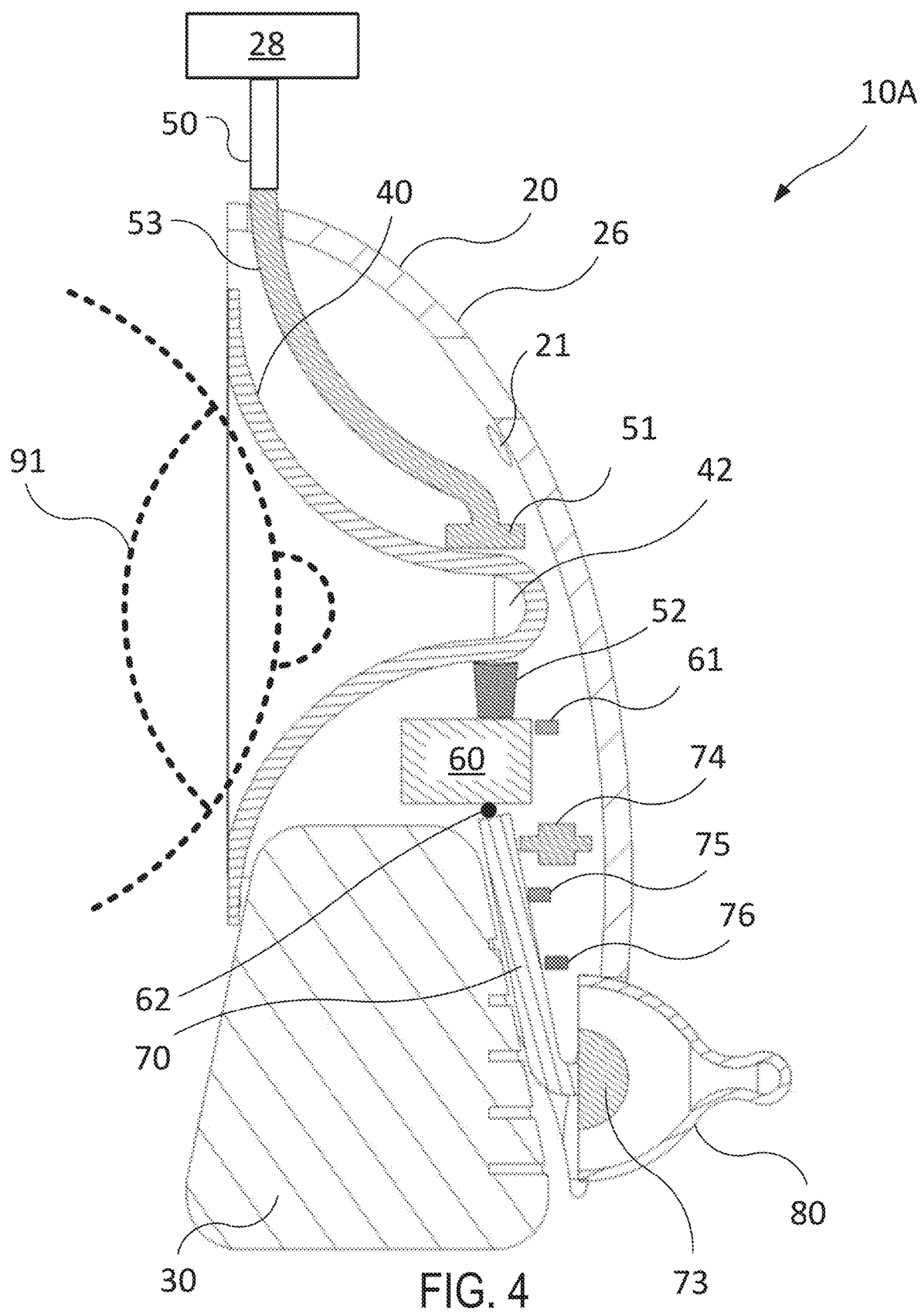
FIG. 4 shows an internal configuration of a housing, in accordance with some embodiments.

FIG. 1 shows a front view of a housing 20 of a breastmilk pumping and feeding device 10. Housing 20 may be made from molded plastic or similar material. In some embodiments, housing 20 comprises a nipple attachment indent 24 and throughput aperture 25. Nipple attachment indent 24 may be about 1 mm to 50 mm deep and may be circular, oval, or any other shape to receive various size nipple attachments (e.g., component 80 as shown in FIG. 4). Throughput aperture 25 may be circular and sized to allow breastmilk to exit device 10. In some embodiments, throughput aperture 25 may be sized to receive a backflow valve (e.g. component 73 as shown in FIG. 4). In some embodiments, breastmilk pumping and feeding device 10 may be pre-configured with a breastmilk storage container 30 in place. Breastmilk storage container 30 may be positioned below or behind nipple attachment indent 24. Breastmilk storage container 30 may be made from food grade plastic, silicone, or similar material. In some embodiments, housing 20 further comprises a pump power button 21, a pump decrease button 22, and an increase button 23. The pump power button 21 may power a negative pressure source and it may power sensors within the device. Decrease button 22 and increase button 23 may control negative pressure level (e.g. as provided by the negative pressure source). Decrease button 22 and increase button 23 may control negative pressure frequency (e.g. as provided by the negative pressure source).

Figure 2:
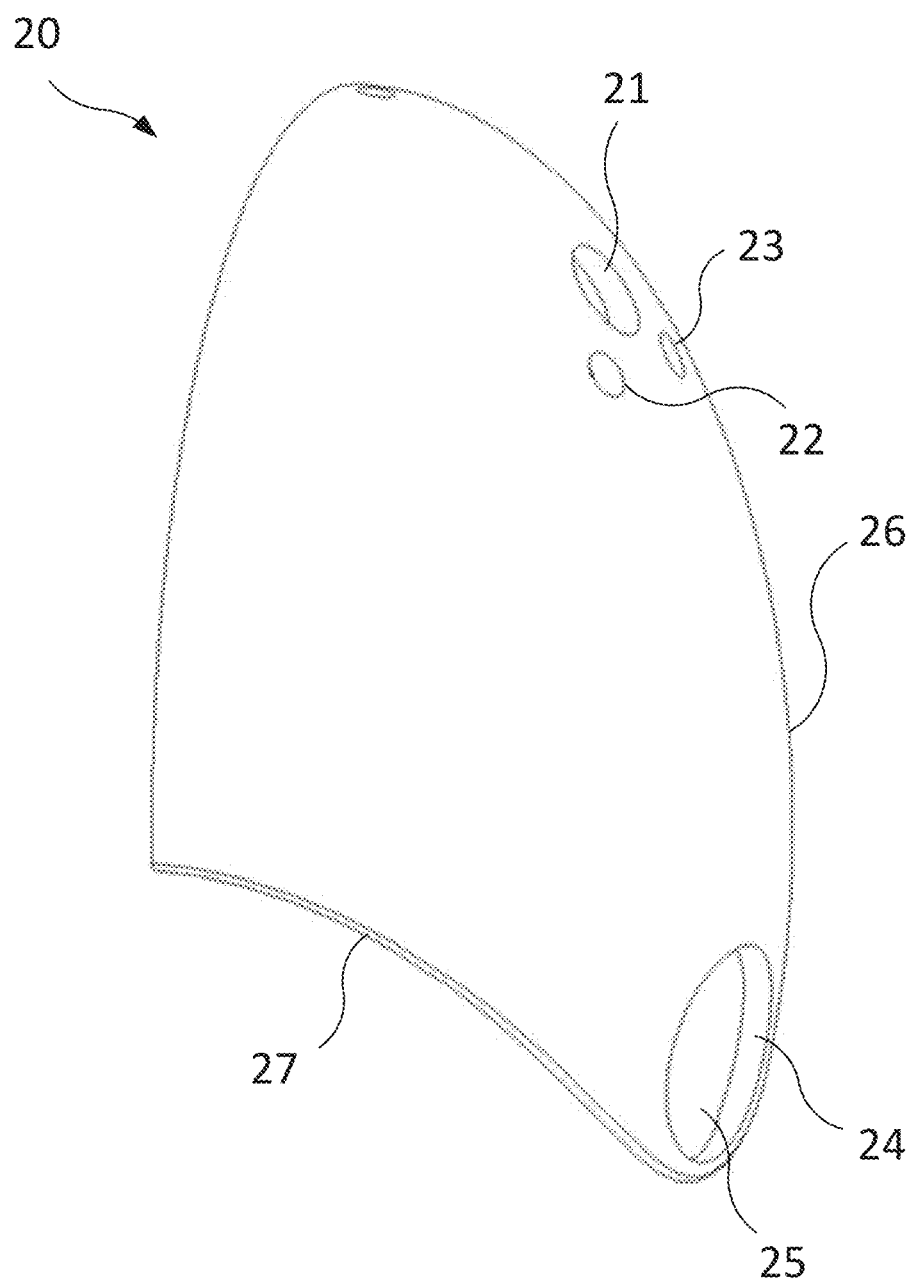
FIG. 2 shows a configuration of a housing, in accordance with some embodiments.

FIG. 2 shows a perspective view of a housing 20. Housing 20 may be made from molded plastic or similar material. In some embodiments, housing 20 comprises a nipple attachment indent 24 and throughput aperture 25. Nipple attachment indent 24 may be about 1 mm to about 50 mm deep and may be circular, oval, or any other shape to receive various size nipple attachments. Throughput aperture 25 may be circular and sized to allow breastmilk to exit device 10. In some embodiments, housing 20 further comprises a pump power button 21, a pump decrease button 22, and an increase button 23. The pump power button 21 may power or be in operative association with a negative pressure source and it may power or be in operative association with one or more sensors within the breastmilk pumping and feeding device. Decrease button 22 and increase button 23 may control negative pressure level (e.g. as provided by the negative pressure source). Decrease button 22 and increase button 23 may control negative pressure frequency (e.g. as provided by the negative pressure source). Housing 20 may comprise outer profile 26 shaped to approximate a breast. Outer profile 26 may optionally comprise a soft or plush outer layer to interface with a baby. Housing 20 may further comprise a container cavity 27 sized and shaped to receive a breastmilk storage container (e.g., component 30 as shown in FIG. 1).

Figure 3:
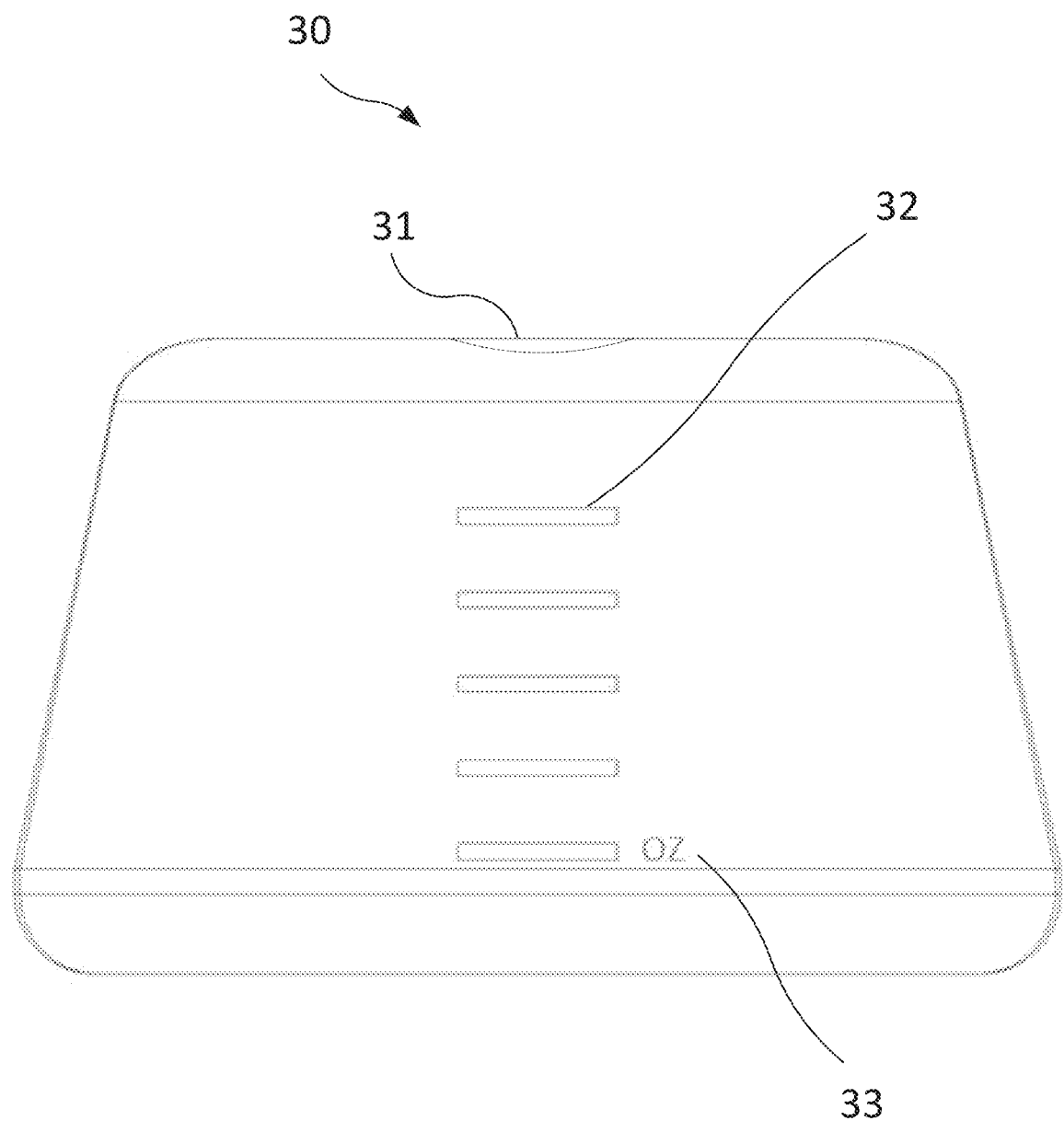
FIG. 3 shows a configuration of a breastmilk storage container, in accordance with some embodiments.

FIG. 3 shows a perspective view of a breastmilk storage container 30, in accordance with some embodiments. Breastmilk storage container 30 may be made from food grade plastic, silicone, or similar material. Breastmilk storage container 30 may be cylindrical, rectangular prism, or any other shape. Breastmilk storage container 30 may comprise an opening 31 to receive breastmilk. Opening 31 may be circular, rectangular, or any other shape. Breastmilk storage container 30 may further comprise one or more than one volume marking 32 and unit of measurement marking 33. Unit of measurement marking 33 may indicate ounces or milliliters or another unit of volume. Volume marking 32 may be placed to indicate, for example, 1 ounce of breastmilk. Volume marking 32 may repeat to indicate, for example, additional ounces or volume of breastmilk. In some embodiments, a volume capacity of a breastmilk storage container 30 may range from about 1 ounce to about 14 ounces.

FIG. 4 shows an internal configuration of a housing of a system 10A, in accordance with some embodiments. Housing 20 may be made from molded plastic or similar material. In some embodiments, housing 20 further comprises a pump power button 21, a pump decrease button (e.g., component 22 as shown in FIG. 1), and an increase button 23. The pump power button 21 may power or be in operative association with a negative pressure source 28 and it may power or be in operative association with one or more sensors within the breastmilk pumping and feeding device. Increase button 23 may control negative pressure level (e.g. as provided by the negative pressure source). Increase button 23 may control negative pressure frequency (e.g. as provided by the negative pressure source). Housing 20 may comprise outer profile 26 shaped to approximate a breast. Outer profile 26 may optionally comprise a soft or plush outer layer to interface with a baby. Housing 20 may be pre-configured with a breastmilk storage container 30 in place. Breastmilk storage container 30 may be made from food grade plastic, silicone, or similar material.

Housing 20 may further comprise a nipple shield 40 to receive a nipple 91 on a breast 90. Nipple shield 40 may be provided in a variety of funnel shaped sizes to accommodate and support varying nipple 91 sizes. Nipple shield 40 may create a seal around nipple 91. Breastmilk may flow or otherwise travel or express from nipple 91 into an interior chamber 42 defined by the nipple shield. Nipple shield 40 may snap into housing 20 to allow for removal of nipple shield 40 for cleaning. Housing 20 may further comprise connection 50 to an external negative pressure source 28, channel 53, a first backflow valve or flow control mechanism 51, and a second backflow valve or flow control mechanism 52. Channel 53 allows negative pressure to be applied to nipple attachment first backflow valve 51 and nipple attachment 40. In this way, operation of the negative pressure source 28 can create, modulate, or otherwise control negative pressure within the interior chamber 42 of nipple shield 40. First backflow valve 51 may be positioned adjacent channel 53 and nipple shield 40. First backflow valve 51 may be configured to prevent breastmilk from moving from the interior chamber 42 of nipple shield 40 into channel 53. In this way, a breastmilk pumping and feeding device may provide and/or control fluid communication between the negative pressure source 28 and the interior chamber 42 of nipple shield 40 (e.g. when a seal exists between nipple shield 40 and the skin at or near the nipple 91).

In some embodiments, housing 20 may further comprise a priming chamber 60. In some cases, as further discussed elsewhere herein, a housing may not include a priming chamber. Second backflow valve 52 may be configured to only allow breastmilk to flow from the interior chamber 42 of nipple shield 40 into priming chamber 60. Priming chamber 60 may be made from food grade plastic, silicone, or similar material. Priming chamber 60 may have a volume capacity of about 5 milliliters to about 30 milliliters. Priming chamber 60 may be cylindrical or any other shape and may be open on one end. Priming chamber 60 may further comprise a priming chamber cap 62. Priming chamber cap 62 may be configured to close an open end of priming chamber 60 during usage and may be removed from priming chamber 60 after usage to allow for cleaning. Housing 20 may further comprise a priming sensor 61 adjacent priming chamber 60. Priming sensor 61 may be configured to determine if there is a specified amount of breastmilk in priming chamber 60. Priming sensor 61 may be infrared, inductive, or any other configuration. In this way, a breastmilk pumping and feeding device may provide and/or control fluid communication between the interior chamber 42 of nipple shield 42 and the priming chamber 60 (e.g. when a seal exists between nipple shield 40 and the skin at or near the nipple 91).

Housing 20 may comprise dosing tube 70, a third backflow valve or flow control mechanism 73, and nipple attachment 80. Dosing tube 70 may be made from food grade plastic, silicone, or similar material. In some embodiments, such a tube 70 can be activated with a peristaltic pump mechanism, as discussed elsewhere herein. Dosing tube 70 may be about 20 milliliters to about 70 millimeters in length. Dosing tube 70 may have a volume capacity of about 0.3 milliliters to about 5 milliliters. Dosing tube 70 may be adjacent to or extend into priming chamber 60, thus a fluid path may exist between dosing tube 70 and priming chamber 60. Dosing tube 70 may provide a fluid path from priming chamber 60 to third backflow valve 73. Dosing tube 70 may snap into backflow valve 73. Dosing tube 70 may be removed from housing 20 for cleaning. Backflow valve 73 may be configured to allow fluid to flow from dosing tube 70 to nipple attachment 80 and to prevent fluid flow from nipple attachment 80 to dosing tube 70. In this way, a breastmilk pumping and feeding device may provide and/or control fluid communication between the priming chamber 60 and the dosing tube 70 and likewise provide and/or control fluid communication between the dosing tube 70 and the nipple attachment 80. Nipple attachment 80 may be sized and shaped to approximate nipple 91. Housing 20 may further comprise gate 74, full sensor 75, and empty sensor 76. As further discussed elsewhere herein, in some embodiments, a housing may not include a full sensor and/or an empty sensor. Full sensor 75 may be configured to indicate if dosing tube 70 is full of fluid. Empty sensor 76 may be configured to indicate if dosing tube 70 is empty. Gate 74 may be configured such that it pinches dosing tube 70 to prevent fluid flow unless empty sensor 76 indicates that dosing tube 70 is empty. Full sensor 75 and empty sensor 76 may be infrared, inductive, or any other configuration.

In this way, embodiments of the present invention encompass the use of a system 10A for determining an amount of a feeding fluid that is consumed by an infant, where the system includes a chamber that stores feeding fluid and a dosing mechanism that receives feeding fluid from the chamber, and dispenses discrete packets of feeding fluid, each discrete packet having a discrete packet volume. The system further includes a nipple that receives feeding fluid dispensed by the dosing mechanism and that allows feeding fluid to flow to the infant, and a sensor assembly that determines when the dosing mechanism is ready to dispense a new discrete packet of feeding fluid. Further, the system can include a counting mechanism that registers a count for each dispensing event performed by the dosing mechanism, and a processor that determines the amount of feeding fluid that is consumed by the infant based on the discrete packet volume and the number of registered counts.

Figure 5:
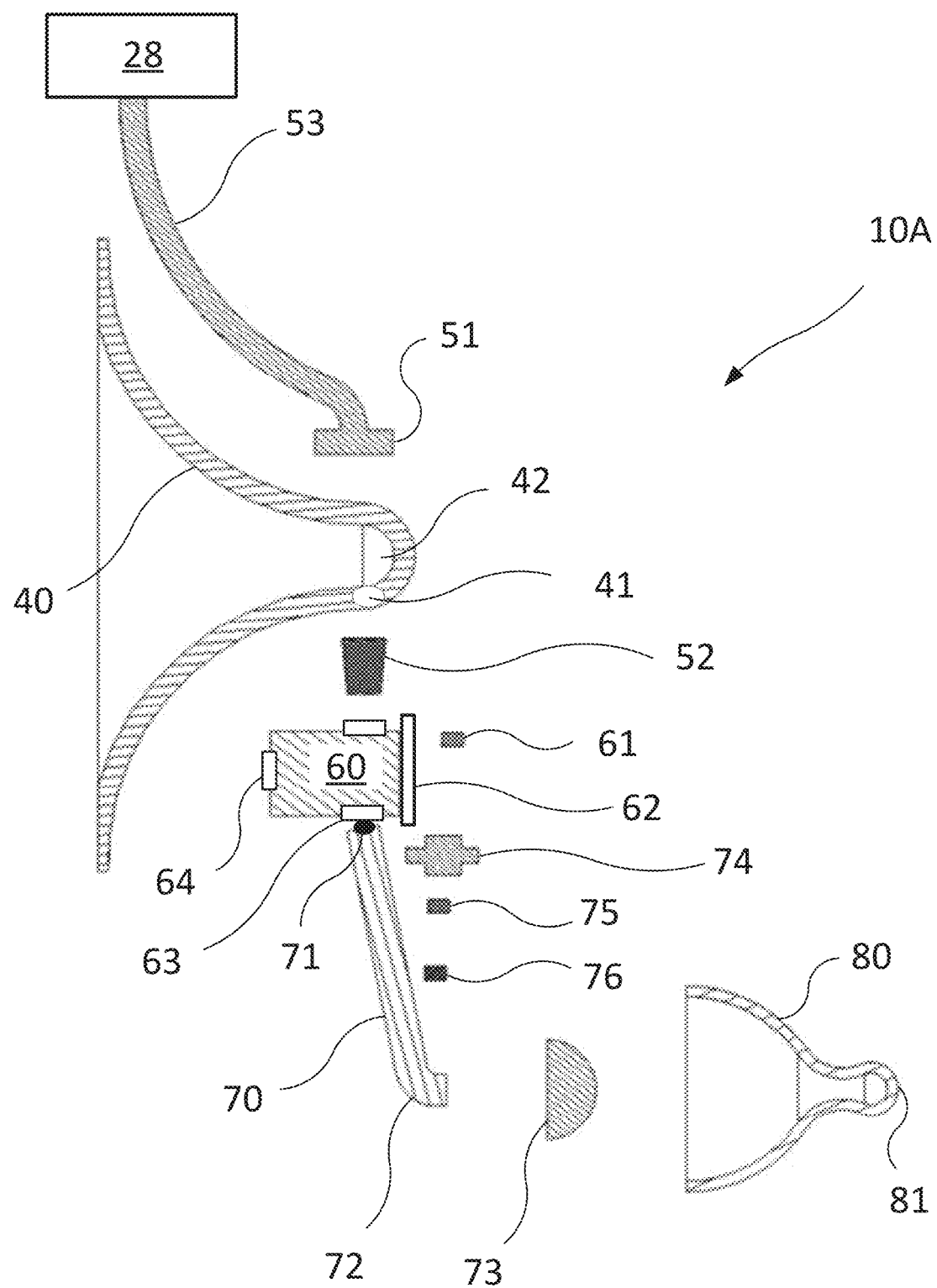
FIG. 5 show an exploded view of internal components of a housing, in accordance with some embodiments.

FIG. 5 show an exploded view of internal components of a housing, in accordance with some embodiments. Housing 20 (e.g. as shown in FIG. 1) may comprise a nipple shield 40. Nipple shield 40 may be provided in a variety of funnel shaped sizes. Additionally, nipple shield 40 may comprise an aperture 41. Nipple shield 40 may have or define an interior chamber 42. Housing 20 (e.g. as shown in FIG. 1) may further comprise channel 53, a first backflow valve 51, and a second backflow valve 52. Channel 53 allows negative pressure to be applied (e.g. from negative pressure source 28) to nipple attachment first backflow valve 51 and nipple attachment 40. First backflow valve 51 may be positioned adjacent channel 53 and nipple shield 40. First backflow valve 51 may be configured to prevent breastmilk from moving from interior chamber 42 into channel 53. First backflow valve 51 may be configured to allow flow from channel 53 into interior chamber 42. In some embodiments, housing 20 (e.g. as shown in FIG. 1) may further comprise a priming chamber 60. In some cases, as discussed elsewhere herein, a housing may not include a priming chamber. Second backflow valve 52 may snap into aperture 41 of nipple shield 40. Second backflow valve 52 may be configured to only allow breastmilk to flow from interior chamber 42 into priming chamber 60. Second backflow valve 52 may be configured to prevent flow from priming chamber 60 into interior chamber 42. Priming chamber 60 may be made from food grade plastic, silicone, or similar material. Priming chamber 60, which may be replaced with or referred to as a feedbag, may have a volume capacity of 5 to 30 milliliters. Priming chamber 60 may be cylindrical or any other shape and may be open on one end. Priming chamber 60 may further comprise a priming chamber cap 62. Priming chamber cap 62 may be configured to close an open end of priming chamber 60 during usage and may be removed from priming chamber 60 after usage to allow for cleaning. Housing 20 (e.g. as shown in FIG. 1) may further comprise a priming sensor 61 adjacent priming chamber 60. Priming sensor 61 may be configured to determine if there is a specified amount of breastmilk in priming chamber 60. Priming sensor 61 may be infrared, inductive, or any other configuration. Priming chamber 60 may further comprise an overflow aperture 64 that allows breastmilk to overflow into a breastmilk storage container (e.g., component 30 as shown in FIG. 1). In some embodiments, as discussed elsewhere herein, a priming chamber or feedbag may not include such an overflow aperture. Priming chamber 60 may further comprise dosing tube aperture 63.

Housing 20 (e.g. as shown in FIG. 1) may comprise dosing tube 70, a third backflow valve 73, and nipple attachment 80. Dosing tube 70 may be made from food grade plastic, silicone, or similar material. Dosing tube 70 may be about 20 millimeters to about 70 millimeters in length. Dosing tube 70 may have a volume capacity of about 0.3 milliliters to about 5 milliliters. Dosing tube 70 may be adjacent to or extend into dosing tube aperture 63 of priming chamber 60. Dosing tube 70 may comprise aperture 71 to provide a fluid path from priming chamber 60 to third backflow valve 73. Dosing tube 70 may further provide a bend 72 to accommodate third backflow valve 73 orientation. Dosing tube 70 may snap into backflow valve 73. Dosing tube 70 may be removed from housing 20 for cleaning. Backflow valve or fluid control mechanism 73 may be configured to allow fluid to flow from dosing tube 70 to nipple attachment 80 and to prevent fluid flow from nipple attachment 80 to dosing tube 70. Nipple attachment 80 may be sized and shaped to approximate a nipple. Nipple attachment 80 may include a distal exit port or aperture 81. In some cases, nipple attachment 80 may be referred to as a baby drinking nipple, an infant nipple, or a bottle nipple. Housing 20 may further comprise gate 74, full sensor 75, and empty sensor 76. Full sensor 75 may be configured to indicate if dosing tube 70 is full of fluid. Empty sensor 76 may be configured to indicate if dosing tube 70 is empty. In some cases, a bubble sensor can be configured to provide an indication or notification to the device if there is liquid present in the tube leading to the feedbag or priming chamber. Gate 74 may be configured such that it pinches dosing tube 70 to prevent fluid flow unless empty sensor 76 indicates that dosing tube 70 is empty. Full sensor 75 and empty sensor 76 may be infrared, inductive, or any other configuration.

Figure 6:
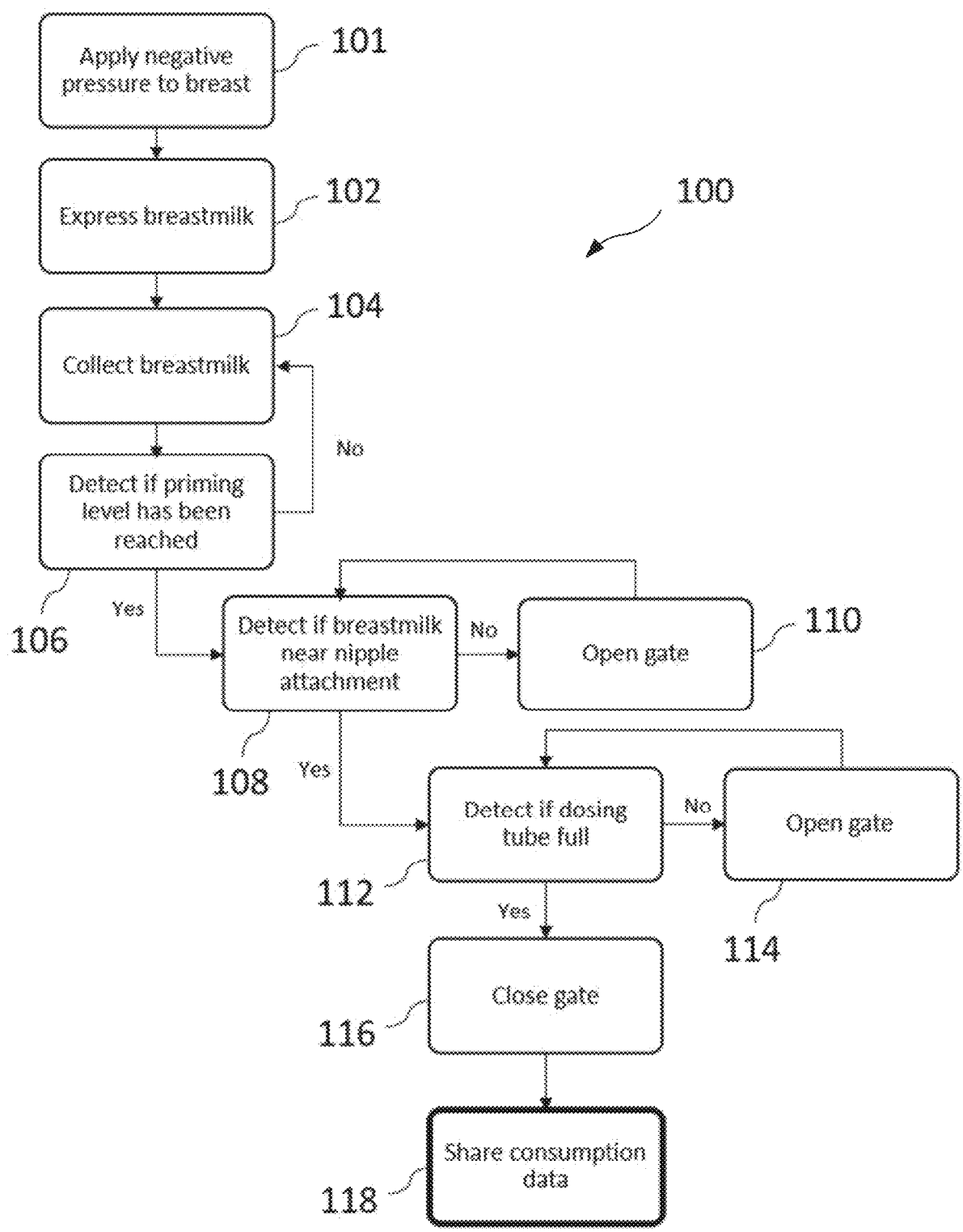
FIG. 6 shows a flow chart illustrating the method of quantifying breastmilk displaced to a baby, in accordance with some embodiments.

FIG. 6 shows a flow chart illustrating a method 100 of quantifying breast breastmilk displaced to a baby during simultaneous pumping and feeding, in accordance with some embodiments. In a first step 101, a negative pressure source may apply negative pressure to a breast, producing a second step 102 of breastmilk expression from a breast. In a third step 104, breastmilk may be collected in a priming chamber. As discussed elsewhere herein, in some cases a device may not include a priming chamber, and may instead include a peristaltic tube and wheel mechanism. Further, in some embodiments, breastmilk may be collected in a priming chamber and excess breastmilk may overflow into a breastmilk storage container. In a fourth step 106, a first sensor may detect if a priming chamber is full. Method 100 may not move forward until a priming level has been reached. Additionally, method 100 may move forward if a priming level has been reached. In a fifth step 108, a second sensor may detect if there is breastmilk near a nipple attachment from which a baby consumes breastmilk. If there is no breastmilk near a nipple attachment, then in a sixth step 110, a gate opens to allow breastmilk to flow from priming chamber into a dosing tube. Fifth step 108 may repeat until a second sensor detects that there is breastmilk near a nipple attachment. In a seventh step 112, if there is breastmilk near a nipple attachment, a third sensor may detect if a dosing tube is full. If a dosing tube is not full, then in an eighth step 114, a gate opens to allow breastmilk to flow from priming chamber into a dosing tube. In a ninth step 116, if a dosing tube is full, then a gate may close to prevent breastmilk from exiting a priming chamber (e.g. and into a dosing tube). In a tenth step 118, data is transmitted to a personal device (e.g. computer or smart phone) indicating that one unit of breastmilk equivalent to the volume of the dosing tube has been displaced to a baby.

Figure 6A:
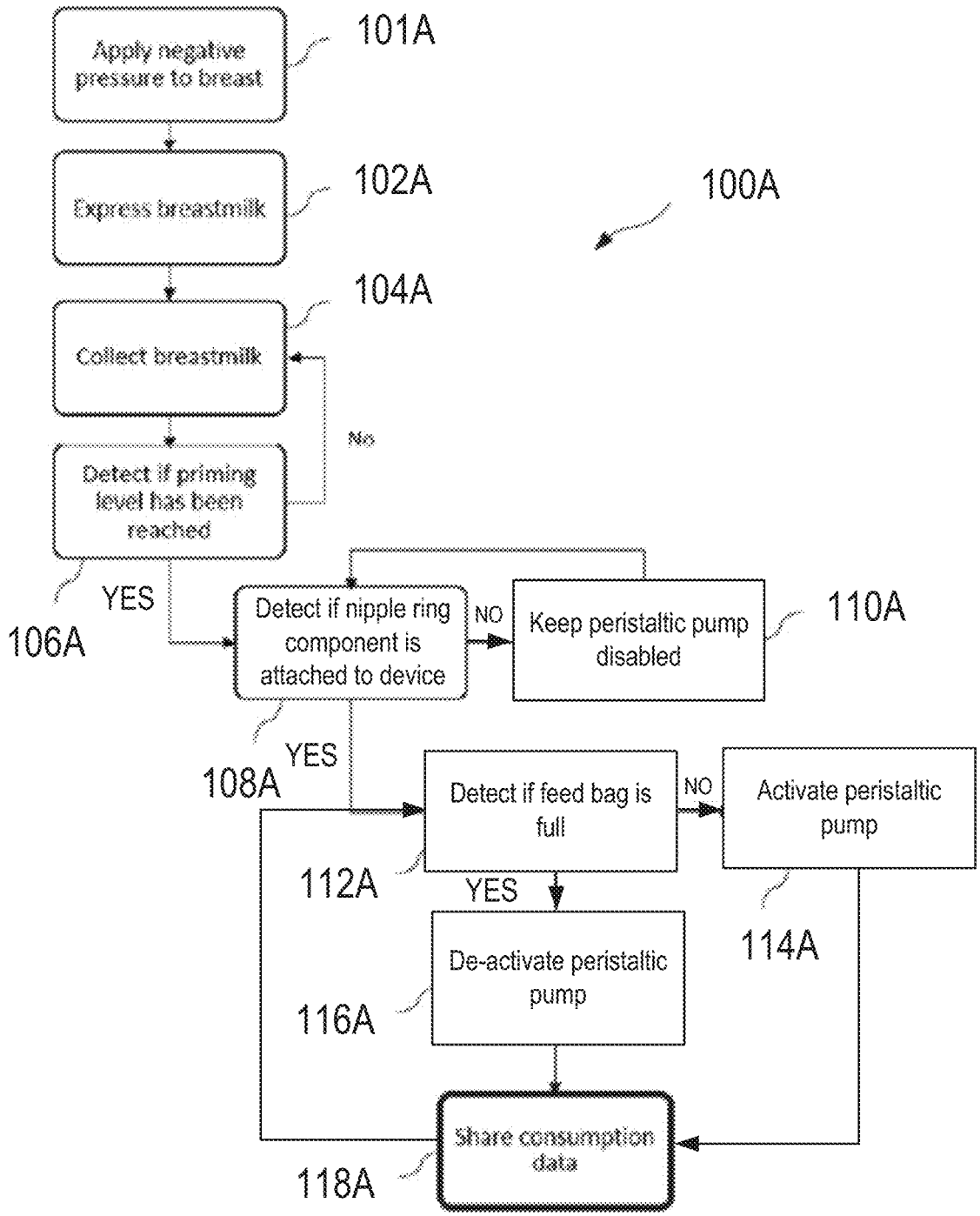
FIG. 6A shows a flow chart illustrating the method of quantifying breastmilk displaced to a baby, in accordance with some embodiments.

As discussed elsewhere herein, instead of using a dosing tube and priming chamber, breastmilk pumping and feeding device embodiments can use a peristaltic pump mechanism. Additional aspects of such embodiments can be further understood with reference to FIG. 6A. As illustrated in this flow chart, a method 100A of quantifying breast breastmilk displaced to a baby during simultaneous pumping and feeding can include various steps. In a first step 101A, a negative pressure source or other mechanism may apply negative pressure to a breast, producing a second step 102A of breastmilk expression from a breast. In a third step 104A, breastmilk may be collected. In a fourth step 106A, a first sensor may detect if a priming level has been reached. Method 100A may not move forward until a priming level has been reached. Additionally, method 100A may move forward if a priming level has been reached. In a fifth step 108A, a second sensor may detect if a nipple ring component or smart ring is attached to the device. If there is no nipple ring component attached to the device, then in a sixth step 110A, a peristaltic pump is kept disabled. Fifth step 108A may repeat until a second sensor detects that there is a nipple ring component attached to the device. In a seventh step 112A, if there is breastmilk near a nipple attachment, a third sensor may detect if a feedbag is full. If a feedbag is not full, then in an eighth step 114A, a peristaltic pump is activated to facilitate flow of breastmilk into the feedbag. In a ninth step 116A, if a feedbag is full, then a peristaltic pump may be de-activated. In a tenth step 118A, data is transmitted to a personal device (e.g. computer or smart phone) to share consumption data or that a certain amount of breastmilk has been displaced to a baby.

Figure 7:
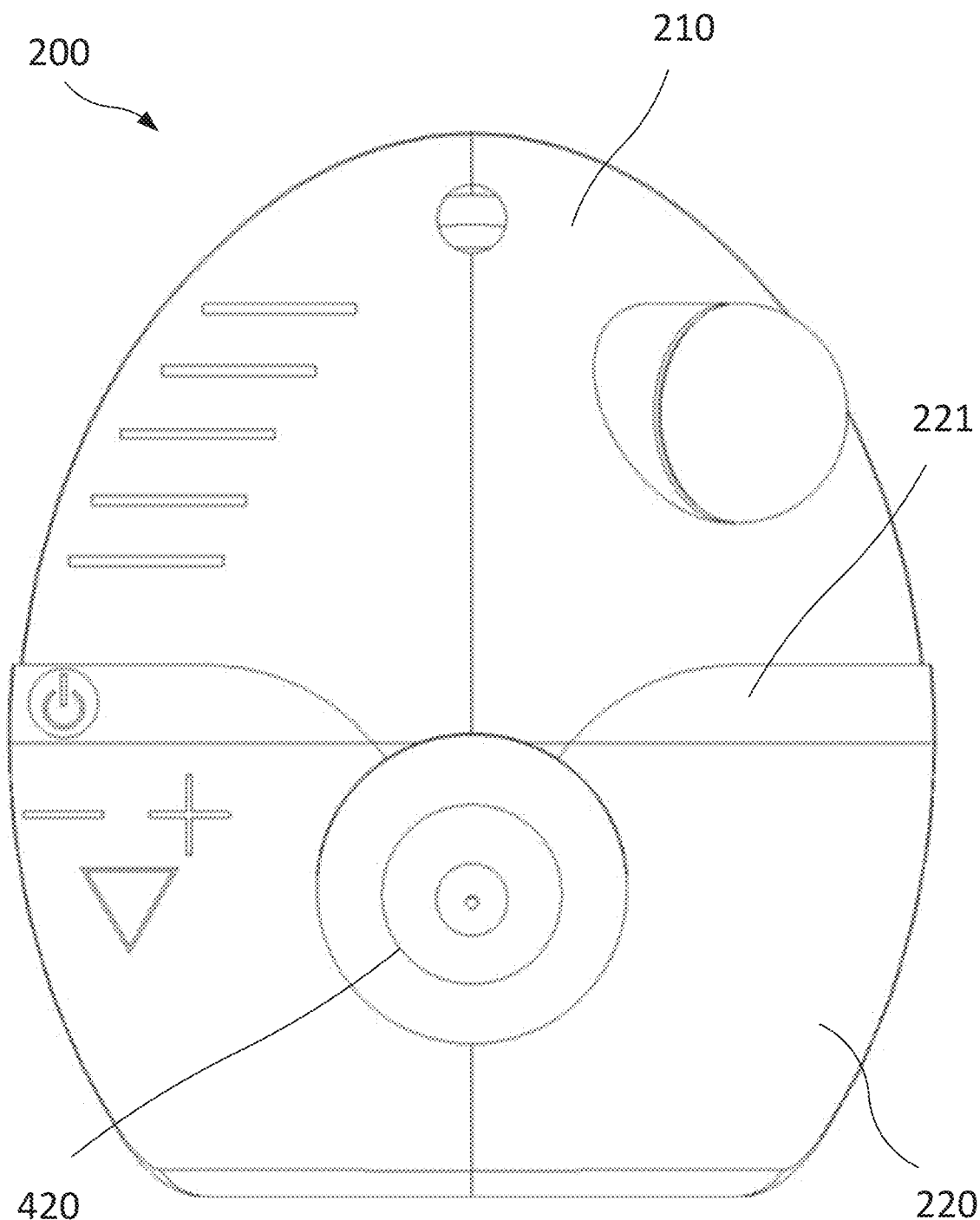
FIG. 7 illustrates aspects of a breastmilk pumping and feeding device, in accordance with some embodiments.

FIG. 7 depicts aspects of a breastmilk pumping and feeding device 200, according to embodiments of the present invention. As shown here, device 200 is in an assembled configuration, and includes a top container assembly 210 and a bottom housing assembly 220. The top container assembly 210 and the bottom housing assembly 220 are coupled together. As further discussed herein device 200 also includes a nipple attachment 420. Bottom housing assembly 220 includes a curved surface 221 that is configured to resemble a demi bra or lotus flower design.

Figures 8A, 8B:
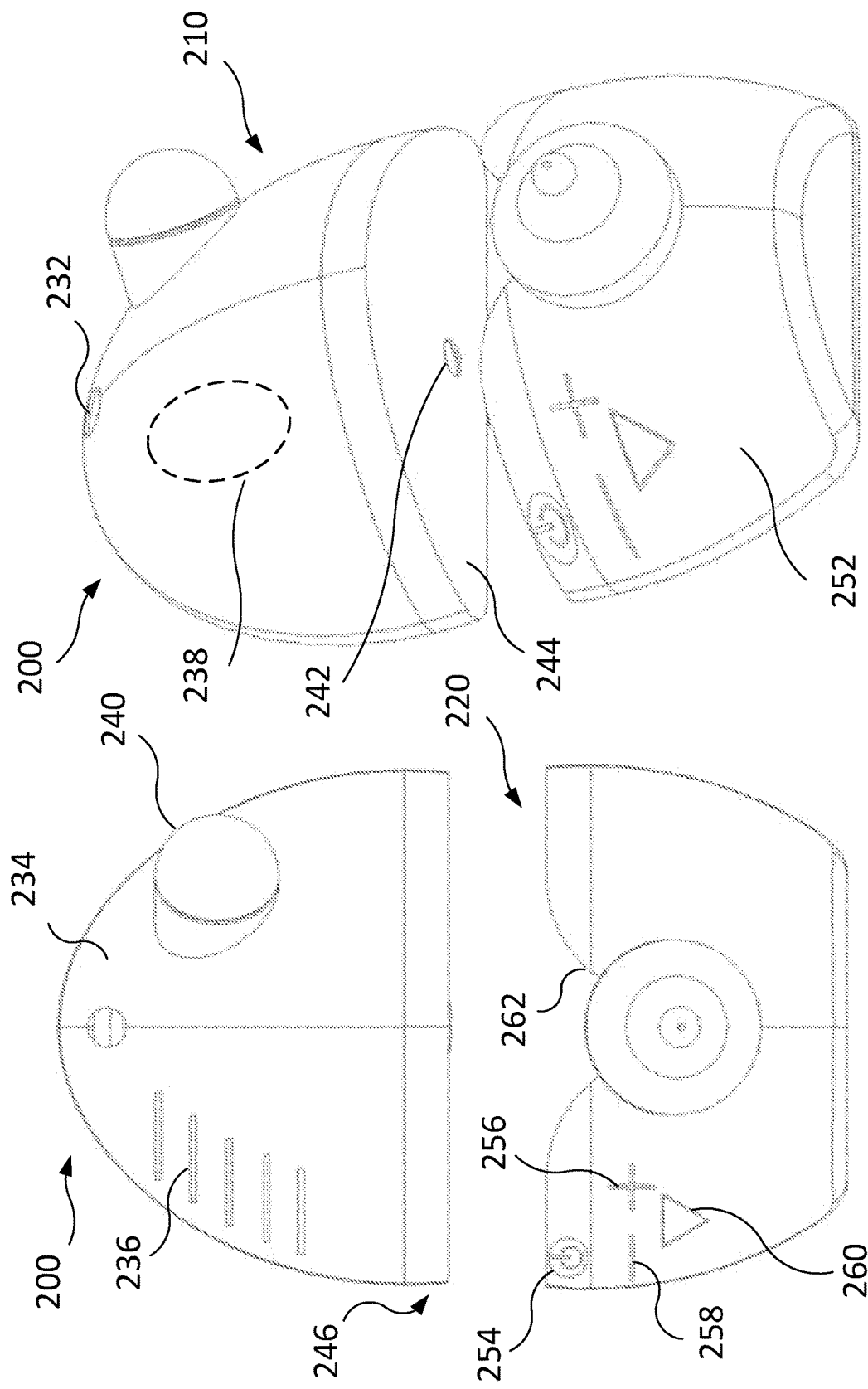
FIGS. 8A and 8B show exploded views of a breastmilk pumping and feeding device, in accordance with some embodiments.

FIGS. 8A and 8B provide exploded or unassembled views of breastmilk pumping and feeding device 200. As illustrated here, top container assembly 210 includes a pour spout having a vent hole or aperture 232, a container 234 (e.g. a clear milk container), graduated markings 236, a nipple shield opening or aperture 238 (e.g. into which a nipple shield may snap in to, or otherwise engage or attach), and a negative pressure port 240 that is configured to engage a source of or conduit with a negative pressure source. In some cases, negative pressure port 240 is configured to engage a pump flange housing. In some cases, negative pressure port 240 is configured to attach with a pump flange housing in a snap-on engagement. Port 240 may also operate as a port for a closed system vacuum flange. Top container assembly 210 also includes a feeding tube connection mechanism 242, which is configured to attach with or otherwise engage a feeding tube. In some cases, feeding tube connection mechanism 242 is a valve or a port. In some cases, feeding tube connection mechanism 242 is a flexible valve. Top container assembly 210 may also have a bottom surface 244 that is flat, so that the top container assembly 210 will remain stable when placed or rested on a surface, such as a flat surface, for example when the top container assembly 210 is disengaged or separated from the bottom housing assembly 220. As further illustrated in FIGS. 8A and 8B, bottom housing assembly 220 includes an electronics housing 252, a power button 254, an increase vacuum button 256, a decrease vacuum button 258, and a "let down" to baby button 260. The electronics housing 252 may be configured to house sensors, pump hardware, and other components. As discussed elsewhere herein, the pump part of the assembly may become the bottom part in another embodiment. Bottom housing assembly 220 can also include a slit 262 that is configured to receive a feeding tube and/or nipple attachment. In some embodiments, as discussed elsewhere herein, a bottom housing assembly may not include a slit. Bottom housing assembly 220 generally provides a recess that is shaped or configured to receive a bottom portion 246 of the top container assembly 210, for example in a nested arrangement. In some cases, feeding tube connection mechanism 242 can be provided as a hole or aperture that provides fluid flow out through the bottom or lower side or surface 244 of the container 234.

Figure 9:
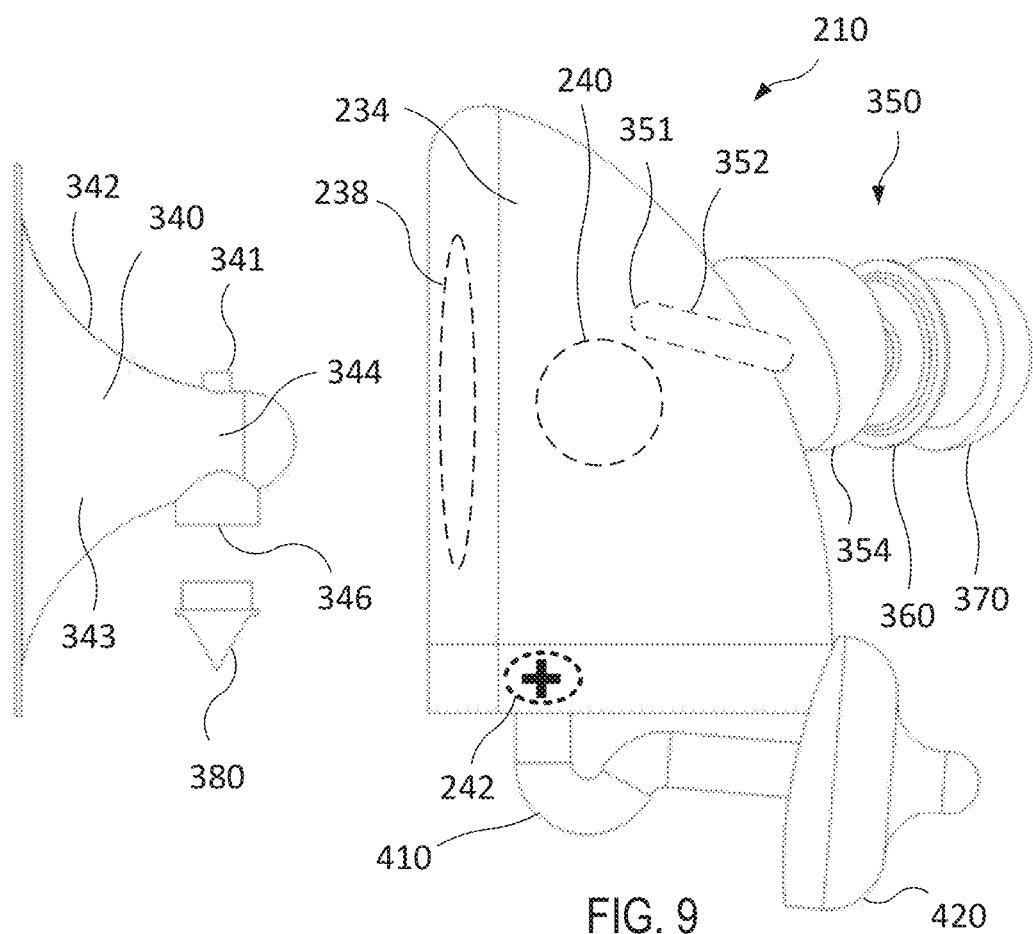
FIG. 9 shows an exploded view of upper components of a breastmilk pumping and feeding device, in accordance with some embodiments.

FIG. 9 depicts additional aspects of a breastmilk pumping and feeding device, which includes a top container assembly 210, a nipple shield 340, a pump flange mechanism 350 having a pump flange tube 352 and a pump flange housing 354, and a pump flange 360.

The top container assembly 210 has a container 234 (e.g. a clear milk container), a nipple shield opening or aperture 238 (e.g. into which the nipple shield 340 may snap in to, or otherwise engage or attach), and a negative pressure port 240 that is configured to engage a source of or conduit with a negative pressure source. In some cases, nipple shield 340 includes an engagement rim or snap-on rim 342, which couples with the nipple shield opening 238 of the container 234 (e.g. when the barrel 344 of the nipple shield 340 is positioned within the interior of container 234). Nipple shield 340 may also include or be in fluid communication with a nipple shield negative pressure port 341, which in turn engages with a distal end 351 of the pump flange tube 352. For example, nipple shield negative pressure port 341 may be in fluid communication with distal end 351 of the pump flange tube, when the port and the distal end 351 are both disposed within the interior of the container 234.

The container negative pressure port 240 can be configured to engage the pump flange housing 354 of the pump flange mechanism 350. In some cases, the container negative pressure port 240 and the pump flange housing 354 are configured to couple in a snap-on fashion. In some cases, the pump flange housing 354 is provided as a solid component. The pump flange 360 can be flexible, and can operate to prevent milk from entering the pump or a negative pressure source 370. In some cases, the negative pressure source 370 can operate to provide negative pressure to the barrel 344 or interior chamber of the nipple shield 340. Negative pressure within the barrel 344 or interior chamber of the nipple shield 340 can cause milk to be expressed from the breast and into the barrel 344 or interior chamber, as described elsewhere herein.

Once milk is disposed within the barrel 344 or interior chamber of the nipple shield 340, the milk may flow through an exit port or opening 346 of the nipple shield 340, through a flow control mechanism 380, and into the interior of the container 234. In this way, nipple shield exit port 346 may operate as an opening for milk release. In some cases, flow control mechanism 380 may be provided as a duckbill valve. Flow control mechanism 380 can operate to prevent the backflow of milk, for example to keep milk from flowing from container 234 into the interior chamber 343 or barrel 344 of the nipple shield 340.

Top container assembly 210 can include a feeding tube connection mechanism 242, which is configured to attach with or otherwise engage a feeding tube 410. In some cases, feeding tube connection mechanism 242 is a valve or a port. Milk may flow out of the container 234 through the feeding tube connection mechanism 242 and into the feeding tube. In some cases, feeding tube connection mechanism 242 is provided as a flexible push-through port or opening for the feeding tube 410. As shown here, a nipple attachment 420 is coupled with a distal end of the feeding tube 410. In this way, milk can flow from the feeding tube 410 through the nipple attachment 420 and to the nursing baby. In some embodiments, a nipple attachment 420 can be shaped to resemble a nipple of a baby bottle.

In some embodiments, one or more features of pump flange mechanism 350 and/or pump flange 360 can operate as a backflow protector.

Figure 9A:
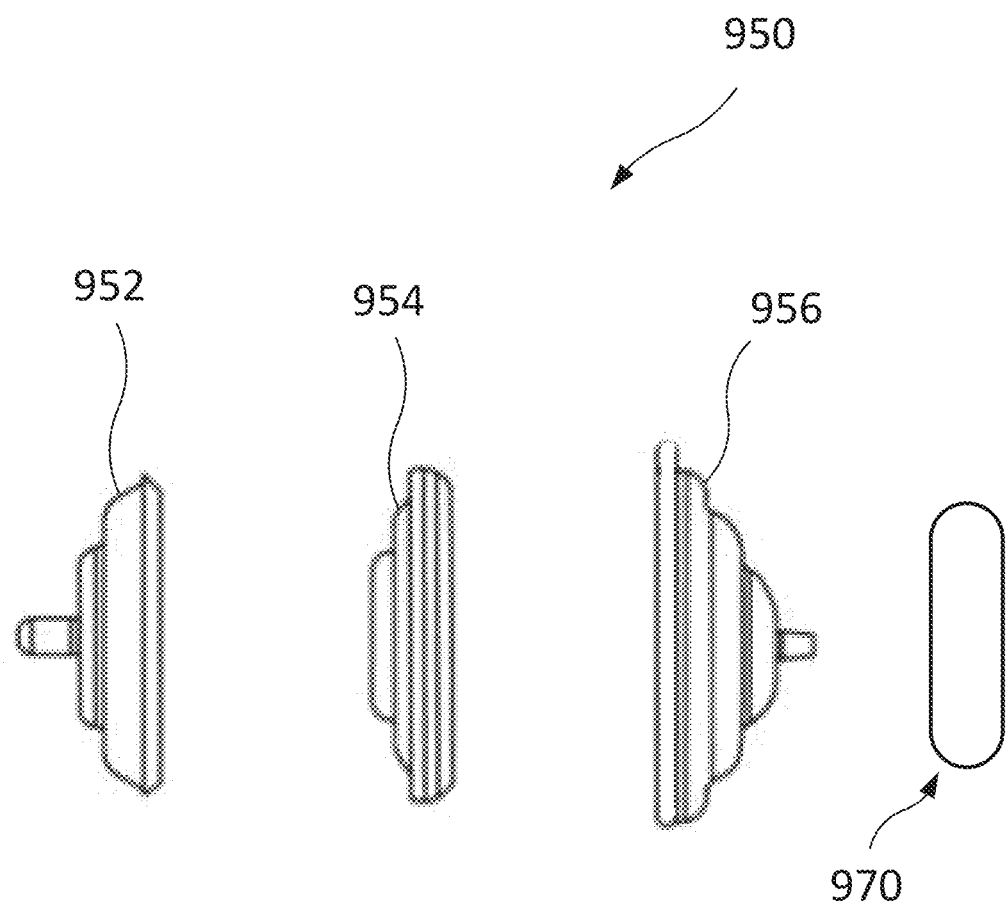
FIG. 9A depicts aspects of a backflow protector for a breastmilk pumping and feeding device, in accordance with some embodiments.

FIG. 9A depicts additional aspects of a backflow protector 950 for a breastmilk pumping and feeding device, according to embodiments of the present invention. Backflow protector includes a small case 952, a diaphragm or membrane 954, and a large case 954. In use, the diaphragm or membrane can be placed in the small case, and the large case can be placed over the diaphragm or membrane, such that a seal is formed between the small case and the large case. In some embodiments, the backflow protector 950 can be referred to as a clamshell valve or pump flange valve. The backflow protector can operate to ensure that vapor or unwanted fluid does not reach the pump internals. As further discussed elsewhere herein, a clamshell may be integrated into the body of the pump. The backflow protector 950 can operate to provide a barrier (e.g. which may also be referred to as a media separation) between a pump 970 and the expressed breastmilk. Relatedly, the backflow protector 950 can prevent breastmilk from reaching the pump and help to ensure that the expressed breastmilk remains uncontaminated. Hence, the breastmilk can flow into the protector 950 and remain between the small case 952 and the diaphragm or membrane 954, without passing through the diaphragm or membrane 954 and into the space between the diaphragm or membrane 954 and the large case 956. In some cases, one or more features of the backflow protector 950 (or optionally, one or more features of the pump flange mechanism 350 and/or pump flange 360 shown in FIG. 9) can be referred to as a flexible clamshell, or a clamshell funnel and tube mechanism. In some cases, a clamshell may not be present. In some cases, a cavity may be present in the pump, and may be equivalent to a clamshell.

Figure 10:
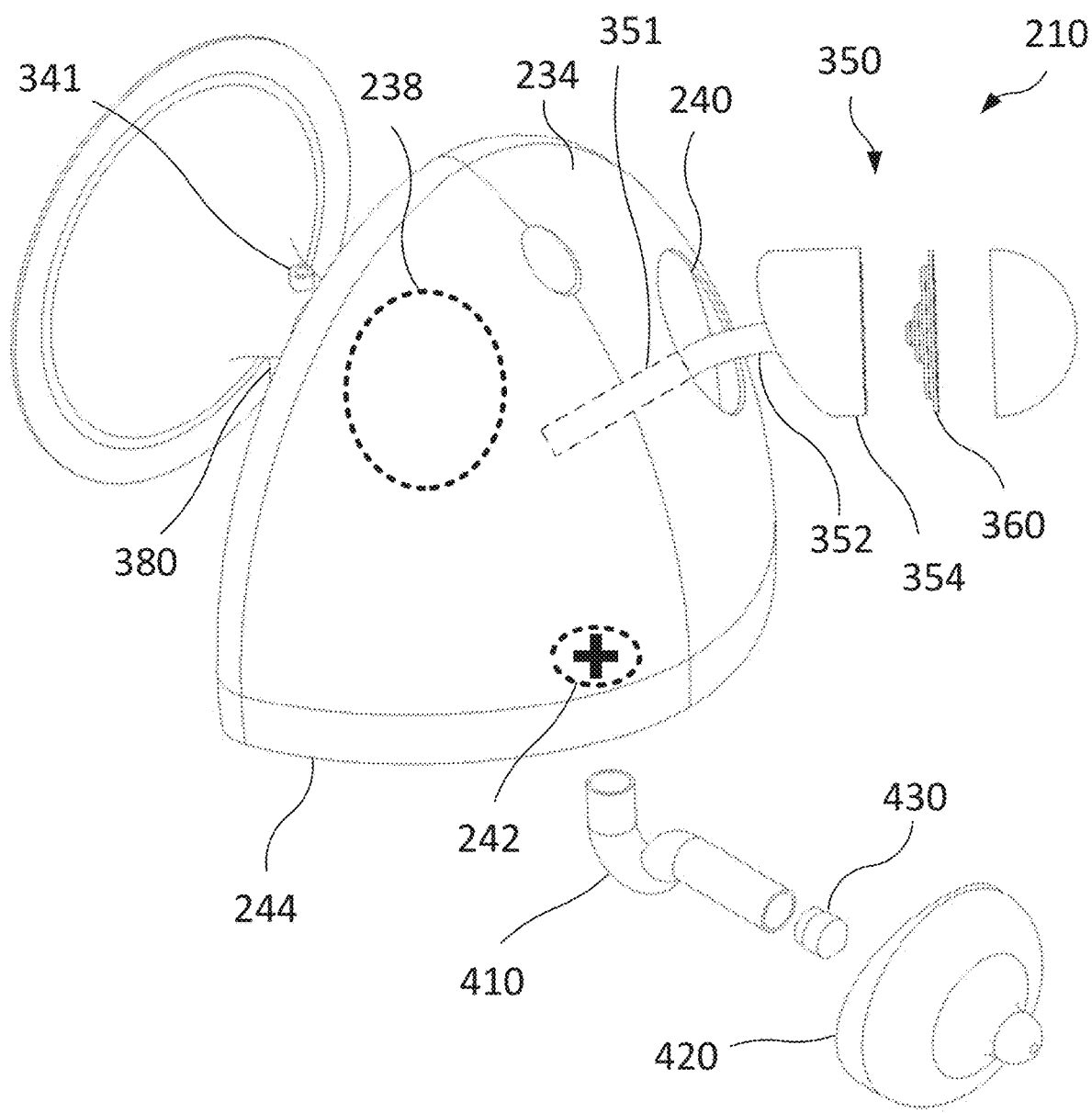
FIG. 10 shows an exploded view of upper components of a breastmilk pumping and feeding device, in accordance with some embodiments.

FIG. 10 depicts additional aspects of a breastmilk pumping and feeding device, which includes a top container assembly 210, a pump flange mechanism 350 having a pump flange tube 352 and a pump flange housing 354, and a pump flange 360.

The top container assembly 210 has a container 234 (e.g. a clear milk container), a nipple shield opening or aperture 238 (e.g. into which the nipple shield may snap in to, or otherwise engage or attach), and a negative pressure port 240 that is configured to engage a source of or conduit with a negative pressure source. In some cases, a nipple shield includes an engagement rim or snap-on rim, which couples with the nipple shield opening 238 of the container 234 (e.g. when the barrel of the nipple shield is positioned within the interior of container 234). A nipple shield may also include or be in fluid communication with a nipple shield negative pressure port 341, which in turn engages with a distal end 351 of the pump flange tube 352. For example, nipple shield negative pressure port 341 may be in fluid communication with distal end 351 of the pump flange tube, when the port and the distal end 351 are both disposed within the interior of the container 234. In some cases, nipple shield negative pressure port 341 may be referred to as a port for a pump flange tube, or a pump flange port.

The container negative pressure port 240 can be configured to engage the pump flange housing 354 of the pump flange mechanism 350. In some cases, the container negative pressure port 240 and the pump flange housing 354 are configured to couple in a snap-on fashion. In some cases, the pump flange housing 354 is provided as a solid component. The pump flange 360 can be flexible, and can operate to prevent milk from entering the pump or a negative pressure source. In some cases, the negative pressure source can operate to provide negative pressure to the barrel or interior chamber of the nipple shield (e.g. via nipple shield negative pressure port 341). Negative pressure within the barrel or interior chamber of the nipple shield can cause milk to be expressed from the breast and into the barrel or interior chamber, as described elsewhere herein.

Once milk is disposed within the barrel or interior chamber of the nipple shield, the milk may flow through an exit port or opening of the nipple shield, through a flow control mechanism, and into the interior of the container 234. In this way, nipple shield exit port may operate as an opening for milk release. In some cases, from the barrel or interior chamber, milk may exit the nipple shield and pass through a flow control mechanism 380, and into the interior of the container 234. In some cases, the flow control mechanism 380 is provided as a duckbill valve.

Top container assembly 210 can include a feeding tube connection mechanism 242, which is configured to attach with or otherwise engage a feeding tube 410. In some cases, feeding tube connection mechanism 242 is a valve or a port. Milk may flow out of the container 234 through the feeding tube connection mechanism 242 and into the feeding tube 410. In some cases, feeding tube connection mechanism 242 is provided as a flexible push-through port or opening for the feeding tube 410. As shown here, a nipple attachment 420 is coupled with a distal end of the feeding tube 410. In this way, milk can flow from the feeding tube 410 through the nipple attachment 420 and to the nursing baby. The device may also include a flow control mechanism 430 disposed between the feeding tube 410 and the nipple attachment 420. The flow control mechanism 430 can be in fluid communication with both the feeding tube 410 and the nipple attachment 420, and can regulate fluid flow therebetween. In some cases, flow control mechanism 430 is provided as a one way valve (e.g. so that milk can flow from feeding tube 410 to nipple attachment 420, but not from nipple attachment 420 to feeding tube 410).

Top container assembly 210 may also have a bottom surface 244 that is flat, so that the top container assembly 210 will remain stable when placed or rested on a surface, such as a flat surface, for example when the top container assembly 210 is disengaged or separated from the bottom housing assembly.

Figure 11:
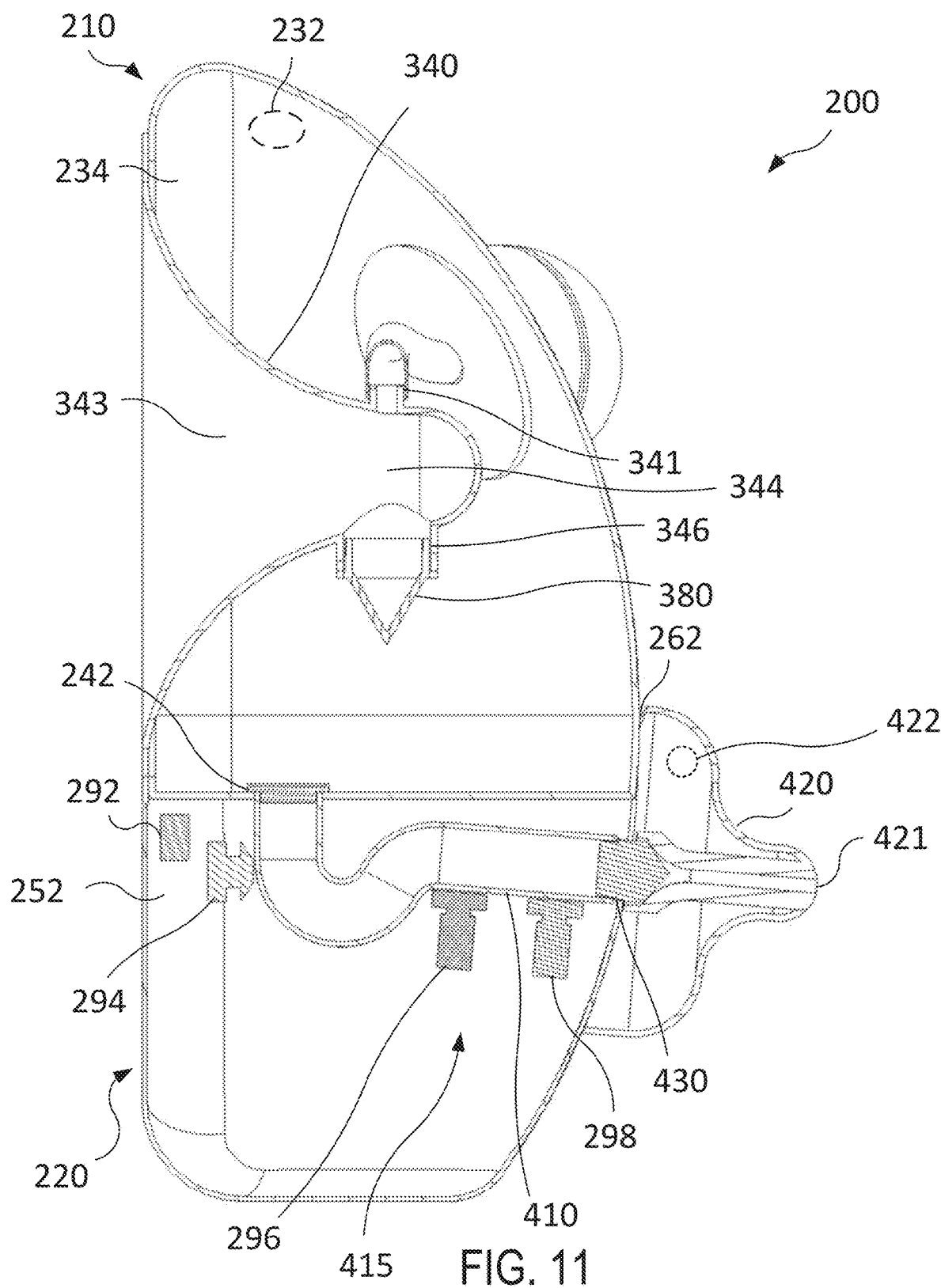
FIG. 11 illustrates aspects of a breastmilk pumping and feeding device, in accordance with some embodiments.

FIG. 11 depicts additional aspects of a breastmilk pumping and feeding device 200, which includes a top container assembly 210, a nipple shield 340, and a bottom housing assembly 220. The top container assembly 210 has a container 234 (e.g. a clear milk container), a nipple shield opening or aperture into which the nipple shield 340 may snap in to, or otherwise engage or attach, and a negative pressure port that is configured to engage a source of or conduit with a negative pressure source. In some cases, nipple shield 340 includes an engagement rim or snap-on rim, which couples with the nipple shield opening of the container 234 (e.g. when the barrel 344 of the nipple shield 340 is positioned within the interior of container 234). Nipple shield 340 may also include or be in fluid communication with a nipple shield negative pressure port 341, which in turn engages with a distal end of the pump flange tube. For example, nipple shield negative pressure port 341 may be in fluid communication with distal end of the pump flange tube, when the port 341 and the distal end are both disposed within the interior of the container 234. In some cases, nipple shield negative pressure port 341 may be referred to as a vacuum suction port for a pump flange tube. Bottom housing assembly 220 can include an electronics housing 252, which may also be referred to as a hub.

In some cases, a negative pressure source can operate to provide negative pressure to the barrel 344 or interior chamber of the nipple shield 340. Negative pressure within the barrel 344 or interior chamber of the nipple shield 340 can cause milk to be expressed from the breast and into the barrel 344 or interior chamber, as described elsewhere herein.

Once milk is disposed within the barrel 344 or interior chamber of the nipple shield 340, the milk may flow through an exit port or opening 346 of the nipple shield 340, through a flow control mechanism 380, and into the interior of the container 234. In this way, nipple shield exit port 346 may operate as an opening for milk release. In some cases, flow control mechanism 380 may be provided as a duckbill valve. In some cases, flow control mechanism 380 may be provided as a one-way valve. Flow control mechanism 380 can operate to prevent the backflow of milk, for example to keep milk from flowing from container 234 into the interior chamber 343 or barrel 344 of the nipple shield 340.

Top container assembly 210 can include a feeding tube connection mechanism 242, which is configured to attach with or otherwise engage a feeding tube 410. In some cases, feeding tube connection mechanism 242 is a valve or a port. Milk may flow out of the container 234 through the feeding tube connection mechanism 242 and into the feeding tube 410. In some cases, feeding tube connection mechanism 242 is provided as a flexible push-through port or opening for the feeding tube 410. As shown here, a nipple attachment 420 is coupled with a distal end of the feeding tube 410. In this way, milk can flow from the feeding tube 410 through the nipple attachment 420 and to the nursing baby (e.g. via a distal exit port or aperture 421 of the nipple attachment 420). In some cases, the device 200 may include a flow control mechanism 430 in fluid communication with and disposed between the feeding tube 410 and the nipple attachment 420. The flow control mechanism 430 can regulate fluid flow between the feeding tube 410 and the nipple attachment 420. In some cases, flow control mechanism 430 is provided as a one-way flow valve (e.g. so that milk can flow from feeding tube 410 to nipple attachment 420, but not from nipple attachment 420 to feeding tube 410). In some cases, flow control mechanism 430 is provided as a duckbill valve.

The bottom housing assembly 220 can include a first sensor 292, which may be a priming sensor. The bottom housing assembly 220 can also include an electronic solenoid valve or gate 294, a second sensor 296 or "full sensor", and a third sensor 298 or "empty sensor".

In the embodiment depicted here, the device 200 is configured so that the milk container 234 can sit or be positioned around the breast of the user. Further, the device 200 can be configured to allow all of the milk which the mother pumps to be available to the baby, so that excess milk from one point of the session does not become unavailable if the baby changes her rate of drinking or outpaces the pump during the session. The device 200 provides a simple design having few compartments and pieces for assembly and cleaning. During operation, as the milk container 234 is filled, milk within the container is disposed generally around the breast and high enough so all the milk can exit the bottom of the container 234 (e.g. via feeding tube connection mechanism 242) and to the baby's mouth (e.g. via nipple attachment 420), thus allowing for the container 234 to act both as the milk storage compartment and the feeding source.

The device 200 also provides visibility of the nipple during pumping. The clear plastic container 234 allows the mother to look down at her breast and nipple and see whether the nipple is being suctioned directly through the barrel 344 of the nipple shield 340, or whether it is being pulled to the sides, which can cause suboptimal milk flow. The device 200 also allows the mother to see whether flow has started and how much milk is flowing (sometimes sprays will come out of a dozen streams, sometimes just one or two). Knowing this gives the mother a sense of whether to reposition or turn the suction up or down (e.g. using an increase vacuum button 256 or a decrease vacuum button 258 as depicted in FIGS. 8A and 8B) to get the best flow of milk.

According to some embodiments, the device 200 includes two assemblies, a clear top container or top container assembly 210 that interfaces with the breast (e.g. via nipple shield 340) and a bottom housing or bottom housing assembly 220 that contains the electronics for counting and providing suction to the breast (pumping). The bottom housing assembly 220 can include an electronics housing 252. The clear top milk container or top container assembly 210 can snap down into the bottom housing assembly 220 or electronics housing 252.

The milk container 234 can be provided as a clear plastic container that interfaces with the breast (e.g. via nipple shield 340) and catches the milk that is vacuum suctioned from the breast. With regard to the milk pathway, the milk leaves the nipple and is expressed into the interior chamber 343 and/or barrel 344 of the nipple shield, and empties downward from the nipple shield 340 into the container 234 through a flow control mechanism 380, which may be provided as a duckbill, one-way, valve. Although the pumped milk may not touch the breast, as the milk fills the container 234, it occupies the physical space around the breast. When the milk fills the container 234 up to a certain level, for example 1 oz, a first sensor 292, which may be an infrared "priming" sensor, which faces the lower planes of the milk container 234, can trigger an indicator (e.g. light or beep) that indicates milk is ready for the baby to drink. In some cases, the milk level within the container 234 which triggers the indicator has a value within a range from about 0.03 oz to about 1.75 oz.

At that time, a "feed baby" button or "let down" to baby button 260 as illustrated in FIGS. 8A and 8B can be pressed, to allow milk to flow through the flexible, clear tubing 410, and towards the baby nipple 420. The baby nipple 420, which the infant sucks from, can include a non-leaking air vent 422, and a flow control mechanism 430 (e.g. an internal one-way flow duckbill valve) to prevent backflow to the milk in the milk container 234. Alternatively, with reference to FIG. 14, a venting valve may be provided at another location along the flexible tubing, in a format such as a one way y-valve, so air can be drawn into the tubing so the infant does not have to resist against the vacuum of the straw chamber in order to drink.

With returning reference to FIG. 11, the milk capacity of the container 234 can be about 8 oz. In some cases, the milk capacity of the container 234 can have a value within a range from about 4 oz to about 10 oz. In some cases, the container 234 can have one or more volume markings (e.g. such as the volume markings 32 depicted in FIG. 3). In some cases, the volume markings can provide indicia of fluid increments (e.g. 1 oz increments). In some cases, the container 234 can be made available in a range of different sizes or volume capacities, and the range can be made available in increments, for example 1 oz increments. In some embodiments, the container 234 can include a pour spout having a vent hole or aperture 232. As shown here, hole 232 can be positioned toward the top of the container 234. In some cases, the hole 232 is a sealable hole. The hole 232 can be opened to pour the milk out of the container 234 and into another container, bottle, milk storage bag, or the like. The sealable hole 232 may also feature a small vent hole, that remains open at all times or remains optionally open (e.g. can be put in an open or close position) in order to allow air to leave the container 234 as the milk is entering the container 234 and replacing the air.

When feeding and/or pumping additional milk is complete, the feed baby button (e.g. button 260 depicted in FIGS. 8A and 8B on the bottom assembly) can be pressed again to stop milk flow to the nipple and the pump power button (e.g. button 254 depicted in FIGS. 8A and 8B) can be pressed to stop the negative pressure. The baby can be moved from the device 200, the device 200 can be removed from the breast, and the clear milk container apparatus or top container assembly 210 can be separated from the bottom housing assembly 220.

With continuing reference to FIG. 11, the breastmilk pumping and feeding device 200 is also configured for convenient disassembly. For example, the top container assembly 210 can be uncoupled or separated from the bottom housing assembly 220. In some cases, such separation can be achieved by pulling the top container assembly 210 and the bottom housing assembly 220 apart from one another. Because bottom housing assembly 220 can also include a slit 262 (see also FIGS. 8A and 8B) that is configured to receive a feeding tube 410 and/or nipple attachment 420, when the top container assembly 210 and the bottom housing assembly 220 are separated apart from one another, the bottle nipple attachment 420 and tubing assembly 415 (which may include tubing 410 and flow control mechanism 430) can be moved out of the slit 262 in an upward direction relative to the bottom housing assembly 220. As further discussed elsewhere herein, in some cases a bottom housing may not have a slit. In some cases, a bottom housing may have a cavity instead of a slit. In some cases, the baby nipple attachment 420 and tube assembly 415 can be detached from the bottom of the bottom housing assembly 220 for washing (e.g. by removing tube 410 from feeding tube connection mechanism 242) and the flexible rubber hole it poked through pinches back on itself to make a seal.

As further discussed elsewhere herein, in some embodiments a peristaltic mechanism can be provided that compresses certain aspects of the tube assembly 415, for example the feeding tube 410, so that the flow of milk is facilitated to the nipple attachment 420, thus allowing the baby to drink. In some embodiments, sensors 296 and/or 298 can operate to detect whether milk is present, indicating to the mother or user that the device is ready to provide milk to the baby. In some embodiments, tube assembly 415 can provide an assembly through which milk can pass through a dosing tube which is connected to a priming chamber. In some embodiments, breast interfacing nipple shield 340 can provide a breast flange through which breastmilk can be pumped.

Figure 11A:
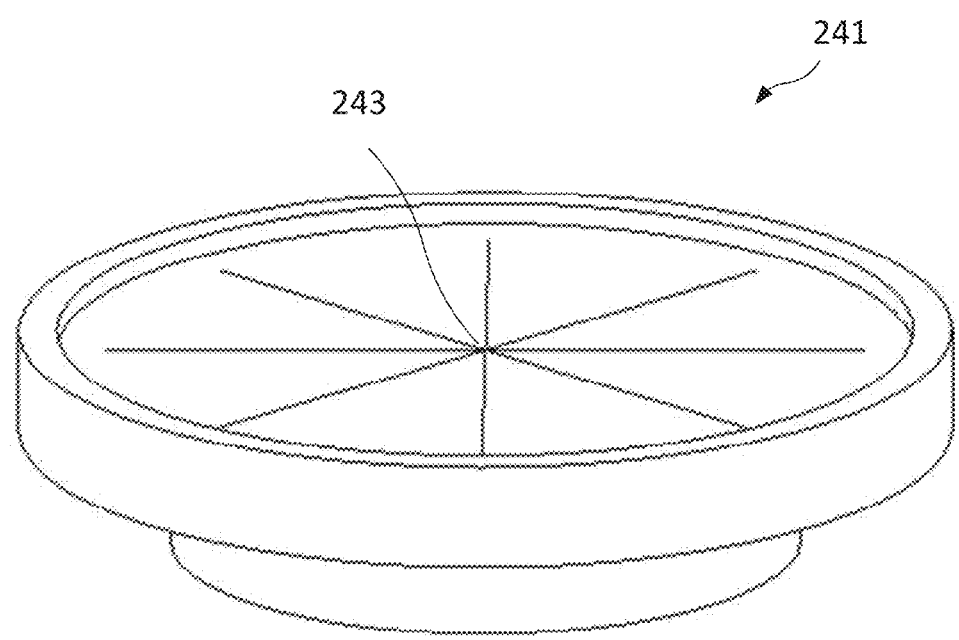
FIG. 11A depicts aspects of a grommet mechanism of a breastmilk pumping and feeding device, in accordance with some embodiments.

FIG. 11A illustrates aspects of an exemplary grommet mechanism 241 that can optionally be used in conjunction with or as part of a feeding tube connection mechanism. As shown here, grommet mechanism 241 includes an aperture or hole 243, which can be configured to receive a feeding tube. When the feeding tube is inserted through the aperture 243, the sides or edges of the aperture 243 can flex and form a seal with the tube. When the tube is removed or not positioned within the aperture 243, the sides or edges of the aperture can effectively form a seal that prevents or inhibits the flow or movement of fluid through the aperture. In some cases, a grommet mechanism 241 can be provided as a rubber grommet. In some cases, the grommet mechanism 241 provides a self-pinching seal having a push through opening 243 that is configured to receive a feeding tube. The grommet mechanism 241 can be positioned within a bottom or lower hole of a container, or otherwise through a bottom or lower side of a container.

With returning reference to FIG. 11, The clear plastic container 234 can then be set down on a surface or the top rubber pour spout 232 can be opened and milk transferred out of the container 234 and into another receptacle or destination. Once milk is transferred out of the container 234, the negative pressure parts, such as a flexible clamshell and/or clamshell funnel/tube (which may include one or more features of the pump flange mechanism 350 and/or pump flange 360 shown in FIG. 9 or one or more features of the backflow protector 950 of FIG. 9A) can be removed for washing. The breast interfacing nipple shield 340 can then be separated from the back of the milk container 234, and the flow control mechanism or duckbill valve 380 removed, both for washing.

The breastmilk pumping and feeding device 200 may also include a counting mechanism, for example which may be disposed within the bottom housing assembly 220. In some cases, the counting mechanism may include one or more sensors (e.g. sensors 61, 75, and/or 76 depicted in FIGS. 4 and 5 or sensors 296 and/or 298 depicted in FIG. 11) configured to quantify breastmilk displaced to the baby. In some cases, such sensors may be infrared sensors. In some cases, the breastmilk consumed by the baby may be quantified by a series of incorporated sensors (e.g. sensors 61, 75, and/or 76 depicted in FIGS. 4 and 5 or sensors 296 and/or 298 depicted in FIG. 11) that indicate whether a preliminary breastmilk receptacle (e.g. priming chamber 60 depicted in FIGS. 4 and 5) or dosing tube (e.g. tube 70 depicted in FIGS. 4 and 5 or tube 410 depicted in FIGS. 9, 10, and 11) of defined volume is full or empty. The sensors may trigger the receptacle or dosing tube to allow more breastmilk to fill in when empty and gate off breastmilk when full. A count of how many times the defined volume is filled may provide the live quantification of breastmilk consumption. In some cases, the defined volume may range from about 0.1 mL to about 15 mL.

In the embodiment depicted in FIG. 11, a significant portion of the feeding tube 410 is configured to be disposed in a horizontal orientation when the device is in operation.

Without being bound by any particular theory, it is believed that the surface tension on the limited inner diameter (ID) of the tube 410 that interfaces with the sensors can provide an amount of flow force or motion, such that gravity is not needed in order for milk to flow into the tube 410. As mentioned elsewhere herein, a physical sensor for identifying the presence of milk can be an infrared sensor (e.g. identifying the physical color difference caused by the milk) or the sensor can be a capacitance sensor (e.g. identifying the proximity of liquid).

In some cases, a capacitance sensor of the system can be configured to detect a feeding fluid amount present in the chamber. In some cases, capacitance can be used to measure pre-chamber fullness and emptiness and signal additional fluid to come into chamber.

In some cases, a breastmilk pumping and feeding device may not include a counting mechanism. For example, a breastmilk pumping and feeding device without a counting mechanism can be configured to allow a baby to continuously drink so only a small amount of storage would be required. In some cases, a breastmilk pumping and feeding device without a counting mechanism can be configured to allow for a smaller frame.

In some cases, a breastmilk pumping and feeding device may not include a storage container, or may include a small storage container. For example, a breastmilk pumping and feeding device can be provided in a smaller configuration that includes a storage container that only has 1-3 oz of milk, just enough to constantly provide a primed amount for the infant to drink. In some cases, such a device can include a counting mechanism and an external pump, so that the main intention is for direct feeding and counting of the milk consumed by the baby. The pump could additionally stop pumping once maximum capacity has been reached, by sensing fullness via infrared or capacitance, and then shut off and turn back on when reaching below another threshold.

A breastmilk pumping and feeding device 200 can be configured to provide a vacuum pathway which facilitates the flow of milk. In some cases, a housing of the device may contain a pump mechanism or negative pressure source. For example, a pump mechanism may include a motor. The pump mechanism can operate to provide negative pressure to a clamshell flexible valve that fits over a hard clamshell feature at the side of the milk container. This flexible valve can operate to ensure that milk, condensation, or other moisture from the milk container 234 is not drawn into the electronics housing 252. In some cases, the flexible valve can be drawn towards the electronics housing 252, and provide the volume of negative pressure through the hard, matching clamshell piece and tube that routes to the central nipple shield 340, needed to draw milk from the breast. The location of the suction source at the clear top container 234 could be located in various locations, such as the sides, back or lower regions of the container 234. In some cases, it is desirable to have the nipple shield negative pressure port 341 at the nipple shield 340, which interfaces with the vacuum, to be positioned at the top half of the container 234, so as not to draw in excess milk, and perhaps contains a shielding feature so milk does not spray directly into the port 341. Plus (+) and minus (−) buttons (see e.g. FIGS. 8A and 8B) on the housing can be pressed to increase or decrease the suction, which is met with an increasing or decreasing tone. When the tone stops despite pressing the button, the maximum or minimum suction has been reached. In some cases, a breastmilk pumping and feeding device may not include a built-in pump, which may reduce the cost of the device. Such embodiments may also not include pumping software incorporated in the bottom housing. In some cases, a breastmilk pumping and feeding device can be configured for use with an off-the-shelf pump. For example, the device may include an external pumping port on the clear container 234, with mating pieces that interface tubing of various market pumps, so that the suction can be provided by any pump a mother has on hand.

Figure 12A:
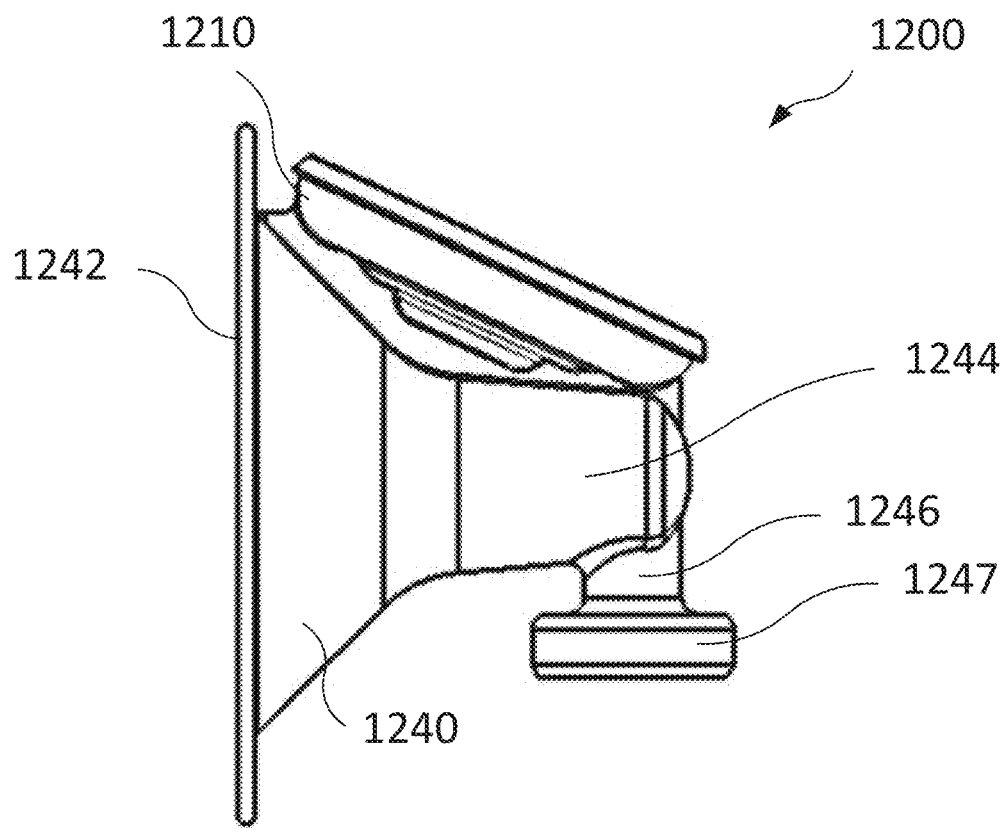
FIGS. 12A to 12D depict aspects of a nipple shield and related components of a breastmilk pumping and feeding device, in accordance with some embodiments.
Figure 12B:
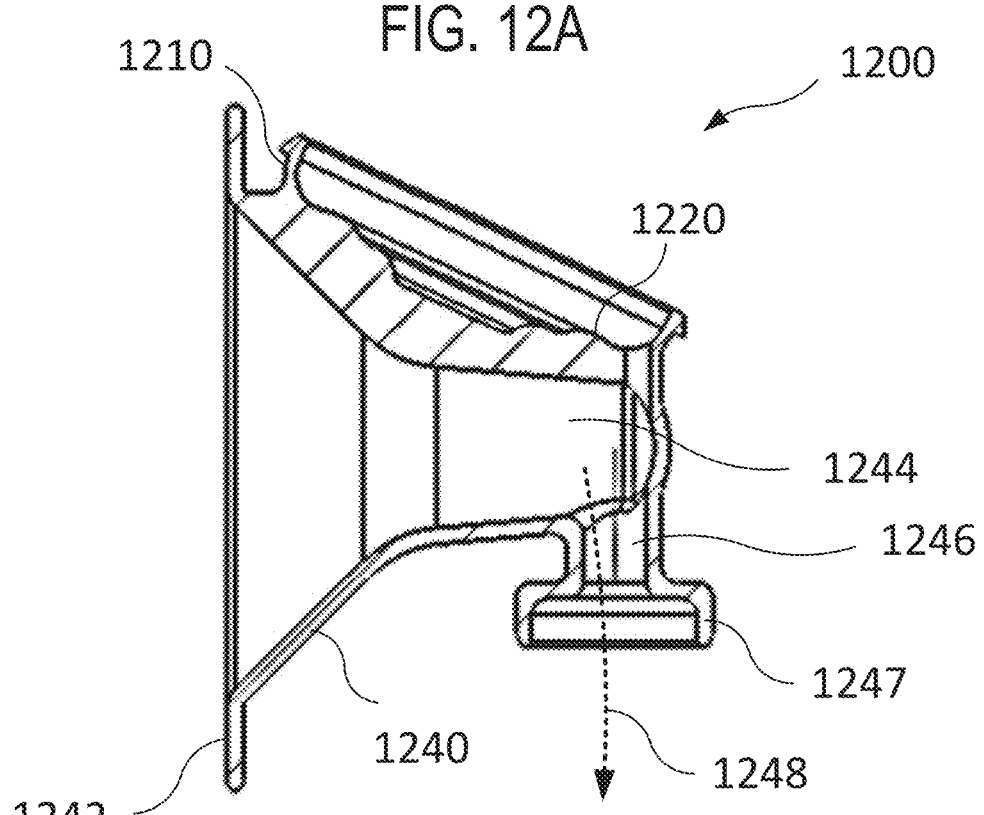

The side view of FIG. 12A and the cross-section view of FIG. 12B depict aspects of a proximal pump flange assembly 1200 of a breastmilk pumping and feeding device. The proximal pump flange assembly 1200 can be coupled with or used in conjunction with a nipple shield 1240. The proximal pump flange assembly 1200 can operate to mediate suction to the breast and can be attached to or located adjacent to the nipple shield 1240. As shown here, proximal pump flange assembly 1200 includes a pump flange housing 1210 and an interior pump flange 1220. In some cases, pump flange housing 1210 is a solid pump flange housing. In some cases, interior pump flange 1220 is a flexible interior pump flange. Nipple shield 1240 includes a rim 1242 that is configured to engage with a nipple shield opening or aperture of a container, such as a clear milk container. In some cases, rim 1242 engages the container in a snap-on connection. Aspects of the coupling between a nipple shield and a container can be further understood with reference to FIG. 9. Proximal pump flange assembly 1200 can be configured for operative fluid association with a negative pressure source. In some cases, proximal pump flange assembly 1200 can include one or more features of a backflow protector (e.g. as shown in FIG. 9A). In this sense, aspects of the proximal pump flange assembly can operate as a diaphragm valve, and help in facilitating the administration of negative pressure to the user.

Milk disposed within a barrel 1244 or interior chamber of the nipple shield 1240 can exit or flow through an exit port or opening 1246 of the nipple shield 1240, as indicated by milk release pathway 1248. In this sense, exit port 1246 provides an opening for milk release from the nipple shield. As shown here, exit port 1246 can include a rim 1247. In some cases, rim 1247 is configured for releasable attachment with a duckbill valve or other flow control mechanism. The duckbill valve or other flow control mechanism (see, e.g., element 380 in FIG. 11) can operate to prevent backflow into the pump suction.

Figure 12C:
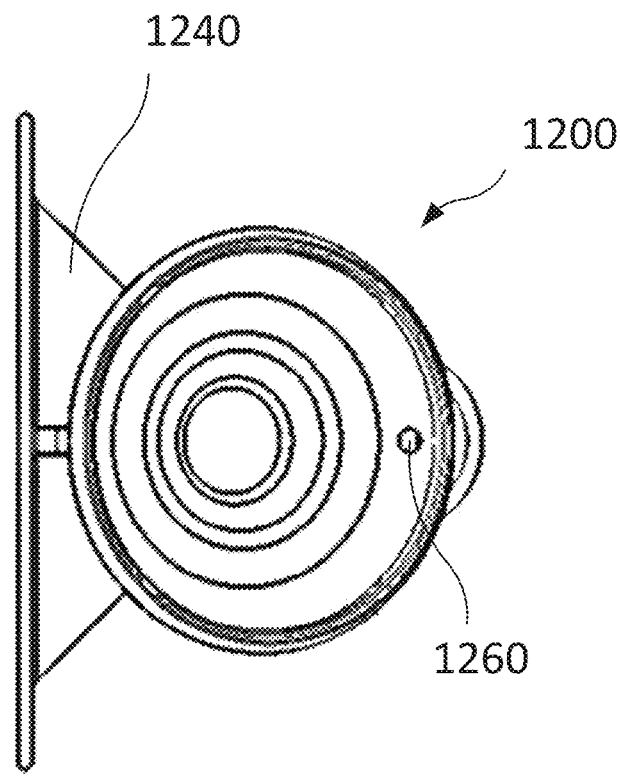
Figure 12D:
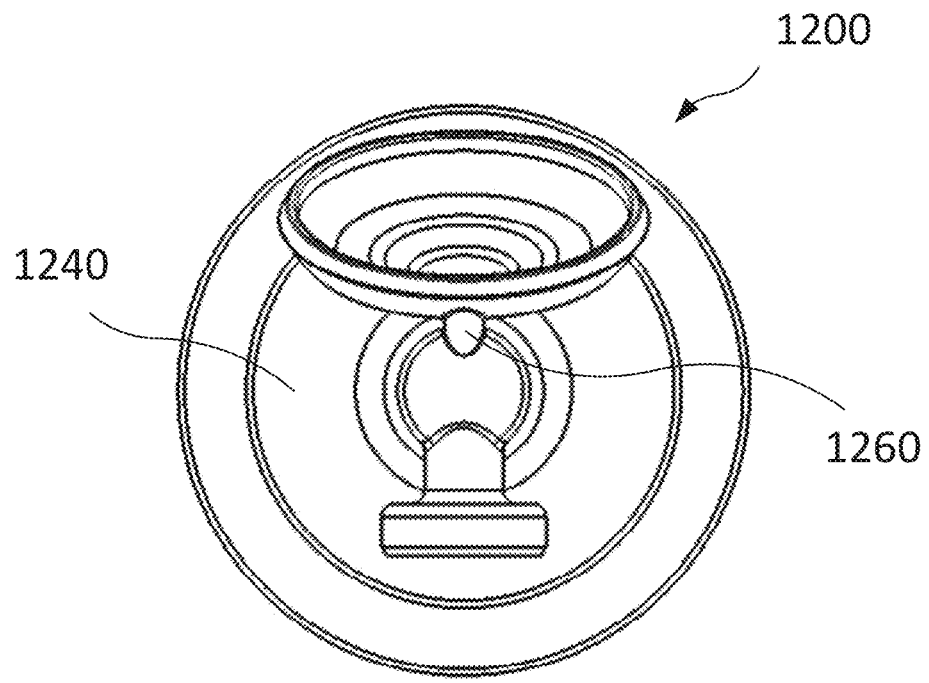

The top view of FIG. 12C and the front view of FIG. 12D depict additional aspects of a proximal pump flange assembly 1200 of a breastmilk pumping and feeding device. As shown here, proximal pump flange assembly 1200 includes a vacuum transfer pathway 1260 to the nipple.

Figure 13A:
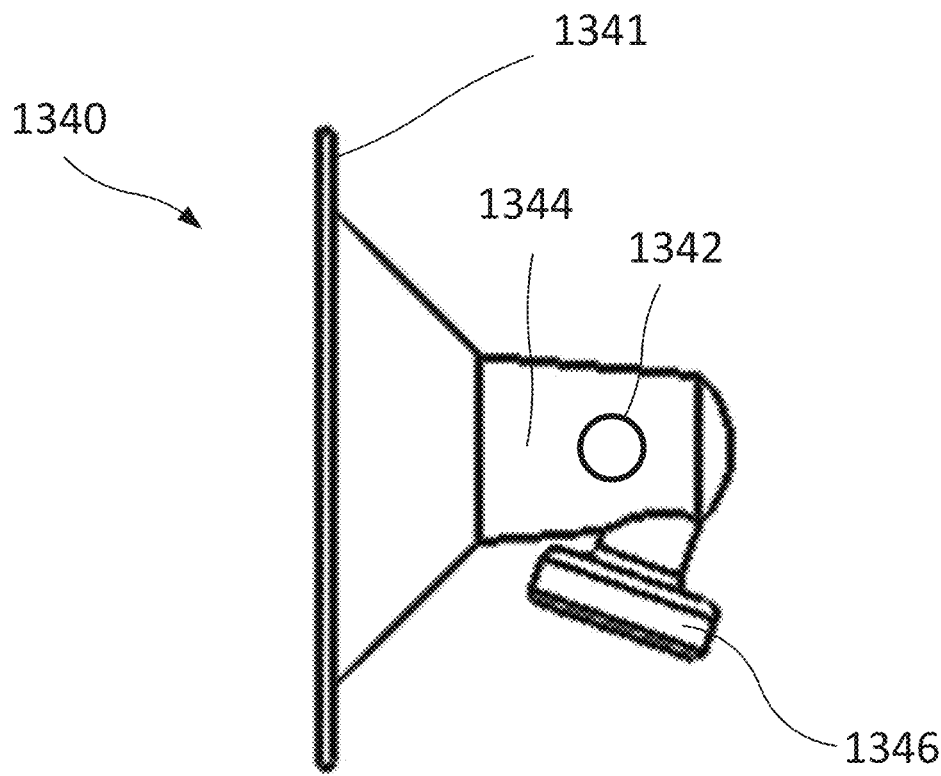
FIGS. 13A and 13B depict aspects of a nipple shield and related components of a breastmilk pumping and feeding device, in accordance with some embodiments.
Figure 13B:
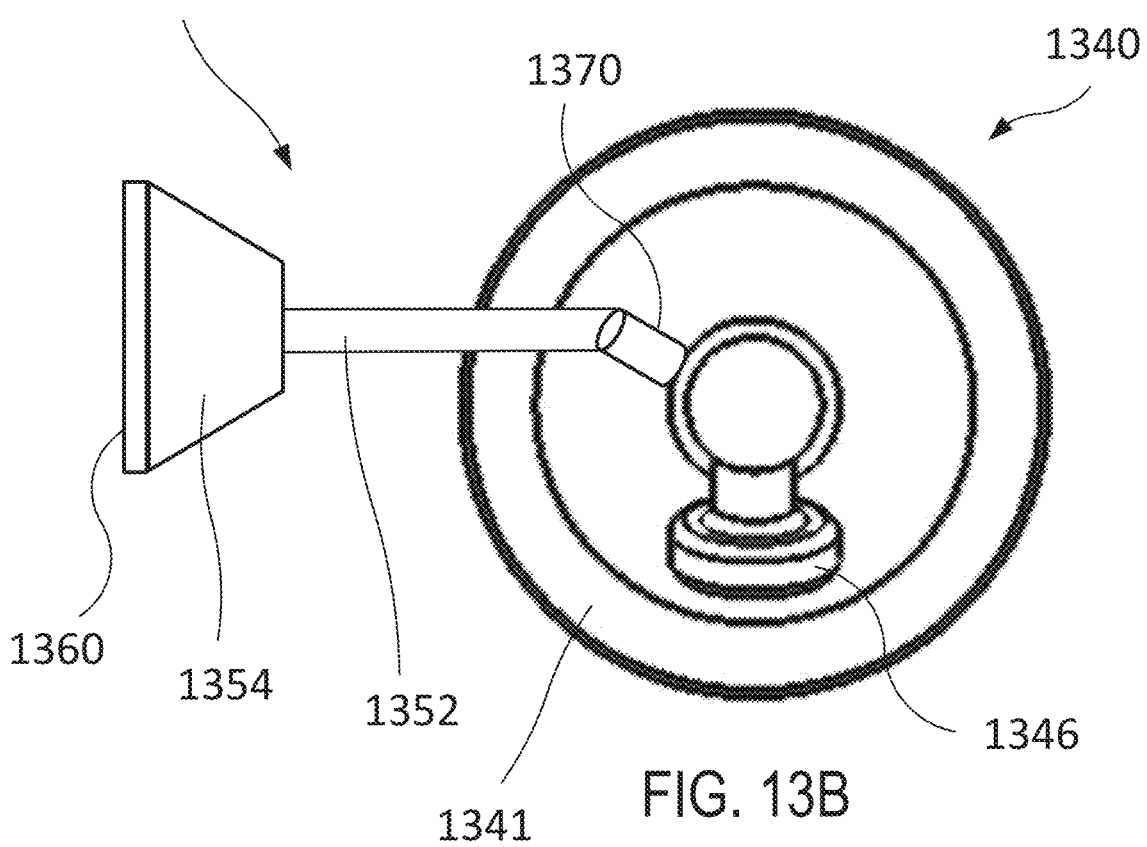

The side view of FIG. 13A and the front view of FIG. 13B depict aspects of a nipple shield or breast flange 1340 and distal pump flange mechanism 1350, according to embodiments of the present invention. Nipple shield 1340 can include a rim 1341 (e.g. a milk container interfacing rim) that is configured to engage with a nipple shield opening or aperture of a container, such as a clear milk container. As shown here, distal pump flange mechanism 1350 can include a pump flange tube 1352, a pump flange housing 1354, and a pump flange 1360. In some cases, the pump flange 1360 can be a flexible pump flange. The pump flange 1360 can interface with a pump housing. Nipple shield 1340 can include a vacuum hole or aperture 1342, and a tube 1370 can provide fluid communication between the pump flange tube 1352 and the aperture or port 1342 via the tube 1370. As shown here, the aperture 1342, tube 1370, and distal pump flange mechanism 1350 are generally disposed toward the side of the nipple shield 1340, rather than toward the top of the nipple shield. In this way, the attachment between the nipple shield 1340 and the pump flange mechanism 1350 does not obscure the view of the nipple by the mother during pumping. It can be helpful for the mother to view the nipple within the nipple shield 1340, to confirm whether the nipple and/or milk is positioned or moving straight down the nipple shield barrel 1344 (e.g. for maximum flow), and/or to confirm flow and successful removal of milk or colostrum. Hence, the location of the port 1342 can be positioned so that the pump flange tube which leads to the pump flange housing is located toward the side, back, or other location where it does not obscure the user's view of the nipple. As discussed elsewhere herein, a nipple shield 1340 can include an exit opening 1346 for milk release. In some cases, the exit opening 1346 can attach with a duckbill valve or other flow control mechanism. As shown here, exit opening or port 1346 is tilted slightly backward toward the user, so as to minimize the depth of the breastmilk pumping and feeding device. In some cases, the opening or port 1346 may be smaller, and not tilted (e.g. extend straight downward from barrel 1344).

Hence, a nipple shield may have a connection point or port for a one way valve such as a duckbill valve, such that the port is oriented straight down (as shown in FIGS. 12A and 12B) or at an angle (as shown in FIG. 13A). The angled version may allow for a smaller frame.

As shown in FIGS. 12C and 12D, the nipple shield 1240 may also have a vacuum port (e.g. with a vapor barrier included) that is in fluid communication with the vacuum transfer pathway 1260. Here, the vapor barrier is at a superior position in relation to the anterior end of the nipple shield. As shown in FIG. 13A, the nipple shield 1340 may also have a vacuum port 1342 with a vapor barrier included. Here, the vapor barrier is at a lateral position in relation to the anterior end of the nipple shield. In some cases, the location of the vapor barrier could be anterior in relation to the anterior end of the nipple shield. In some cases, nipple shield 1340 can include or be in operative association with one or more features of a backflow protector (e.g. as shown in FIG. 9A). In this sense, aspects of the nipple shield can operate as or in concert with a diaphragm valve, and help in facilitating the administration of negative pressure to the user.

Figure 14A:
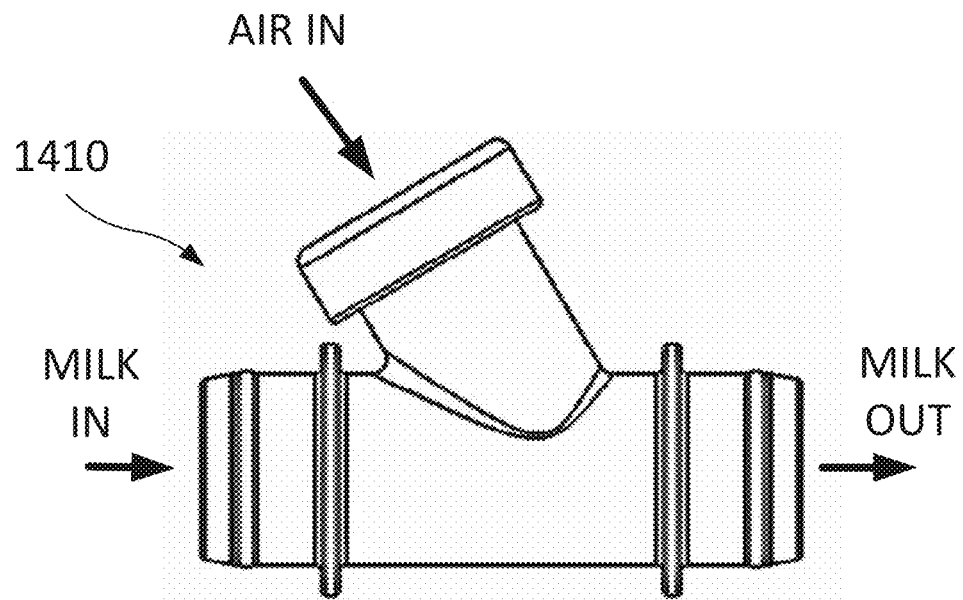
FIGS. 14A and 14B depict aspects of a venting valve of a breastmilk pumping and feeding device, in accordance with some embodiments.
Figure 14B:
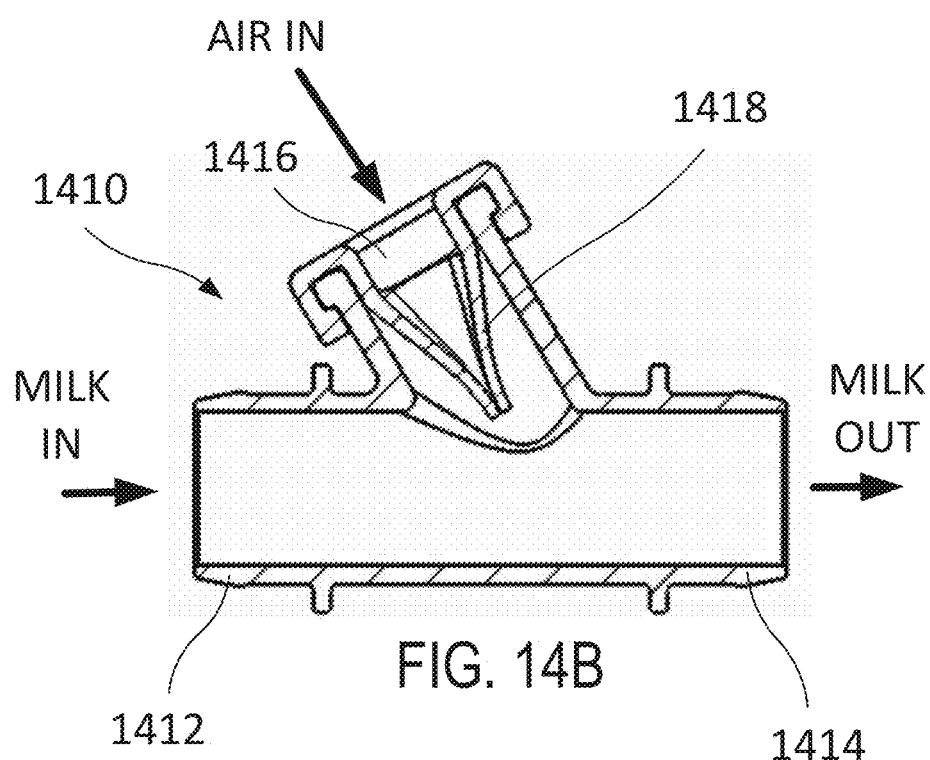

As shown in FIGS. 9, 10, and 11, a breastmilk pumping and feeding device may include a feeding tube or tubing 410 through which milk may flow to the nursing baby (e.g. via nipple attachment 420). In some cases, a venting valve may be provided at a location along the flexible tubing or feeding tube 410, in a format such as a one way y-valve, whereby air can be drawn into the tubing 410 so that the infant does not have to resist against the vacuum of the straw chamber in order to drink. The side view of FIG. 14A and the cross-section view of FIG. 14B depict aspects of an exemplary venting valve 1410 according to embodiments of the present invention. In some cases, a venting valve may be located on the tube 410 after the container and first solenoid valve (e.g. electronic solenoid valve or gate 294 depicted in FIG. 11) and can introduce air into the system so that the milk can drain from the tube 410. In some cases, the tube 410 may be collapsible. In some cases, the tube 410 may include, operate as, or be in operative association with a collapsible counting mechanism. Milk may go in one end of a venting valve 1410 and out the other as shown in FIGS. 14A and 14B. According to some embodiments, if the solenoid does not allow the milk to flow in and there is a vacuum in the line, air is introduced to allow the milk to flow out of the tube.

As shown in FIG. 14B, a venting valve 1410 can include two male connectors 1412, 1414 on either side for the rubber tube that milk will go in and out of, and a second inlet 1416 on top where air can go in one way. The venting valve 1410 may be plastic with a rubber duckbill valve or similar one-way valve 1418 attached that will be closed normally, but expand open when there is negative pressure inside of the valve or tubes.

Figure 15A:
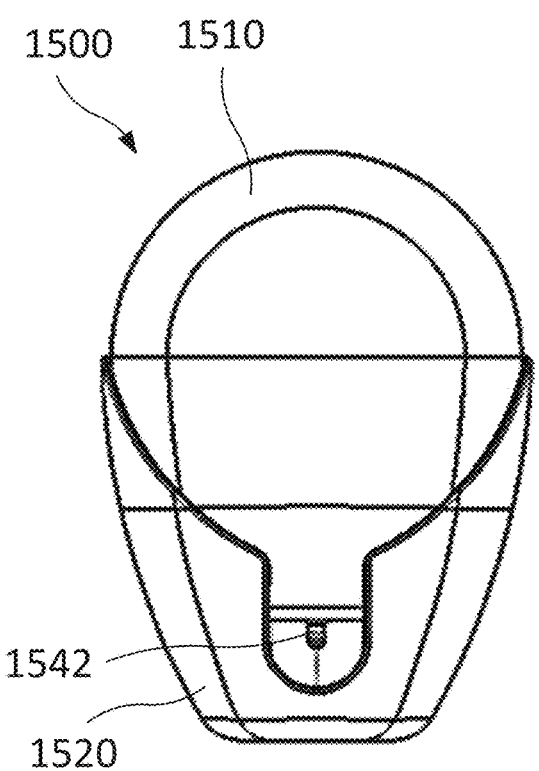
FIGS. 15A to 15C illustrate aspects of a breastmilk pumping and feeding device, in accordance with some embodiments.
Figure 15B:
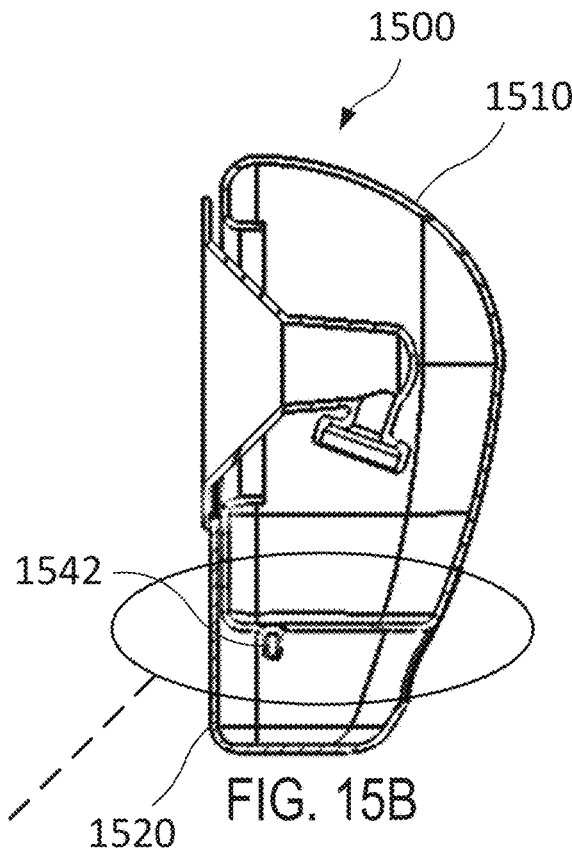
Figure 15C:
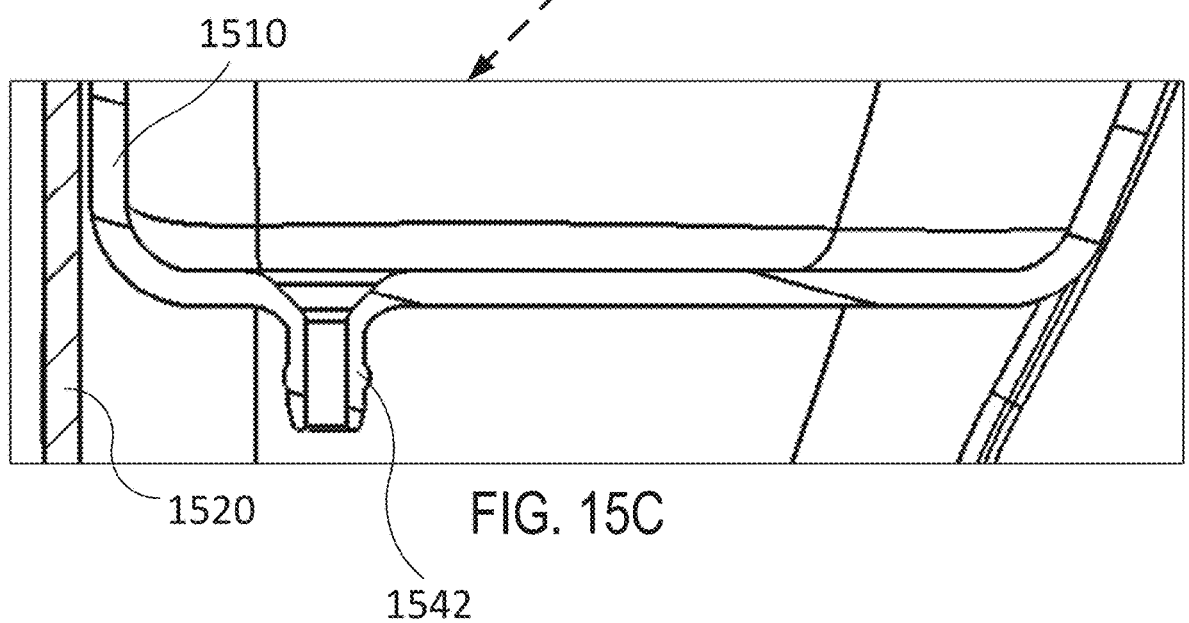

FIGS. 15A, 15B, and 15C illustrate aspects of an exemplary breastmilk pumping and feeding device 1500, according to embodiments of the present invention. As shown here, device 1500 includes a top container assembly 1510 having a feeding tube connection mechanism 1542, which is configured to attach with or otherwise engage a feeding tube. In some cases, feeding tube connection mechanism 1542 is a barb connector. Device also includes a bottom housing assembly 1520.

Aspects of an exemplary breastmilk pumping and feeding device 1600 are depicted in FIG. 16A (side view) and FIG. 16B (front view). As shown here, device 1600 includes a top container assembly 1610 that has or is in fluid communication with a nipple attachment 1614. Device also includes a bottom housing assembly 1620. In some embodiments, top container assembly 1610 can be configured to store or contain milk or other fluids. Device 1600 can also include a breast flange 1625.

FIG. 17A depicts a side view of a nipple attachment 1710 according to embodiments of the present invention. FIG. 17B depicts a cross-section view of a nipple attachment 1710 according to embodiments of the present invention. FIG. 17C depicts a rear view of a nipple attachment 1710 according to embodiments of the present invention. FIG. 17D depicts a front view of a nipple attachment 1710 according to embodiments of the present invention.

Figure 18:
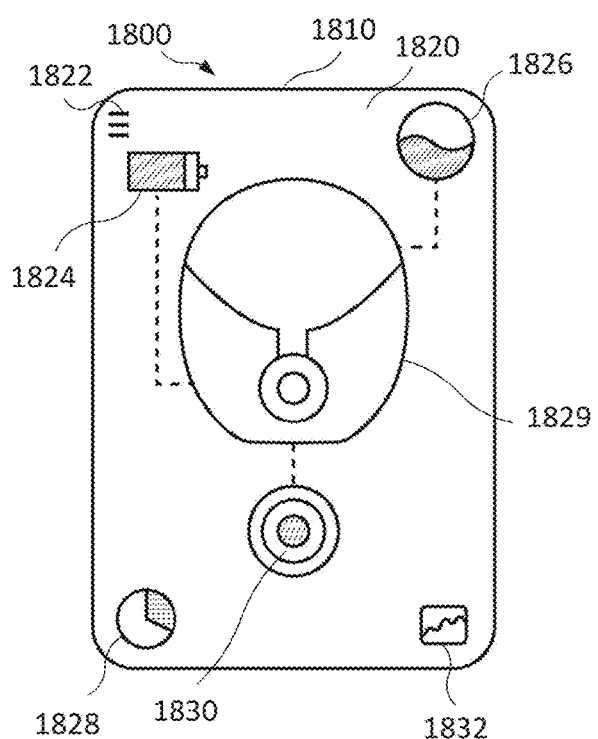
FIG. 18 illustrates aspects of a graphic user interface, in accordance with some embodiments.

FIG. 18 depicts aspects of a mobile computing device 1800 having a display screen 1810 with a graphical user interface 1820. This embodiment corresponds to use of a single breastmilk pumping and feeding device. As shown here, user interface 1820 includes a menu feature 1822, an electronics housing battery charge feature 1824, a milk chamber amount feature 1826 (the color green can indicate "primed"), a pump time feature 1828 (e.g. can indicate the amount of time pumped, out of 60 minutes), a consumed amount feature 1830 (e.g. can indicate the amount of fluid that the baby drank). The consumed amount feature 1830 can include one or more colored rings. Each ring may denote an incremental amount of fluid consumed (e.g. 1 ounce). In some cases, color fill can indicate a fraction of an incremental amount (e.g. a fraction of an ounce). User interface 1820 can also include a use feature 1832. In some cases, the use feature 1832 can display any of a variety of types of information, including history, graphs, data on amounts pumped, drank, times of pumping, and trends.

Figure 19:
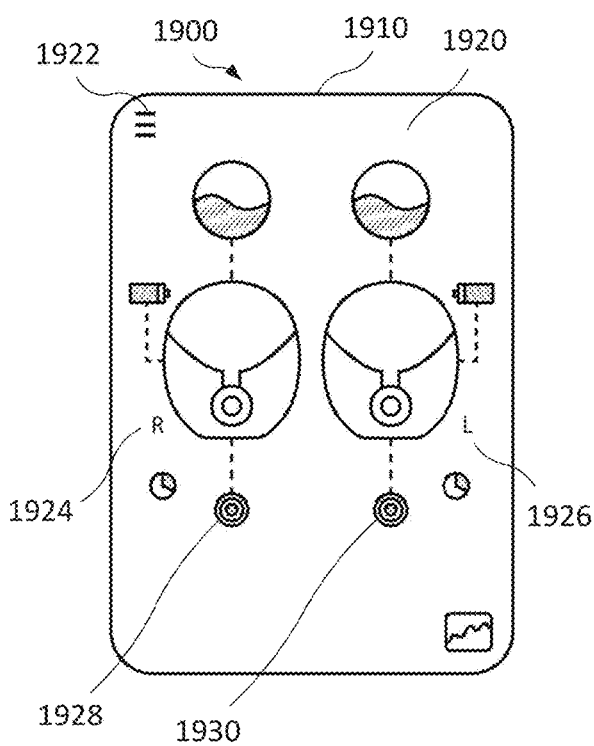
FIG. 19 illustrates aspects of a graphic user interface, in accordance with some embodiments.

FIG. 19 depicts aspects of a mobile computing device 1900 having a display screen 1910 with a graphical user interface 1920. This embodiment corresponds to use of a double breastmilk pumping and feeding device. As shown here, user interface 1920 includes a menu feature 1922, a right side indicator 1924 (e.g. indicating the right breast), a left side indicator 1926 (e.g. indicating the left breast), a right consumed amount feature 1928, and a left consumed amount feature 1930. A consumed amount feature 1928, 1930 can include one or more expanding colored rings. Each ring may denote an incremental amount of fluid consumed (e.g. 1 ounce). In some cases, color fill can indicate a fraction of an incremental amount (e.g. a fraction of an ounce).

In some embodiments, computing devices such as mobile computing devices can be programmed with an application (app) for use in operating and/or displaying information regarding the status or operation of one or more breastmilk pumping and feeding devices. An app may be configured as an Android app or an iOS app, and can receive data from the 1 or 2 pumps electronics housings which the user is using, e.g. via Bluetooth. The app can cause the computing device to display the amount of milk the baby is drinking (e.g. with accuracy of 1 to 5 ml, ±range of 1 to 3 ml). The computing device may also just display whether the baby is drinking, and additional detail can provide the amount. The computing device can display the amount of time pumping has been going on and battery power of the breastmilk pumping and feeding device. The computing device may display the amount of milk pumped or provide a venue to input extra pumped milk. The computing device can also display a history of feeding amounts and/or pumped amounts, with some analysis by time and day, like a graph.

Mobile computing devices may include personal devices such as phones or tablets. The app can cause the computing device to display a starting page, which features one device paired by Bluetooth (e.g. FIG. 18) or two devices paired by Bluetooth (e.g. FIG. 19) and its features with only visuals. Clicking any of the visuals provides either more information about that feature or the ability to control the device, via a screen.

In some embodiments, a mobile computing device for displaying operational information for an infant feeding fluid system can include features such as a screen, a processor, an electronic storage location operatively associated with the processor, and processor executable code stored on the electronic storage location and embodied in a tangible non-transitory computer readable medium. The processor executable code, when executed by the processor, can cause the processor to generate a graphical user interface on the screen. The graphical user interface can include a representation of feeding fluid consumed by an infant from the infant feeding fluid system. In some cases, the representation includes an amount of feeding fluid consumed by the infant from the infant feeding fluid system during one feeding session. In some cases, the representation includes an amount of feeding fluid consumed by the infant from the infant feeding fluid system over multiple feeding sessions. In some cases, the representation includes a time indicator for a feeding session. In some cases, a fluid feeding system can have a companion phone application that connects via Bluetooth to the system. The estimated amount of milk consumed by the infant can be tracked on the device and displayed on the phone application, which also stores feeding data from each individual pumping session. This allows the mother to keep track of how much milk the baby has drank over a span of time. This also allows a new set of automated data to be collected on when and how much a mother is feeding a child, how many mothers are using an aid for feeding, at what ages, and which infant/mother dyads could use other forms of breastfeeding assistance. Associating this with user provided demographics such as maternal age, geographic location, and the like, provides market knowledge to service mothers.

Embodiments of the present invention encompass related computer program products for informing a user of operational aspects of a pumping and/or feeding system. A computer program product can be embodied on a non-transitory tangible computer readable medium and can include computer-executable code for generating a graphical user interface on a screen of a mobile computing device, the graphical user interface including a representation of feeding fluid consumed by an infant from the infant feeding fluid system. In some cases, the representation includes an amount of feeding fluid consumed by the infant from the infant feeding fluid system during one feeding session. In some cases, the representation includes an amount of feeding fluid consumed by the infant from the infant feeding fluid system over multiple feeding sessions. In some cases, the representation includes a time indicator for a feeding session.

With regard to a battery symbol (e.g. feature 1824 of FIG. 18), color shading can indicate relative amount of charge remaining in the rechargeable electronics housing. Clicking feature 1824 can provide a whole number percentage value out of 100, and time remaining before needing to charge.

With regard to a container symbol (e.g. feature 1826), color shading can indicate a relative amount of milk currently in the milk container. A green color can indicate the container is primed, or there is enough for the baby to begin drinking. Absence of color can mean less than the required "primed amount" to allow baby to start drinking. Clicking feature 1826 can provide an estimated value of ounces displayed as a whole number such as "~1 oz," and a verbal or audible indication that the container is primed, like "ready for letdown."

With regard to a concentric rings symbol (e.g. feature 1830, 1926, or 1930), one or more concentric rings can indicate the amount the baby has consumed from the one or more breastmilk pumping and feeding devices. In some embodiments, there may only be one unshaded circle to start, representing the potential of 1 oz drank. Shading within the circle can indicate a relative amount drank within that ounce. When a full ounce is drank, the circle can be completely shaded. If more than one ounce is drank, a new concentric ring appears, and a relative amount of that circle can be shaded as the infant drinks. The amount that each concentric circle represents may be defined as a different amount than 1 oz, or may vary according to the age of the baby since newborns drink as little as a few mL at a time and 6 month old infants can drink more than 8 ounces. Clicking the image (e.g. 1830, 1926, or 1930) can provide the numeric amount of milk drank in ounces and ml (for partial ounces).

With regard to a clock symbol (e.g. feature 1828 of FIG. 18), the clock symbol indicates the amount of time the pump has been pumping at the breast via colored shading, relative to 60 minutes. Clicking the symbol (e.g. 1828) can provide the numerical amount of time the pump has been pumping at the breast in whole minutes, such as "17 min."

With regard to a graph symbol (e.g. feature 1832 of FIG. 18), clicking the graph symbol can lead to another page that contains collated data and/or graphical information based on the data collected by the pump. The other page may have a history of pumping frequency or amount by date, via graph or table. The other page may have visuals, tables, or graphs on the amounts drank, time of pumping, time of drinking, over different time periods such as days, weeks, months, or years. The app may be configured to confer a mobile computing device with the ability to export any of these analyses and share to other apps on the phone or computing device. Any of the mentioned parameters may be shown in comparison to averages from other mother infant dyads, or even against national or WHO standards, using weight, height, head circumference data that was input into the app.

With regard to a pump device symbol 1829, clicking the pump device symbol can lead to a controls page or feature. Here, the same controls that are available on the physical device (e.g. breastmilk pumping and feeding device) are available to manipulate. For example, the pump can be powered on and off via a power button, the strength of the vacuum suction to the breast can be adjusted up or down, the letdown to the baby can be initiated or stopped by clicking or unclicking the letdown button. Buttons may be present for adjustment of frequency of the vacuum suction as well. In some embodiments, clicking the device symbol 1829 will lead to a page or pop ups of controls for the device (e.g. power on/off, intensity, frequency, let down, and the like).

With regard to a menu symbol (e.g. feature 1822 or 1922), clicking on the menu symbol can lead to other features of the app, such as "resources," "profile," "help," or "contact us," or "connect." "Resources" may be a portal with further information for new mothers or breastfeeding mothers, "profile" may allow the user to choose which baby profile (if the device is used for multiple children) or see information input about the infant, such as birth date, weight, height, head circumference, diaper changes, sleep schedule, and the like. "Help" or "Contact Us" may provide lead to live chat, questions, FAQ, or contact information. "Connect" may lead to a portal that connects to other moms using the app, including finding or chatting with moms in the user's locality.

Figure 20:
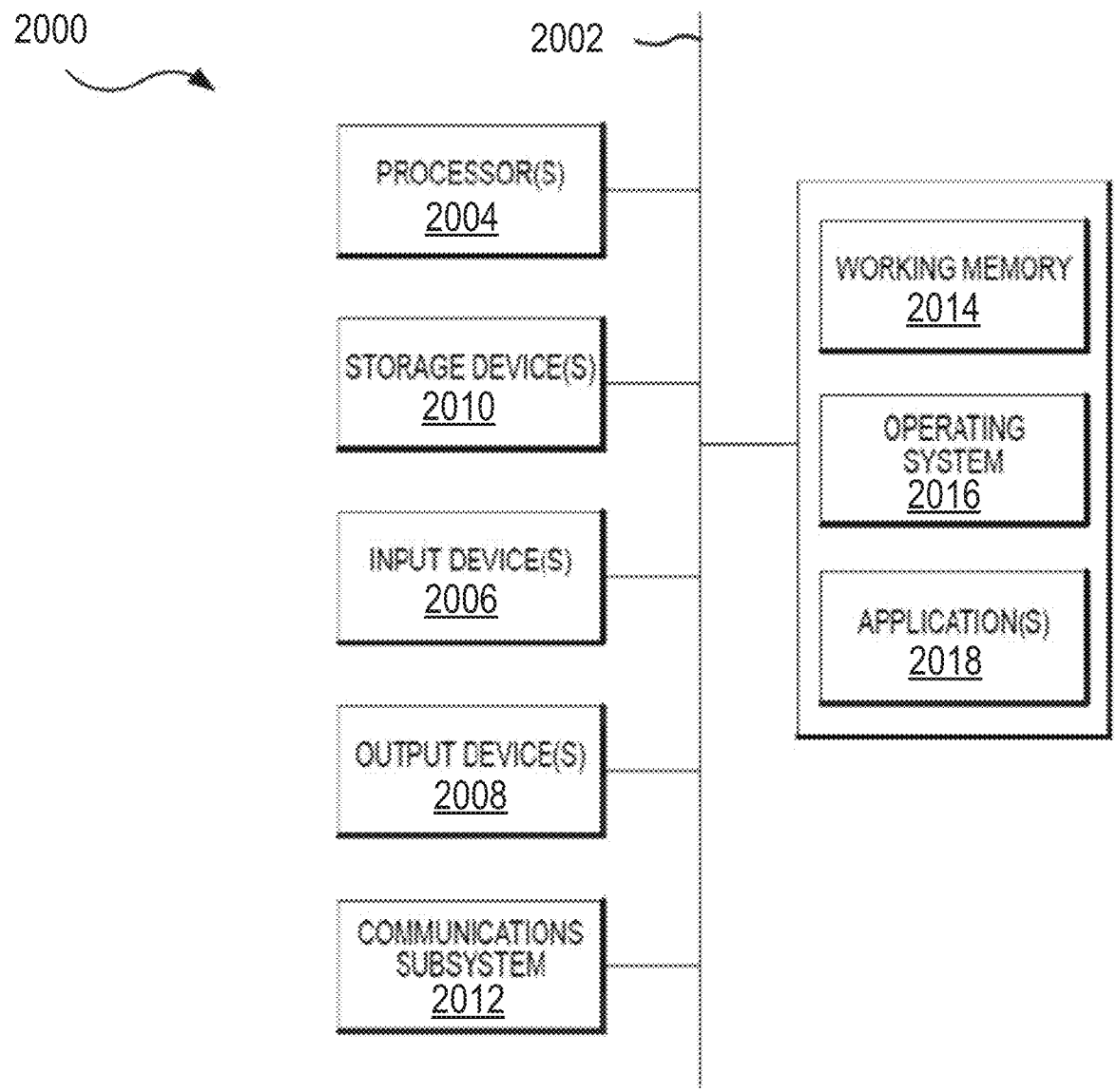
FIG. 20 shows aspects of a computer system, according to embodiments of the present invention.

FIG. 20 depicts aspects of an exemplary computer system or device 2000 configured for use with any of the breastmilk pumping and feeding devices and/or as a computing device (e.g. mobile computing device) disclosed herein, according to embodiments of the present invention. An example of a computer system or device 2000 may include an enterprise server, blade server, desktop computer, laptop computer, tablet computer, personal data assistant, smartphone, any combination thereof, and/or any other type of machine configured for performing calculations. Any computing devices encompassed by embodiments of the present invention may be wholly or at least partially configured to exhibit features similar to the computer system 2000.

The computer system 2000 of FIG. 20 is shown comprising hardware elements that may be electrically coupled via a bus 2002 (or may otherwise be in communication, as appropriate). The hardware elements may include a processing unit with one or more processors 2004, including without limitation one or more general-purpose processors and/or one or more special-purpose processors (such as digital signal processing chips, graphics acceleration processors, and/or the like); one or more input devices 2006, which may include without limitation a remote control, a mouse, a keyboard, a keypad, a touchscreen, and/or the like; and one or more output devices 2008, which may include without limitation a presentation device (e.g., controller screen, display screen), a printer, and/or the like.

The computer system 2000 may further include (and/or be in communication with) one or more non-transitory storage devices 2010, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer system 2000 can also include a communications subsystem 2012, which may include without limitation a modem, a network card (wireless and/or wired), an infrared communication device, a wireless communication device and/or a chipset such as a Bluetooth device, 802.11 device, WiFi device, WiMax device, cellular communication facilities such as GSM (Global System for Mobile Communications), W-CDMA (Wideband Code Division Multiple Access), LTE (Long Term Evolution), and the like. The communications subsystem 2012 may permit data to be exchanged with a network (such as the network described below, to name one example), other computer systems, controllers, and/or any other devices described herein. In many embodiments, the computer system 2000 can further comprise a working memory 2014, which may include a random access memory and/or a read-only memory device, as described above.

The computer system 2000 also can comprise software elements, shown as being currently located within the working memory 2014, including an operating system 2016, device drivers, executable libraries, and/or other code, such as one or more application programs 2018, which may comprise computer programs provided by various embodiments, and/or may be designed to implement methods, and/or configure systems, provided by other embodiments, as described herein. By way of example, one or more procedures described with respect to the method(s) discussed herein, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code can be stored on a non-transitory computer-readable storage medium, such as the storage device(s) 2010 described above. In some cases, the storage medium might be incorporated within a computer system, such as computer system 2000. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer system 2000 and/or might take the form of source and/or installable code, which, upon compilation and/or installation on the computer system 2000 (e.g., using any of a variety of generally available compilers, installation programs, compression/decompression utilities, and the like), then takes the form of executable code.

It is apparent that substantial variations may be made in accordance with specific requirements. For example, customized hardware might also be used, and/or particular elements might be implemented in hardware, software (including portable software, such as applets, and the like), or both. Further, connection to other computing devices such as network input/output devices may be employed.

As mentioned elsewhere herein, in one aspect, some embodiments may employ a computer system (such as the computer system 2000) to perform methods in accordance with various embodiments of the disclosure. According to a set of embodiments, some or all of the procedures of such methods are performed by the computer system 2000 in response to processor 2004 executing one or more sequences of one or more instructions (which might be incorporated into the operating system 2016 and/or other code, such as an application program 2018) contained in the working memory 2014. Such instructions may be read into the working memory 2014 from another computer-readable medium, such as one or more of the storage device(s) 2010.

Merely by way of example, execution of the sequences of instructions contained in the working memory 2014 may cause the processor(s) 2004 to perform one or more procedures of the methods described herein.

The terms "machine-readable medium" and "computer-readable medium," as used herein, can refer to any non-transitory medium that participates in providing data that causes a machine to operate in a specific fashion. In an embodiment implemented using the computer system 2000, various computer-readable media might be involved in providing instructions/code to processor(s) 2004 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 2010. Volatile media may include, without limitation, dynamic memory, such as the working memory 2014.

Exemplary forms of physical and/or tangible computer-readable media may include a floppy disk, a flexible disk, hard disk, magnetic tape, or any other magnetic medium, a compact disc, any other optical medium, ROM, RAM, and the like, any other memory chip or cartridge, or any other medium from which a computer may read instructions and/or code. Various forms of computer-readable media may be involved in carrying one or more sequences of one or more instructions to the processor(s) 2004 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 2000.

The communications subsystem 2012 (and/or components thereof) generally can receive signals, and the bus 2002 then can carry the signals (and/or the data, instructions, and the like, carried by the signals) to the working memory 2014, from which the processor(s) 2004 retrieves and executes the instructions. The instructions received by the working memory 2014 may optionally be stored on a non-transitory storage device 2010 either before or after execution by the processor(s) 2004.

It should further be understood that the components of computer system 2000 can be distributed across a network. For example, some processing may be performed in one location using a first processor while other processing may be performed by another processor remote from the first processor. Other components of computer system 2000 may be similarly distributed. As such, computer system 2000 may be interpreted as a distributed computing system that performs processing in multiple locations. In some instances, computer system 2000 may be interpreted as a single computing device, such as a distinct laptop, desktop computer, or the like, depending on the context.

A processor may be a hardware processor such as a central processing unit (CPU), a graphic processing unit (GPU), or a general-purpose processing unit. A processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. All features of the described systems and devices are applicable to the described methods mutatis mutandis, and vice versa. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

According to some embodiments, machine-readable code instructions for, and/or data generated or used by, breastmilk pumping and feeding devices and/or computing devices (which may include smart phones or other mobile computing devices) can be stored on or executed by any of a variety of computing modalities, including without limitation personal computers, servers (e.g. hosted and/or privately owned servers), internet connections, cloud hosts, cloud based storage, and the like. According to some embodiments, data acquired by a breastmilk pumping and feeding devices can be related to a mobile computing device (e.g. a smart phone) via a data exchange technology (e.g. Bluetooth) and then relayed to a secure server via the cloud (e.g. servers that are accessed over the Internet, and the software, services, and/or databases that run on those servers).

According to some embodiments, a breastmilk pumping and feeding device can be configured to provide paced feeding. The side lying position of feeding the baby from a bottle like device, but facing the breast, can mimic breastfeeding and allow for holding and feeding the bottle as if the user were breastfeeding naturally (e.g. getting accustomed to breastfeeding position, bonding with the baby, and the like). Additionally, it can allow for paced feeding, which means that the baby does not experience a downward stream of continuous strong flow, but has agency over drawing the milk from the bottle as it does at the breast. This method (paced feeding, or side-lying feeding) is used as a technique in NICUs, where infants may have a weaker control of swallowing and sucking abilities, and may not be able to regulate the flow of milk to avoid choking. Side lying, instead, allows milk to pool in the cheek so that the infant can swallow when ready. Further, paced feeding is often recommended for mothers and infants that are having difficulty at the breast, but would like to pursue breastfeeding. When the bottle is held horizontal to the floor, as opposed to tilted downward (and the baby is positioned either sitting straight up or laying to the side), then the infant needs to dictate when the milk comes to the mouth by drawing out of a bottle that is not dripping milk out, but filled just below the nipple slit. This further reinforces the baby to expect to need to pull milk out in order to drink, and also helps develop sucking muscles which are necessary when sucking directly at the breast.

Figure 21A:
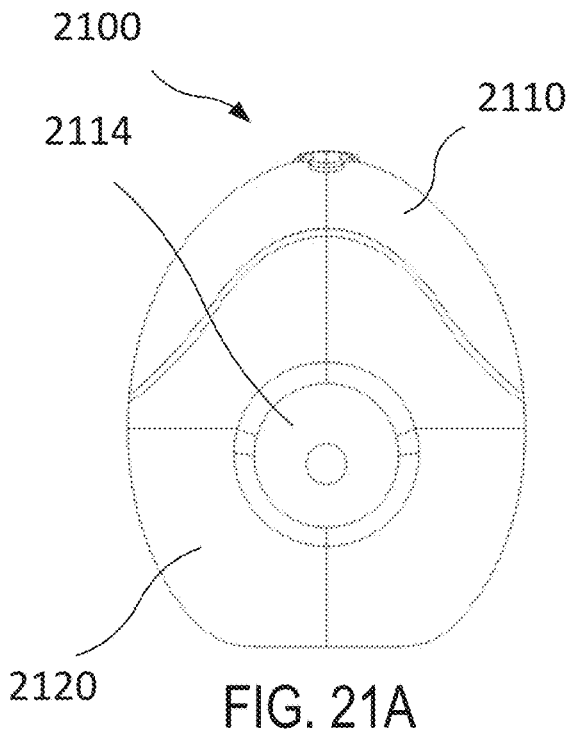
FIGS. 21A to 21O illustrate aspects of a breastmilk pumping and feeding device, in accordance with some embodiments.
Figure 21B:
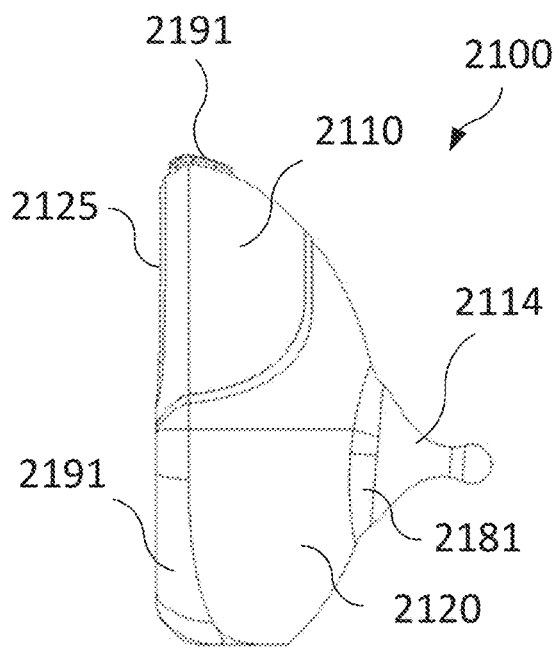
Figure 21C:
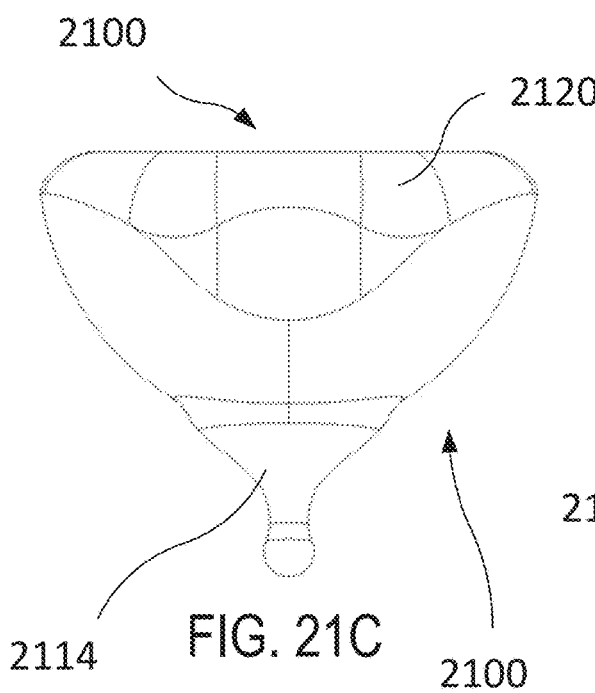
Figure 21D:
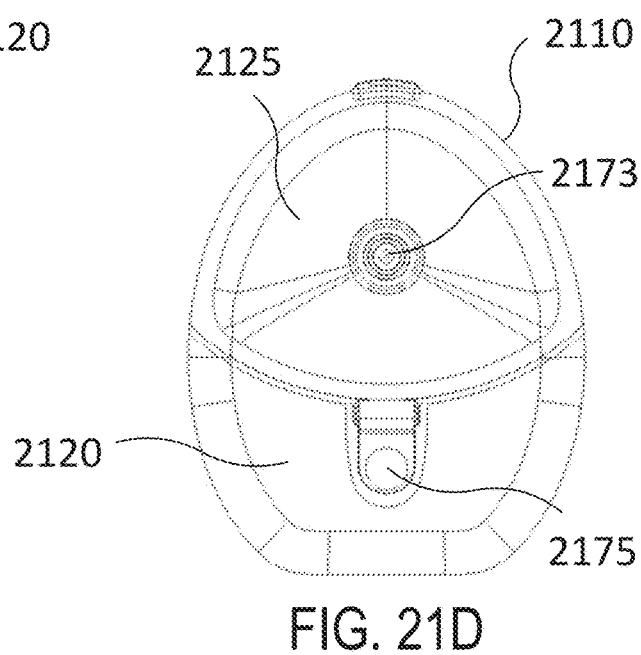
Figure 21E:
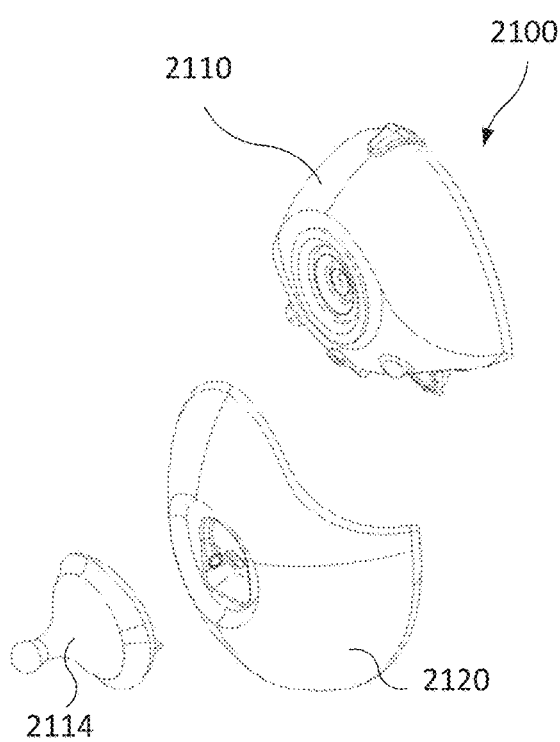
Figure 21F:
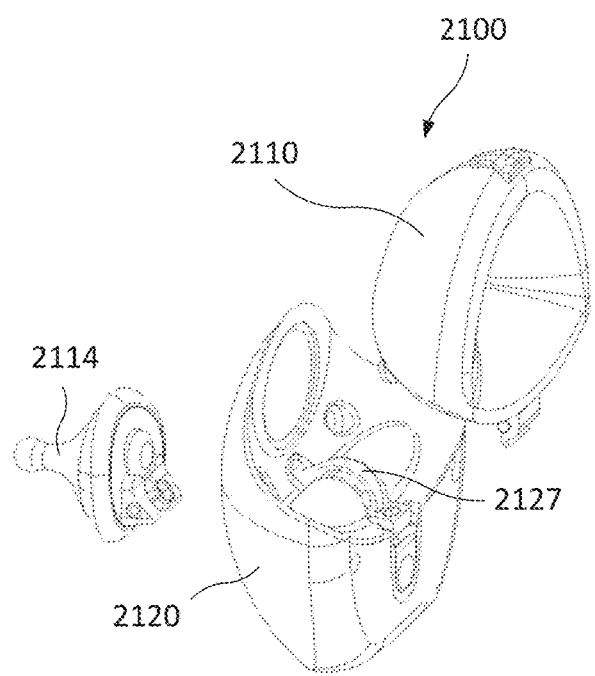

FIGS. 21A to 21D depicts aspects of an exemplary breastmilk pumping and feeding device 2100, according to embodiments of the present invention. As shown here, the breastmilk pumping and feeding device 2100 is in an assembled configuration, and includes a top container assembly 2110 and a bottom housing assembly 2120. The top container assembly 2110 and the bottom housing assembly 2120 are coupled together. In some cases, the top container assembly 2110 can be referred to as or can include a milk storage container. In some cases, the bottom housing assembly 2120 can be referred to as or can include a pump housing front. As further discussed herein device 2100 also includes a nipple attachment or nipple component 2114. The bottom housing assembly 2120 can operate to contain electronic and/or other mechanisms of the device 2100. The top container assembly 2110 can operate to contain and/or store milk or other liquids. In some cases, a top container assembly 2110 can include a milk storage container spout 2191. As illustrated in FIG. 21D, the breast flange 2125 can be incorporated into the milk container or top container assembly 2110, and the entire milk container can attach with the bottom housing assembly 2120. In some cases, a feeding device or system 2100 can include a nipple ring component 2181. In some cases, a feeding device or system 2100 can include a pump housing back 2171. In some cases, a feeding device or system 2100 can include a pump diaphragm 2173. In some cases, a feeding device or system 2100 can include a container click in switch 2175. As shown in FIG. 21E, the milk container component or top container assembly 2110 and the nipple component or nipple attachment 2114 can detach from the main pump body or bottom housing assembly 2120. As illustrated in FIG. 21F, milk or liquid can be transferred from the milk container or top container assembly 2110 to the nipple attachment 2114 via operation of a peristaltic pump wheel mechanism 2127.

As depicted in FIGS. 21G-1 to 21G-3, the nipple attachment or assembly 2114 (which may also be referred to as, or be included as part of, a nipple component subassembly) can be connected with the milk container or top container assembly 2110 via a small tube 2144, which is driven by a peristaltic pump wheel 2138. In some cases, tube 2144 is part of a container subassembly 2155. Peristaltic tubing 2144 can provide fluid communication between container 2110 and nipple 2114. In some cases, wheel mechanism 2138 is part of a pump housing subassembly 2165. In some cases, a bottom housing assembly 2120 can be part of the pump housing subassembly 2165. A diaphragm 2119 of the top container assembly 2110 can operate to create negative pressure on the breast, causing milk or fluid to be expressed. Milk or fluid can be stored around the breast flange 2125, and backflow can be prevented via operation of a one-way valve such as a duckbill valve 2126. As shown here, the pump housing subassembly 2165 can include a cavity 2166 in which nipple component subassembly 2114 is inserted.

Figure 21H:
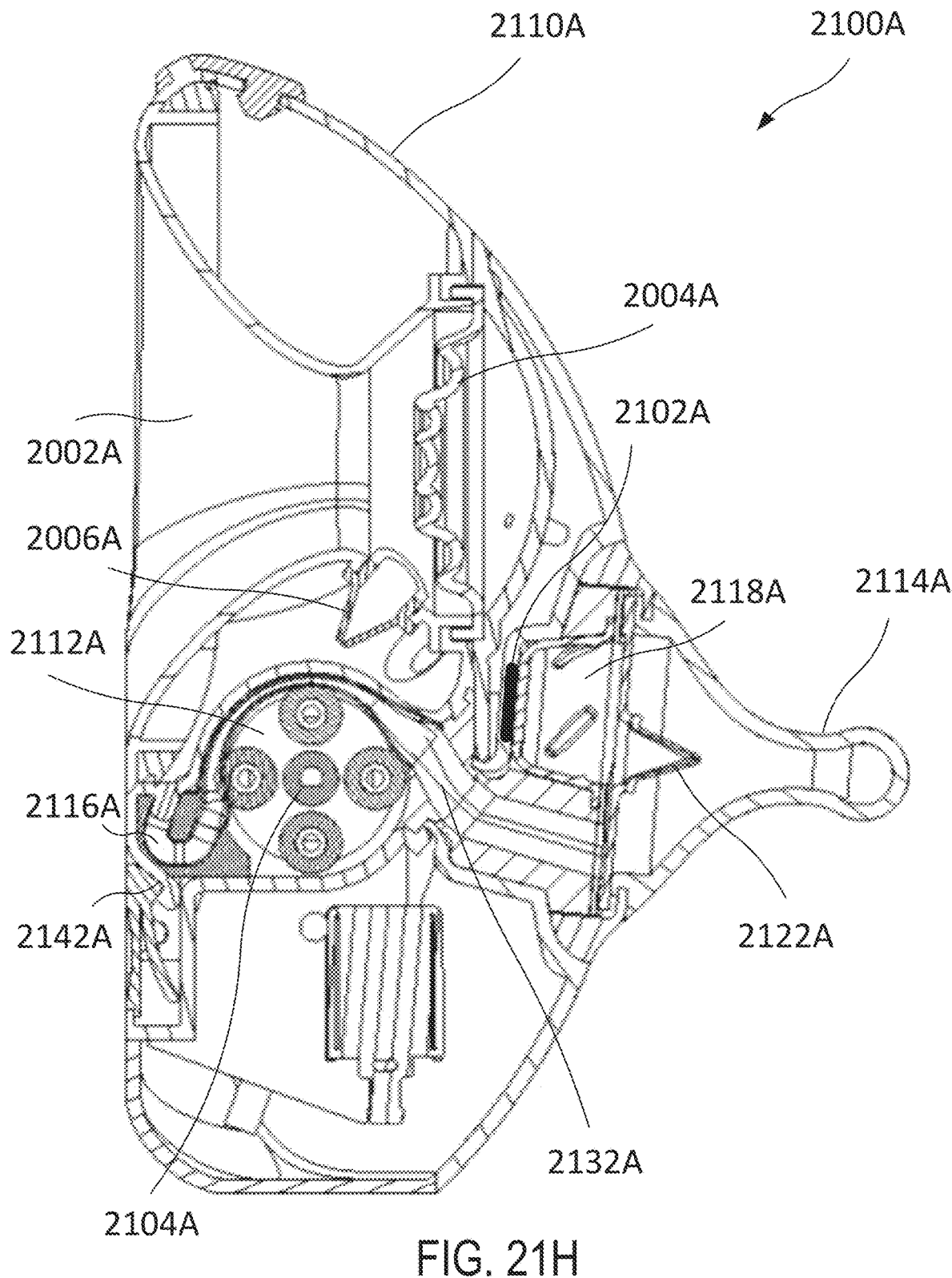

As illustrated in the side cross-section view provided by FIG. 21H, a breastmilk pumping and feeding device 2100A, which may be provided as or encompass a system for determining an amount of a feeding fluid that is consumed by an infant, can include a chamber or container 2110A that stores feeding fluid. The system 2100 can also include a breast flange 2002A, a pump diaphragm 2004A, a one-way valve such as a duckbill valve 2006A (e.g. for the flange) that connects the breast flange 2002A with the container 2110A, providing fluid communication therebetween. Further, the system 2100A has a dosing mechanism 2112A that can include a peristaltic pump wheel mechanism. As shown here, the dosing mechanism 2112A can receive feeding fluid from the chamber or container 2110A, and can dispense discrete packets of feeding fluid, e.g. into or toward a nipple 2114A, for consumption by an infant. For example, the peristaltic pump wheel can create peristaltic action to move fluid from the container 2110A toward the nipple 2114A. Each discrete packet of feeding fluid can have a discrete packet volume. Hence, the nipple 2114A can receive feeding fluid dispensed by the dosing mechanism 2112A and can allow feeding fluid to flow to the infant. The system 2100A can also include a sensor assembly or hall effect sensor 2102A (related aspects of which are further depicted in FIGS. 21N and 21O) that operates to determine when the compressible chamber 2118A is ready to receive a new discrete packet of feeding fluid. Further, the system 2100A can include a counting mechanism 2104A that operates to register a count for each dispensing event performed by the dosing mechanism 2112A. In some embodiments the counting mechanism is attached to the axel which drives the peristaltic wheel 2112A. In some embodiments, the counting mechanism can include a hall effect sensor or a magnetic encoder, for example. The number of rotations of the peristaltic pump can be counted by a hall effect sensor, which determines the amount of fluid that was made available to the infant. In some embodiments, the number of rotations of the peristaltic pump can be counted by a magnetic encoder. Embodiments of the present invention encompass the use of any of a variety of counting mechanisms for counting the number of rotations (or partial rotations) of the peristaltic pump. In the embodiment provided here, system 2100A includes a fluid connection 2116A (e.g. a right angle barb angle connection piece) that attaches with the container 2110A and an intake of the dosing mechanism (e.g. peristaltic tube a peristaltic pump wheel) thus providing fluid communication therebetween. In some cases, fluid connection 2116A does not include a plug. As discussed elsewhere herein, system 2100A can also include a processor that determines the amount of feeding fluid that is consumed by the infant based on the discrete packet volume and the number of registered counts.

As indicated above, a dosing mechanism 2112A can include a peristaltic pump. A sensor assembly can include a hall effect sensor. Further, the system 2110A can include a collapsible feedbag 2118A that receives the discrete packets of feeding fluid dispensed by dosing mechanism 2112A and that transmits the discrete packets of feeding fluid toward the nipple 2114A. The collapsible chamber 2118A can operate to hold milk to be made available to the baby. In some cases, the feeding fluid traves from the feedbag 2118A to the nipple 2114 via a one way duckbill valve 2122A (e.g. for the nipple). The valve 2112A can operate to ensure that milk flows one way to the infant, and/or to ensure that air does not enter the feedbag 2118A and falsely indicate that the compressible chamber contains fluid. As shown here, system 2100A can also include a fluid connection 2132A (e.g. a fluid connection through plug) that attaches with the peristaltic tube and helps to provide fluid communication with the nipple 2114A. In some cases, system 2100A can also include a container click in switch component 2142A that operates to hold the container 2110A in place once inserted. In some cases, a system 2100A can include a magnet in operative association with the collapsible feedbag 2118A. The sensor assembly can operate to determine that the collapsible chamber is available for filling or receiving feeding fluid (or the peristaltic pump is ready for activation) when the magnet reaches a first distance away from the hall effect sensor and that the peristaltic pump is ready for pausing (or deactivation) when the magnet reaches a second distance away from the hall effect sensor, the first distance being greater than the second distance. In this way, embodiments of the present invention encompass systems and methods for sensing a collapsing bag with a hall effect sensor, and in turn the system can cause motion of a peristaltic pump pushing milk to an infant and allow for quantification of the dispensed milk. Optionally, the milk container can be used as a part of the peristaltic pump by being a backing to provide counterpressure for the peristaltic rollers. In some cases, a collapsible compartment can operate with a magnet/hall effect and peristaltic tubing to orally dose on demand.

By combining a peristaltic pump with a sensor assembly, it is possible to realize several advantages, including ease of use and the ability to allow the infant to lead the feeding action. In some embodiments, having the sensor be separated from the path of the breast milk allows for easier cleaning, as the sensor does not need to come into contact with the breast milk. In some embodiments, because a sensor is passive, it allows the baby to lead the refilling of the bag. Relatedly, embodiments disclosed herein provide a compressible baby bottle that automatically refills when the baby finishes drinking, rather than a pump that pumps milk to the baby through a straw (and which may involve a flow sensor). Hence, exemplary embodiments create a more natural feeding action for the infant. What is more, embodiments disclosed herein provide systems and methods that may not require venting, for example due to the use of a compressible feedbag, which also provides an easy way for the infant to suck without fighting against a closed volume that would require a venting source. Even with a separate venting source to move fluid along (so the infant is not forced to drink as if from a pinched off straw), such a venting may require another backflow valve in the system. Further, embodiments disclosed here do not rely on gravity. In contrast to a sensor and fill method where the milk would have to drop to a location where the sensor detects it, peristaltic pumping embodiments disclosed herein can provide pumping to the baby's reservoir, and the milk can be moved from the bottom of the milk container (so as not to waste any), up to a position that is closer to the anatomic nipple of the mother, despite the size or configuration of the milk container. Still further, embodiments disclosed herein can provide enhanced accuracy. For example, a peristaltic pump can send a highly precise packet of liquid to the infant, which can be easily calculated by revolutions of the peristaltic pump, without touching the fluid the baby drinks. Yet further, embodiments of the present invention can provide enhanced drinking speed features. For example, a magnet/bag combination can act independently of the peristaltic pump, and can behave in response only to the infant. Because the magnet/bag can indicate any amount of flex, and when returned to its home state near the hall effect sensor, it will indicate that it is full, and no decision needs to be made by the device as to how much milk should be sent. If the milk bag or feedbag is in any state rather than full, the peristaltic pump can continue to dose one packet of milk until the bag is full. This allows for real time or on-demand response to the baby's actions. The feedbag or compartment does not need to wait to refill (like a chamber+empty/full infrared reading configuration) in order to record one bolus of milk, and then dispense it to the infant. Further, embodiments of the present invention provide enhanced operability with regard to an infant's suction strength. For example, a surprising benefit of this method is also that, with a hall effect sensor and magnet configuration, the sensor can operate to detect the amount of flex the infant is applying to the bag. This can be indicative of strength/integrity of suction differences between one infant to the other, or based on the infant's age or practice of skill in sucking. This can also allow for monitoring progress and detecting or analyzing which methods of drinking practice result in better suction or consumption of milk. A correlation can also be realized between the flex distance (suction strength) and amount of milk the infant consumes, or weight gain, and the like. Further, embodiments of the present invention provide enhanced operability with regard to providing easily usable systems for infants with latch issues. For example, in infants that have issues with latch or efficient suction, drinking from a small flexible chamber as disclosed herein allows the infant to consume feeding fluid while doing less work. What is more, embodiments of the present invention provide enhanced continuous drinking configurations. In some other non-vented drinking systems, the infant may be required to open their mouth to allow air to come back into the system. This can interrupt continuous drinking, which the infant would normally have at the breast. If the vent is at the bulbous portion, air may be required to run through the milk, which will aerate it and provide more air into the infant's GI system. With a peristalsis mechanism and a flexible magnet bag as disclosed herein, air will not need to be introduced in the chamber in order to create continuous drinking.

Figure 21I:
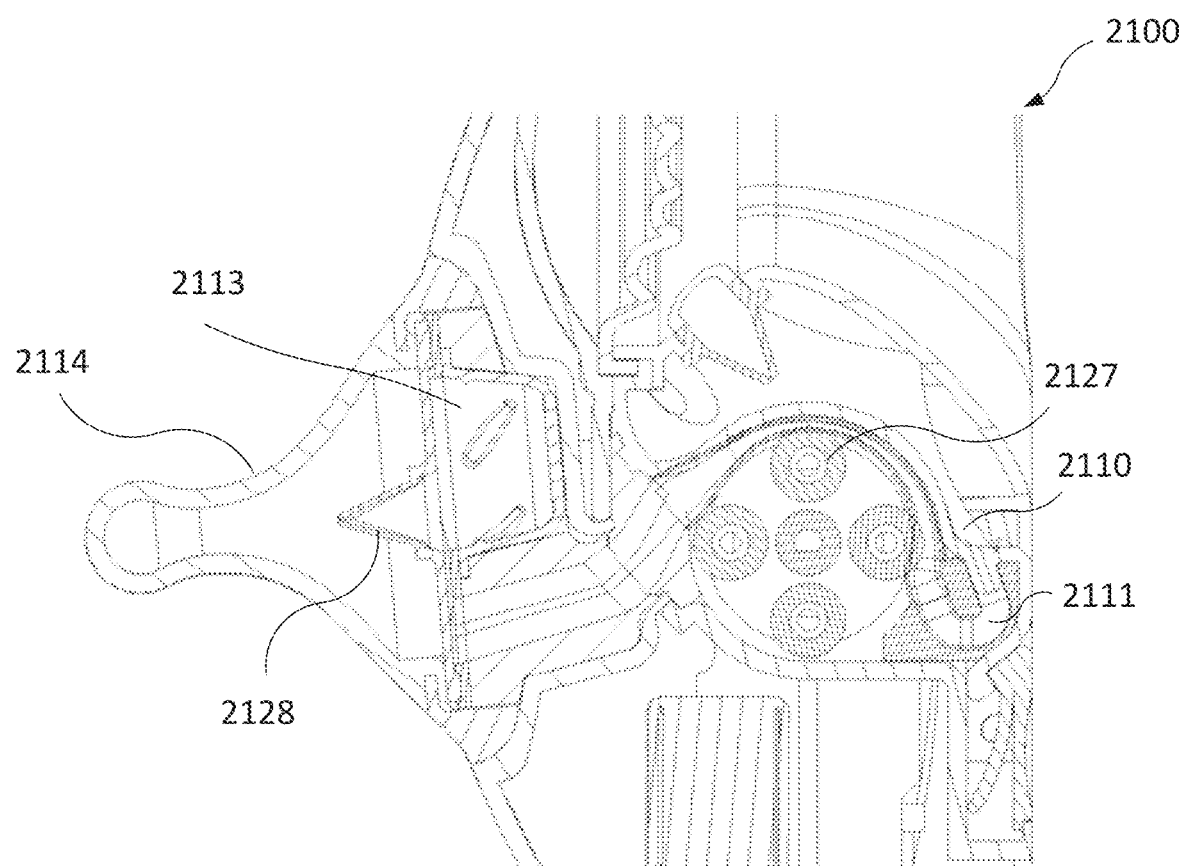
Figure 21J:
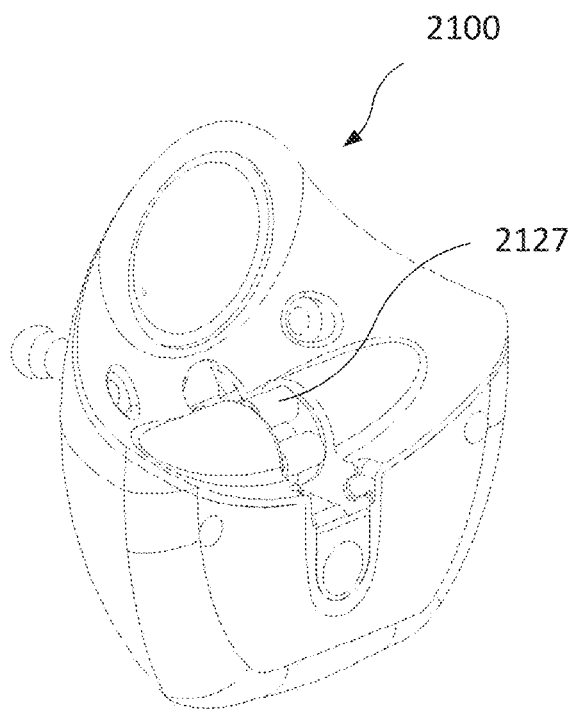
Figure 21K:
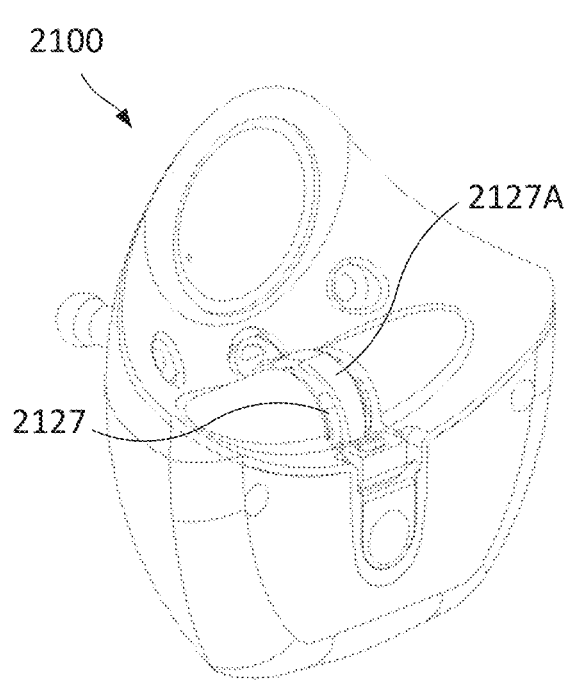
Figure 21L:
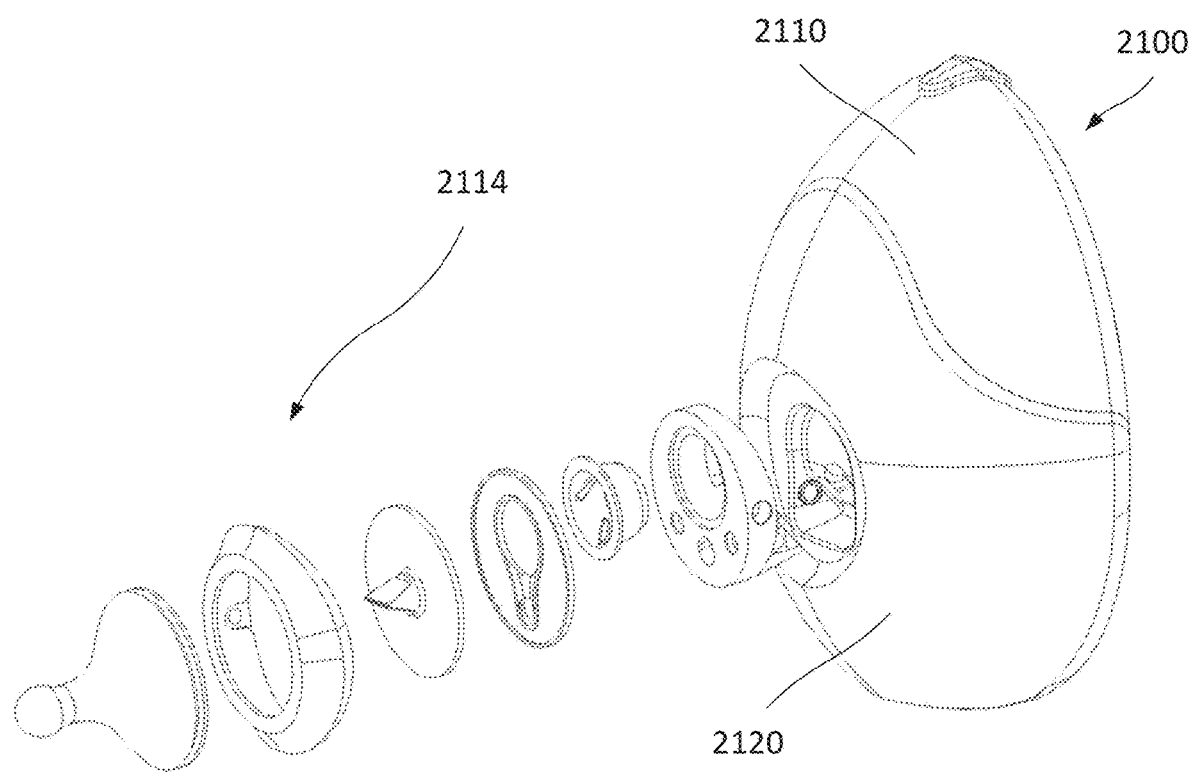
Figure 21M:
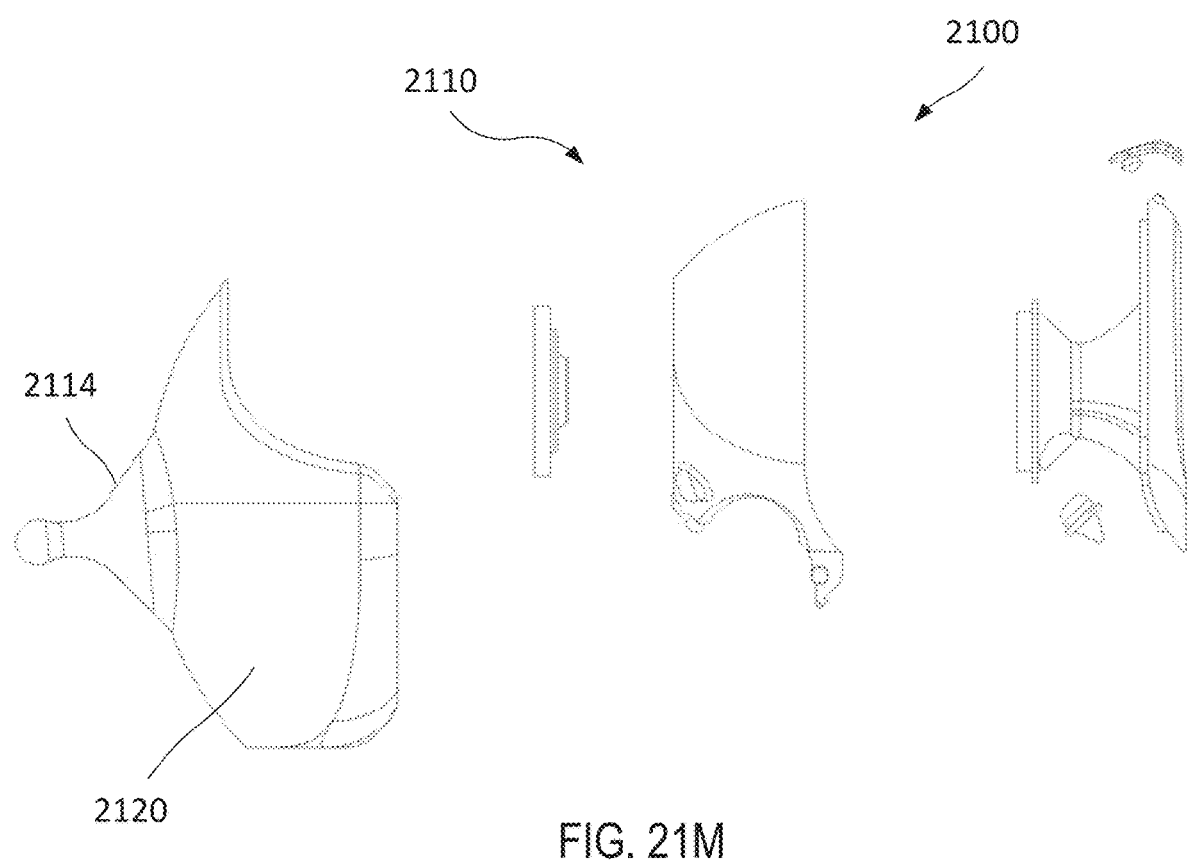

FIG. 21H provides a cross-section view of the assembled device 2100. As shown in the partial cross-section view of FIG. 21I, milk or fluid from the top container assembly 2110 can be emptied into tubing 2111. The peristaltic wheel mechanism 2127 can turn, thereby operating to pump the milk or fluid coming from the top container assembly 2110 through the tube 2111, and into the nipple assembly or attachment 2114. Milk or fluid can come up through the tube, and can be stored in the feedbag 2113. The baby can suck on the nipple attachment 2114, which facilitates transfer of milk or fluid from the feedbag 2113 to the baby. According to some embodiments, the baby can suck on the nipple attachment, which collapses the feedbag, containing a magnet. As the magnet moves away from the hall effect sensor inside the housing, the peristaltic pump is activated to refill the feedbag. When the magnet returns to proximity to the hall effect sensor (e.g. due to the expansion of the feedbag 2113), the peristaltic pump will cease sending milk to the feedbag. In that pattern, the baby is supplied milk or fluid by demand, and the resulting rotations of the peristaltic motor multiplied by the amount of fluid passed in one rotation determine the amount of fluid dispensed. A backflow valve 2128 can operate to prevent or inhibit milk or fluid from re-entering into the feedbag 2113 once it has been sucked out and further prevent air from outside the nipple apparatus to enter the feedbag and falsely indicate fullness of milk when the baby's mouth does not form a vacuum around the nipple. In some embodiments, the feedbag 2113 contracts when the baby drinks milk out of the nipple. When the feedbag 2113 contracts, a sensor is triggered activating the peristaltic wheel mechanism 2127 to pump more fluid into the nipple assembly or attachment 2114. A sensor counts the number of rotations of the peristaltic wheel mechanism 2127, allowing for the volume of fluid passing through to be counted. FIG. 21J shows aspects of the device 2100 without the peristaltic tubing of the peristaltic pump wheel mechanism 2127. FIG. 21K shows aspects of the device 2100 with the peristaltic tubing 2127A of the peristaltic pump wheel mechanism 2127. FIG. 21L provides an exploded view of the nipple attachment or assembly 2114. FIG. 21M provides an exploded view of the top container assembly 2110. As described herein, embodiments of the present invention encompass systems and methods for the quantification of fluid dispensed. Such techniques can involve a bag+hall effect sensor+peristaltic pump, and may be a modification of a two bag system as also disclosed herein. Embodiments also encompass systems and methods that involve the monitoring of the amount that anyone drinks on demand, to very small precise quantities. Such embodiments provide excellent applications to the small quantities that preterm or full term infant has, but could also be applied to oral dosing or monitoring of oral intake that any child, adult or elderly person does. Hence, devices can be configured to provide on-demand monitoring fluid intake, which may involve quantification techniques as disclosed elsewhere herein.

Figure 21N:
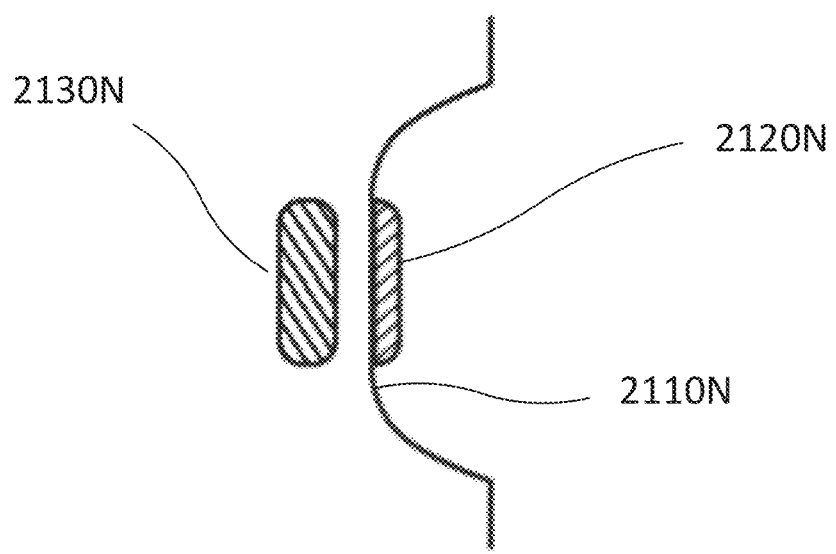
Figure 21O:
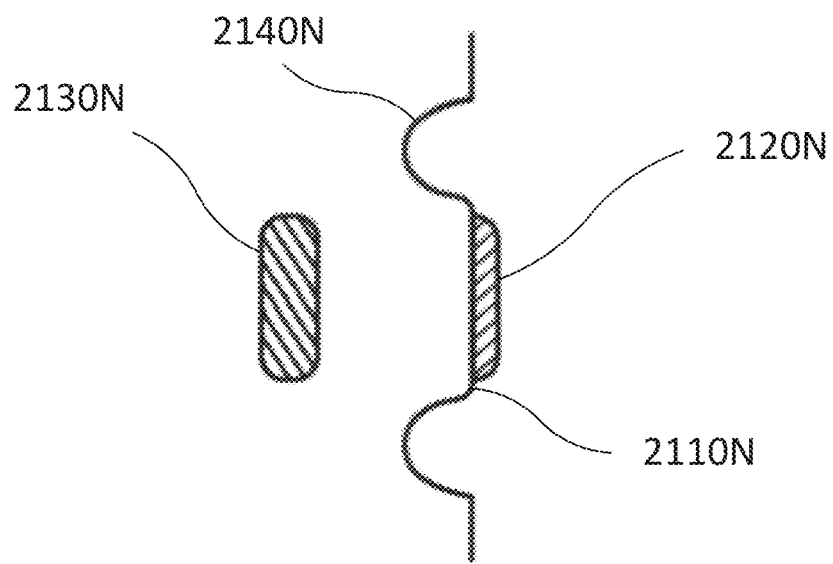
Figure 22A:
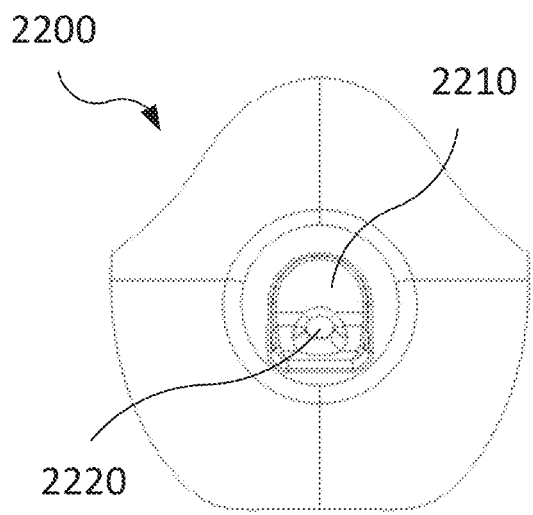
FIGS. 22A to 22E illustrate aspects of a breastmilk pumping and feeding device, in accordance with some embodiments.
Figure 22B:
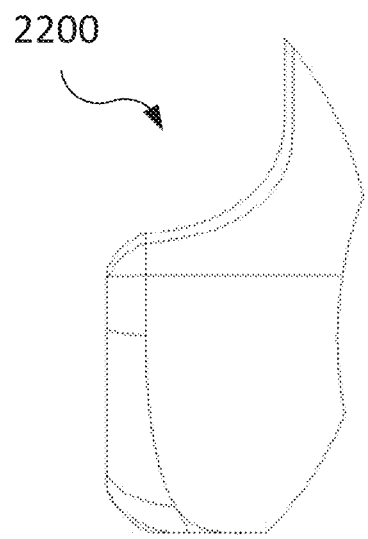
Figure 22C:
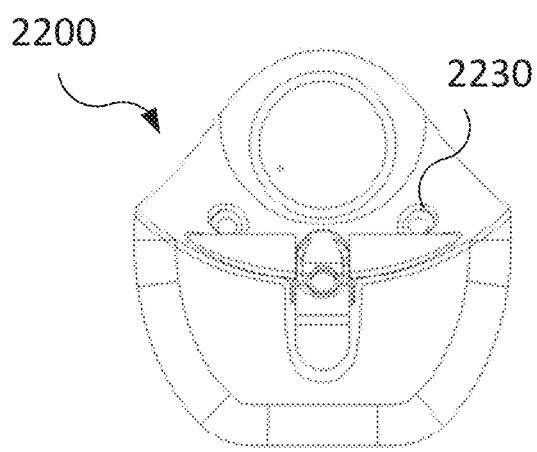
Figure 22D:
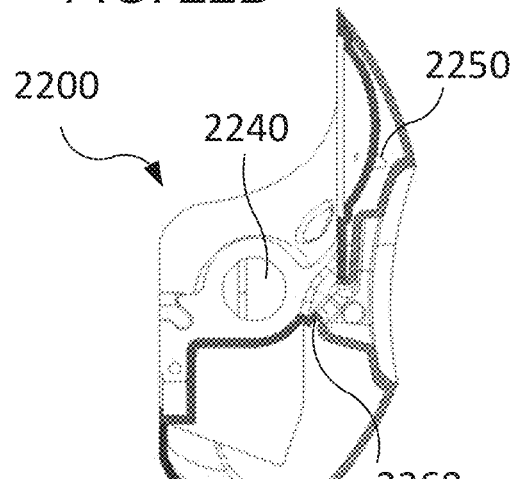
Figure 22E:
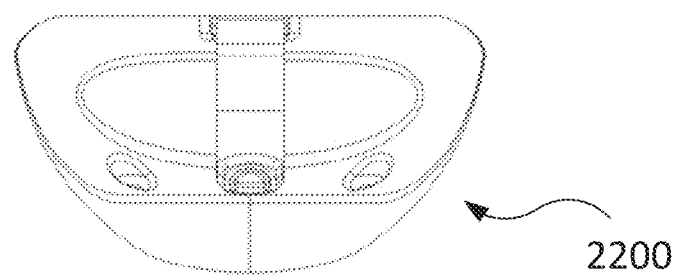

FIGS. 21N and 21O depict operational aspects of a feedbag, according to embodiments of the present invention. As shown here, in FIG. 21N, when the feedbag or compressible chamber 2110N is in a "full" configuration or position (e.g. fully filled with a feeding fluid such as milk), the magnet 2120N is pushed or positioned closely to a hall effect sensor 2130N. In some embodiments, when the feedbag 2110N is fully filled, the magnet 2120N will be pushed as close to the hall effect sensor 2130N as it will go. As shown here, the magnet 2120N can be embedded in the feedbag 2110N, and can be sensed by the hall effect sensor 2130N. The hall effect sensor 2130N can be positioned outside of the feedbag 2110N, in line with the axis of the magnet 2120N. As shown in FIG. 21O, when the feedbag or compressible chamber 2110N is compressed, the magnet 2120N is positioned farther away from the hall effect sensor 2130N. In some cases, when the feedbag 2110N is in an "empty" configuration or position (e.g. empty of a feeding fluid such as milk), the magnet 2120N is positioned as far away from the hall effect sensor 2130N as it will go. The feedbag 2110N can fold in on itself (e.g. via folds 2140N) to create a fully compressed geometry. As discussed elsewhere herein, the collapsing or compression of the feedbag 2110N can provide an indication that some milk has been taken (e.g. by the baby), and that the feedbag 2110N is then able to receive additional milk. According to some embodiments, the peristalsis dose is smaller than the negative volume flex of the feedbag, so at least one more packet can be provided.

FIGS. 22A to 22E depict aspects of a breastmilk pumping and feeding device 2200, according to embodiments of the present invention. As shown here, a system 2200 can include a cavity 2210 in which a nipple component subassembly can be inserted, and a fluid connection point or hole 2220, where a nipple component can connect to a fluid connection tube. System 2200 can also include milk container alignment features 2230. Further, system 2200 can include a cutout 2240 for ball bearings that house a peristaltic wheel assembly, a barb 2250 that connects an air pump with a diaphragm cavity, and a meeting point 2260 of a front and back housing.

Figure 23A:
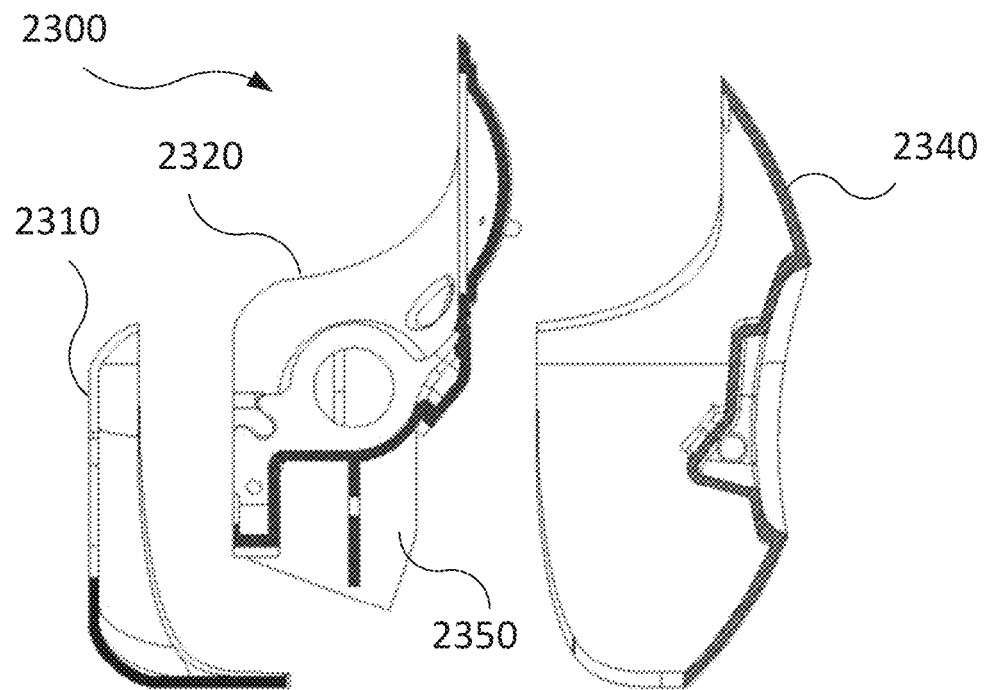
FIGS. 23A and 23B illustrate aspects of a breastmilk pumping and feeding device, in accordance with some embodiments.
Figure 23B:
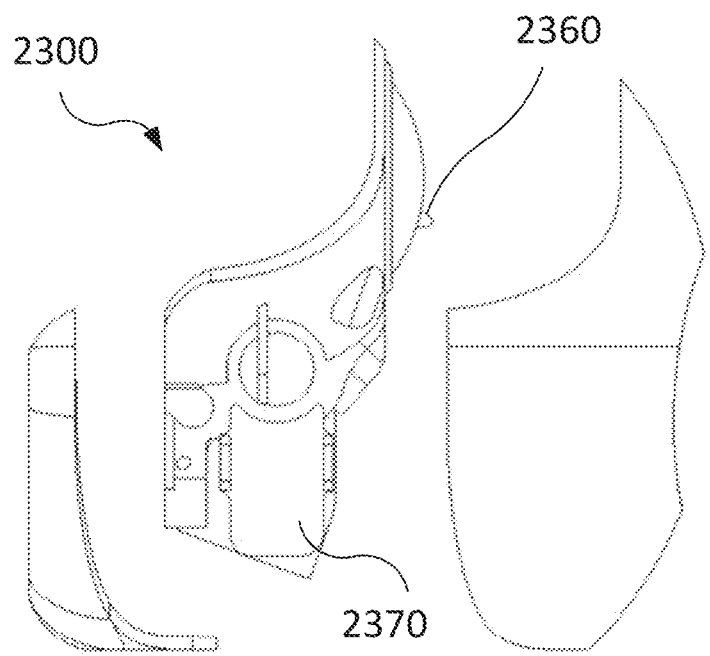
Figure 24A:
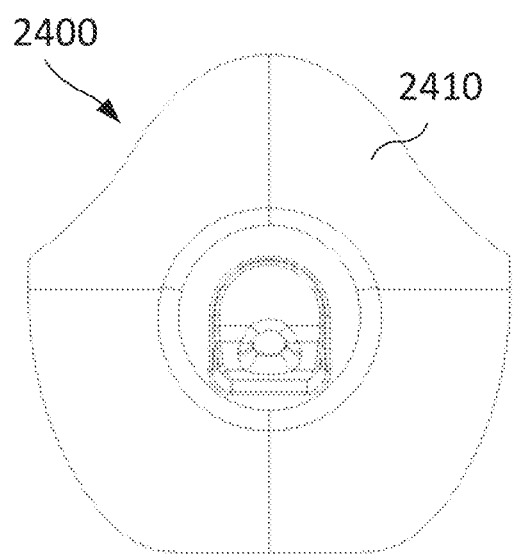
FIGS. 24A to 24E illustrate aspects of a breastmilk pumping and feeding device, in accordance with some embodiments.
Figure 24B:
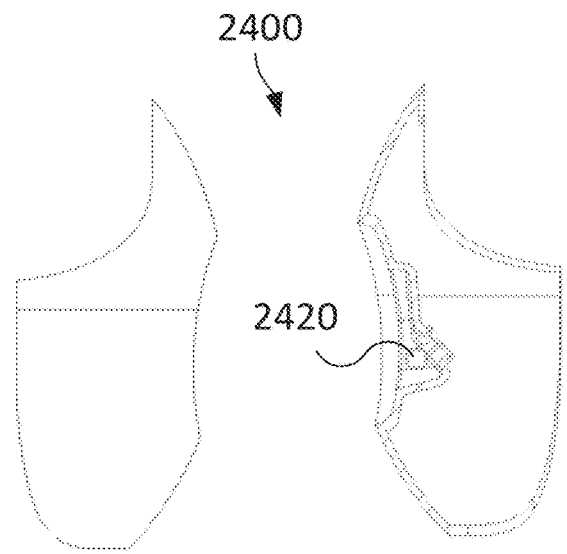
Figure 24C:
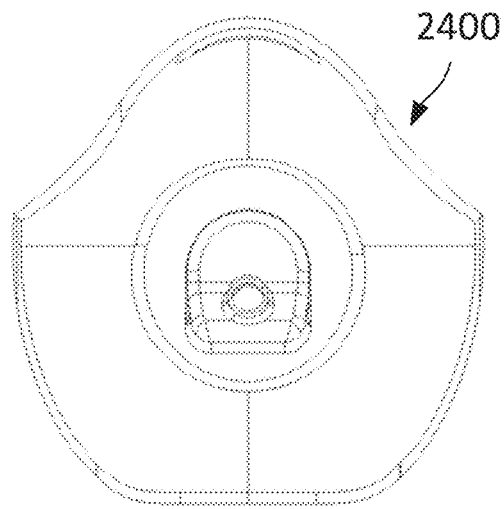
Figure 24D:
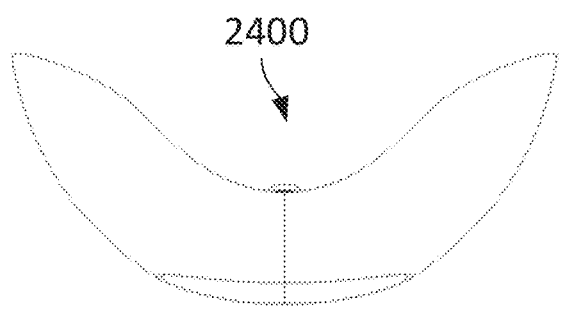
Figure 24E:
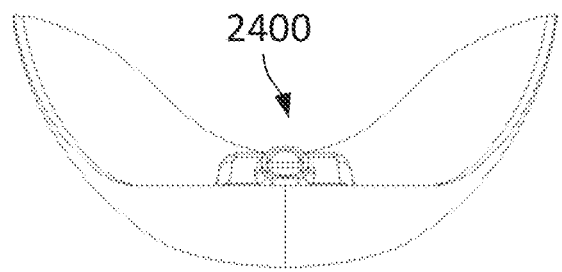

FIGS. 23A and 23B depict aspects of a breastmilk pumping and feeding device 2300, according to embodiments of the present invention. As shown here, a system 2300 or a pump subassembly thereof can include a pump housing back 2310, a pump housing top 2320, a pump housing front 2340, an air pump mounting bracket 2350, a barb 2360 to connect an air pump to a diaphragm cavity, and a peristaltic motor mounting bracket 2370.

FIGS. 24A to 24E depict aspects of a breastmilk pumping and feeding device 2400, according to embodiments of the present invention. As shown here, a system 2400 or a pump subassembly thereof can include a pump housing front 2410 and alignment features 2420 within a cavity which enable a user to insert a nipple subassembly correctly.

FIGS. 25A to 25F depict aspects of a breastmilk pumping and feeding device, according to embodiments of the present invention. As shown here, a system or a container click switch 2500 thereof can include a container click in switch component 2510, a circular cut out 2520 that guides a user to press in a correct contact point, pegs 2530 that allow for the insertion of the switch during device assembly, and rotation when inserted into a top pump housing, a living hinge 2540 that creates a spring action mechanism on the switch, and an angled surface 2550 of the click mechanism that is configured to constrain the motion of a milk container component once attached to a top pump housing.

FIGS. 26A to 26D depict aspects of a pump housing back 2610 of a breastmilk pumping and feeding device, according to embodiments of the present invention.

FIGS. 27A to 27E depict aspects of a pump housing top 2710 of a breastmilk pumping and feeding device, according to embodiments of the present invention. As shown here, a pump housing top 2710 can include a bracket 2720 to connect the pump housing top to other pump housing components, a bracket 2730 to secure a peristaltic pump motor in place, a bracket 2740 to secure an air pump in place, a track 2750 to align a container upon insertion, top features 2760 that allow for a peristaltic motor pump to be assembled in the top housing component, and container alignment features 2770.

Figure 28A:
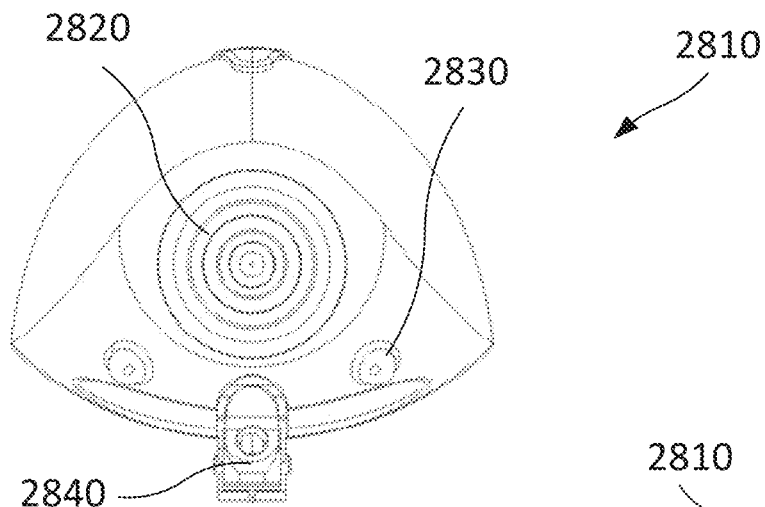
FIGS. 28A to 28C illustrate aspects of a breastmilk pumping and feeding device, in accordance with some embodiments.
Figure 28B:
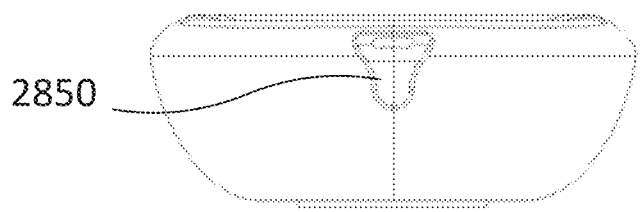
Figure 28C:
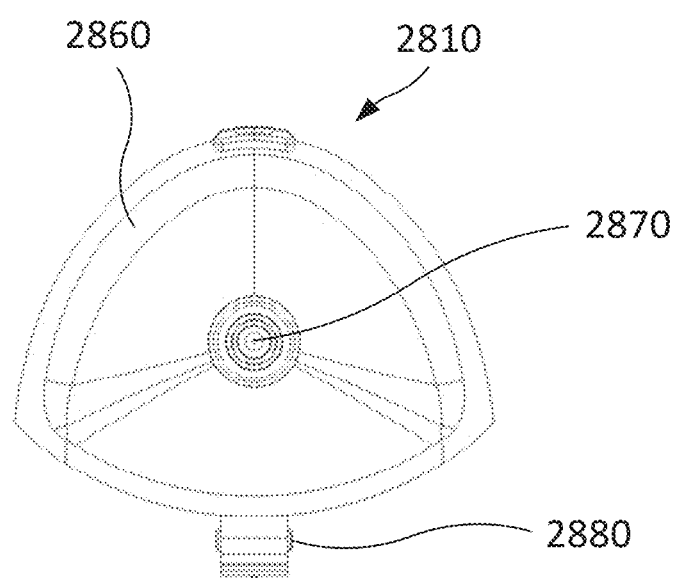

FIGS. 28A to 28C depict aspects of a container subassembly 2810 of a breastmilk pumping and feeding device, according to embodiments of the present invention. As shown here, a container subassembly 2810 can include a diaphragm 2820 that contracts into a cavity to create negative pressure, which facilitates suction at the breast. Container subassembly 2810 can also include container alignment features 2830 that click in to alignment features on a pump housing top, and alignment features 2840 for a fluid connection assembly, which is inserted onto the milk container. Further, container subassembly 2810 can include a spout cap 2850 for a milk container. Container subassembly 2810 can also include breast flange seals 2860 around the edge of the milk container, and an axis of the user's nipple can align with an axis 2870 of the diaphragm. Container subassembly 2810 can further include pegs 2880 on the side of the container which can slide into a track system on a top pump housing.

Figures 29A, 29B:
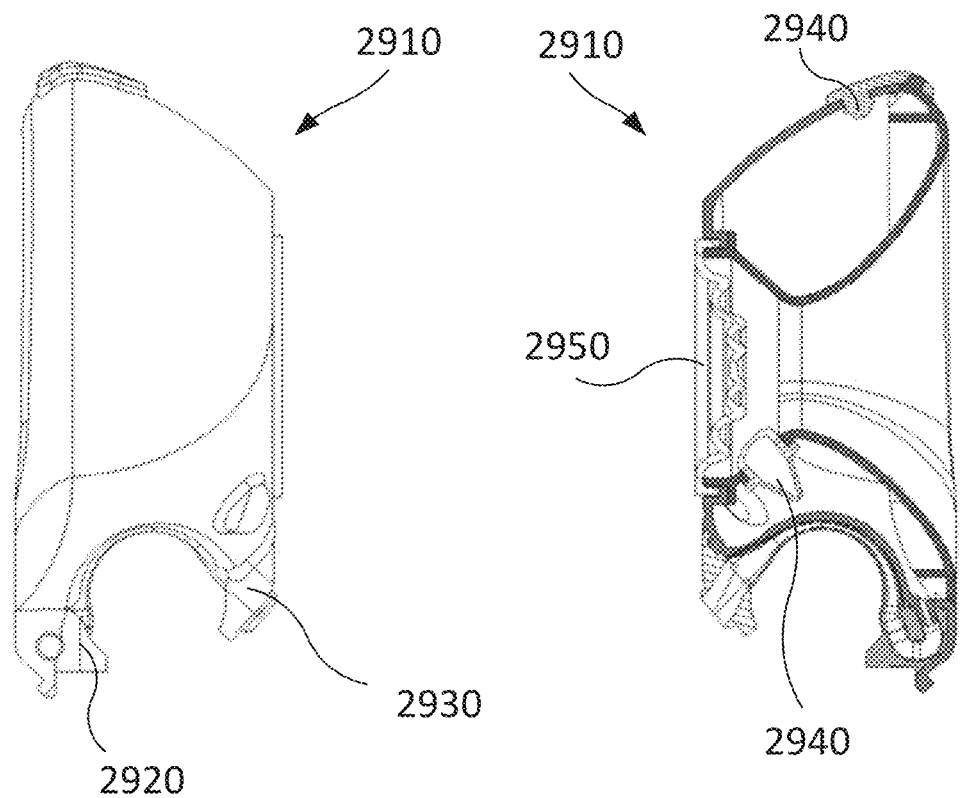
FIGS. 29A to 29C illustrate aspects of a breastmilk pumping and feeding device, in accordance with some embodiments.
Figure 29C:
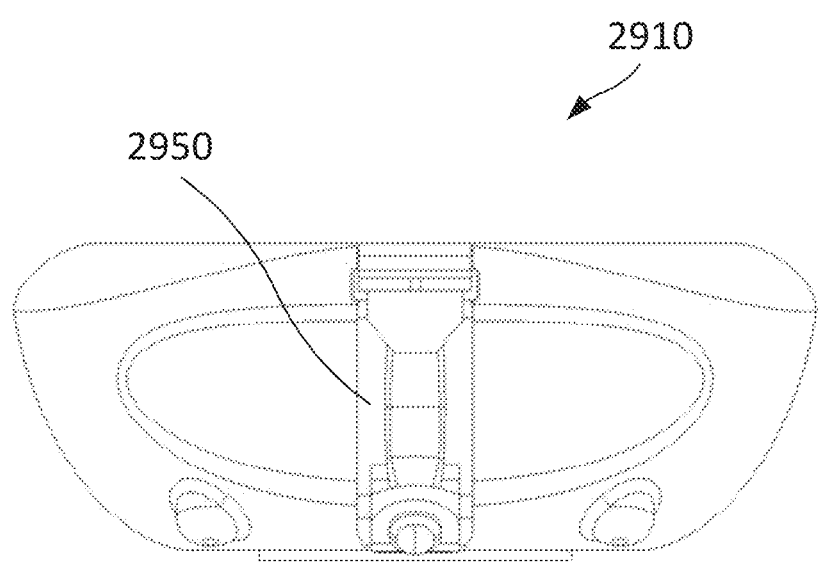

FIGS. 29A to 29C depict aspects of a container subassembly 2910 of a breastmilk pumping and feeding device, according to embodiments of the present invention. As shown here, a container subassembly 2910 can include a fluid connection tube 2920 that can be inserted into the bottom of a milk container, and a through plug 2930 that can attach to the front of a milk storage container, and that connect with a nipple component in the front of the device. Container subassembly 2910 can also include a one way duckbill valve 2940 that allows milk to pass from the breast flange to the container, but not the reverse. Further, container subassembly 2910 can include a cutout 2950 in the bottom of the milk container that allows for the fluid connection to be compressed by the peristaltic wheel, thereby creating pumping action.

Figure 30A:
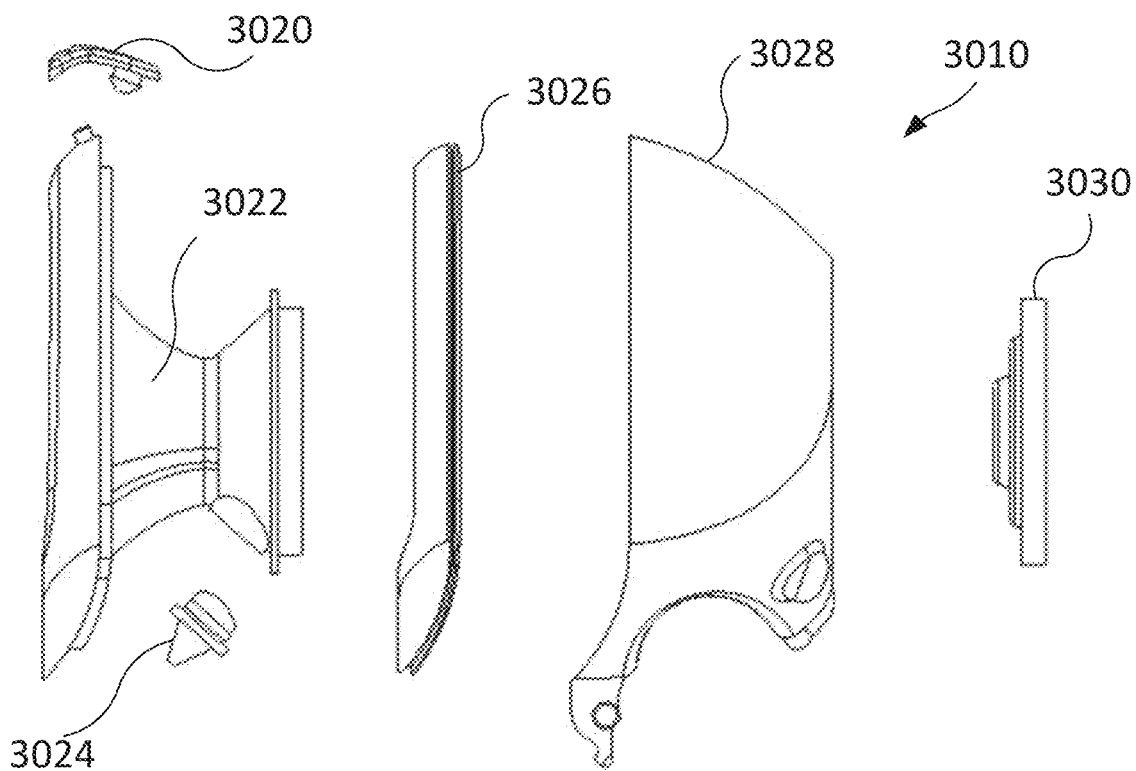
FIGS. 30A and 30B illustrate aspects of a breastmilk pumping and feeding device, in accordance with some embodiments.
Figure 30B:
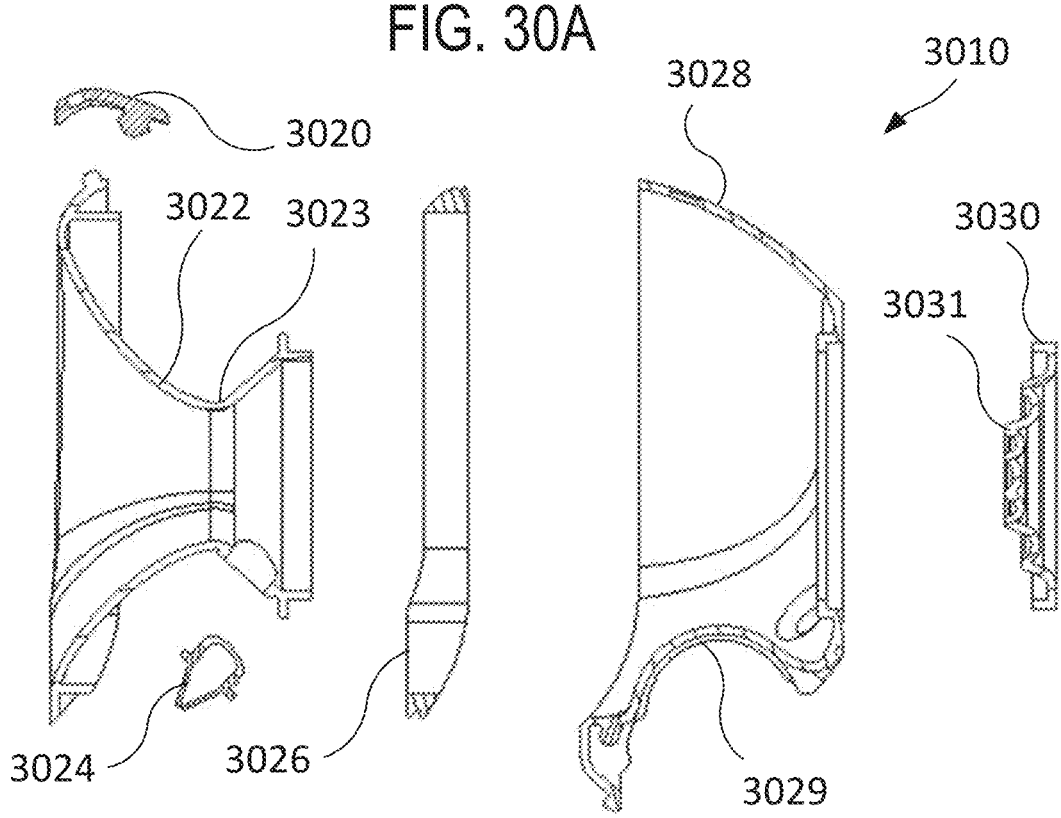

FIGS. 30A and 30B provide exploded and exploded cross-section views, respectively, of a container subassembly 3010. As depicted here, container subassembly 3010 includes a spout cap 3020, a breast flange 3022, a duckbill valve 3024, a flange seal 3026, a milk container 3028, and a diaphragm pump 3030. The breast flange 3022 can be curved to accommodate the natural anatomy of a breast, with a constriction point 3023 to facilitate expression. The duckbill valve 3024 can be a one way valve that fits into the breast flange 3022, creating a seal for suction. The milk container 3028 can have a cutout 3029 in the bottom thereof that allows for a fluid connection piece to compress. The diaphragm pump 3030 can have ridges 3031, which can allows for linear compression and/or collapsibility.

Figure 31A:
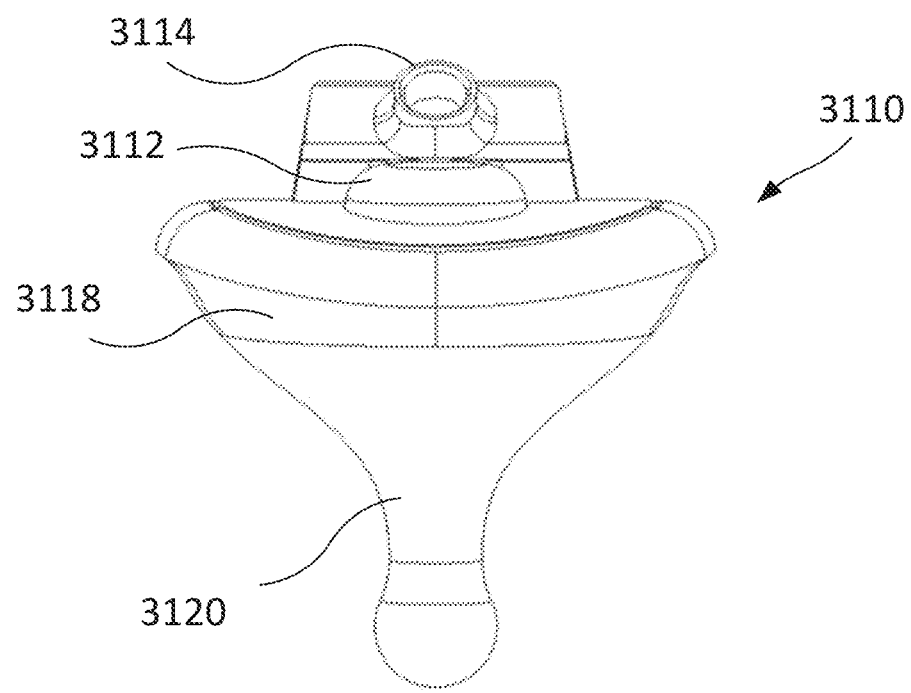
FIGS. 31A to 31C illustrate aspects of a breastmilk pumping and feeding device, in accordance with some embodiments.
Figures 31B, 31C:
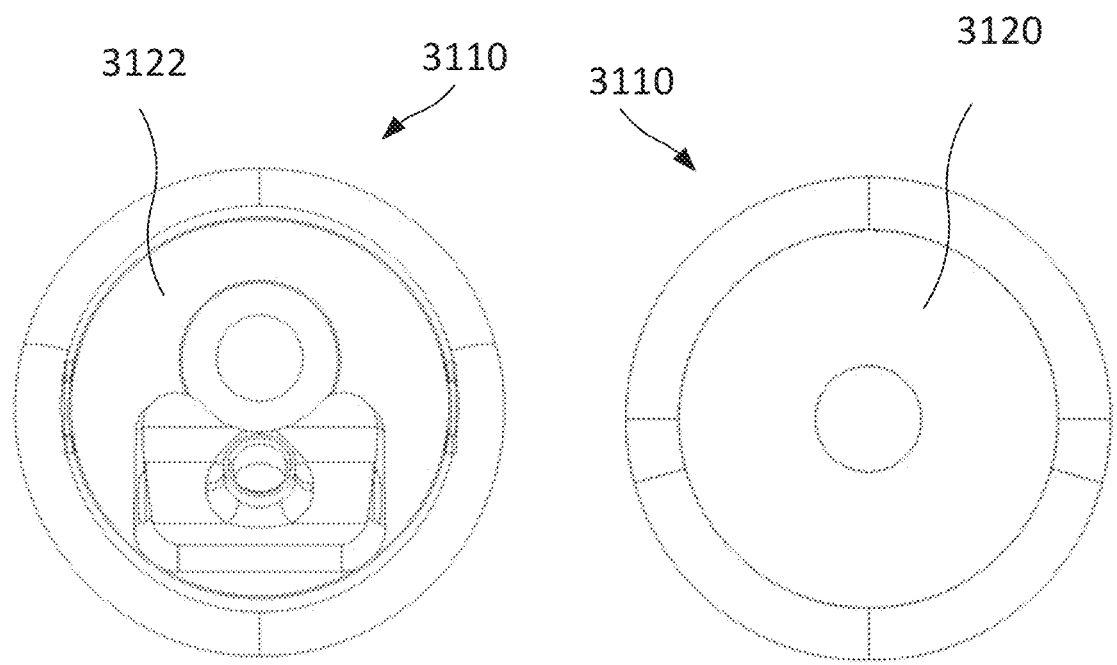

FIGS. 31A to 31C depict aspects of a nipple component subassembly 3110 of a breastmilk pumping and feeding device, according to embodiments of the present invention. As shown here, a nipple component subassembly 3110 can include a feedbag 3112 that extends beyond the back of the nipple component, a fluid connection point 3114 that connects the fluid path to the nipple component subassembly, a nipple ring component having a front 3118 that clicks into the front of a pump housing, and a nipple 3120 that is made of soft silicone and seals with the front of the nipple ring component. A back 3122 of the nipple ring components can connect with a front of the nipple ring component. The nipple 3120 can be symmetrical, and may not require alignment by the user when inserting into the nipple ring subassembly.

Figure 32A:
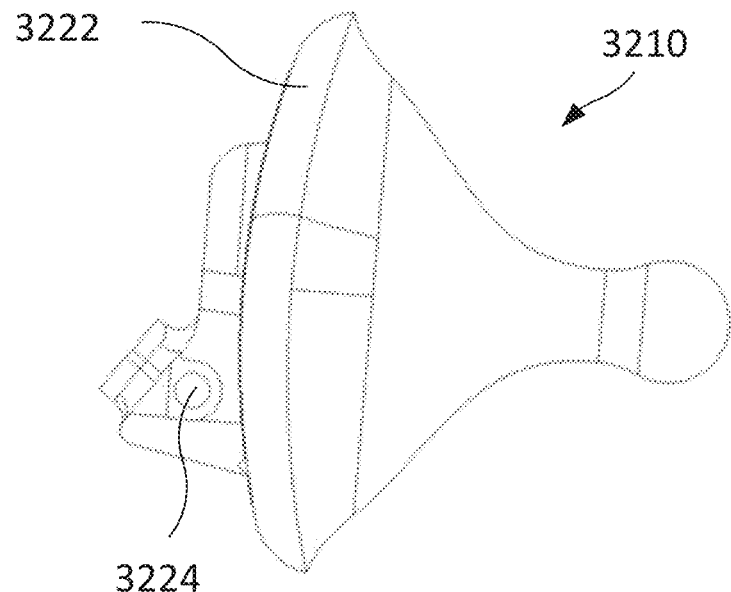
FIGS. 32A and 32B illustrate aspects of a breastmilk pumping and feeding device, in accordance with some embodiments.
Figure 32B:
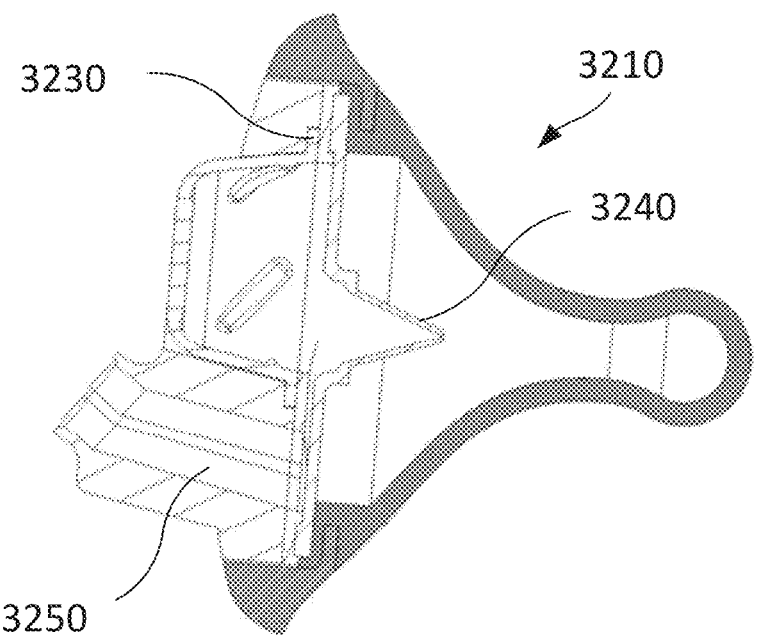

FIGS. 32A and 32B depict aspects of a nipple component subassembly 3210 of a breastmilk pumping and feeding device, according to embodiments of the present invention. As shown here, a nipple component subassembly 3210 can have a rounded back 3222 that fits with a rounded cavity in a pump subassembly, and an alignment mechanism 3224 in the back of a nipple ring component that allows for a secure alignment of the nipple component subassembly in the pump housing. A feedbag component 3230 can be overmolded into the back of the nipple ring component. The one way duckbill valve 3240 can be compressed by the nipple and the back of the nipple ring component. A fluid path connection 3250 can transfer breast milk from the container to the feedbag.

Figure 33:
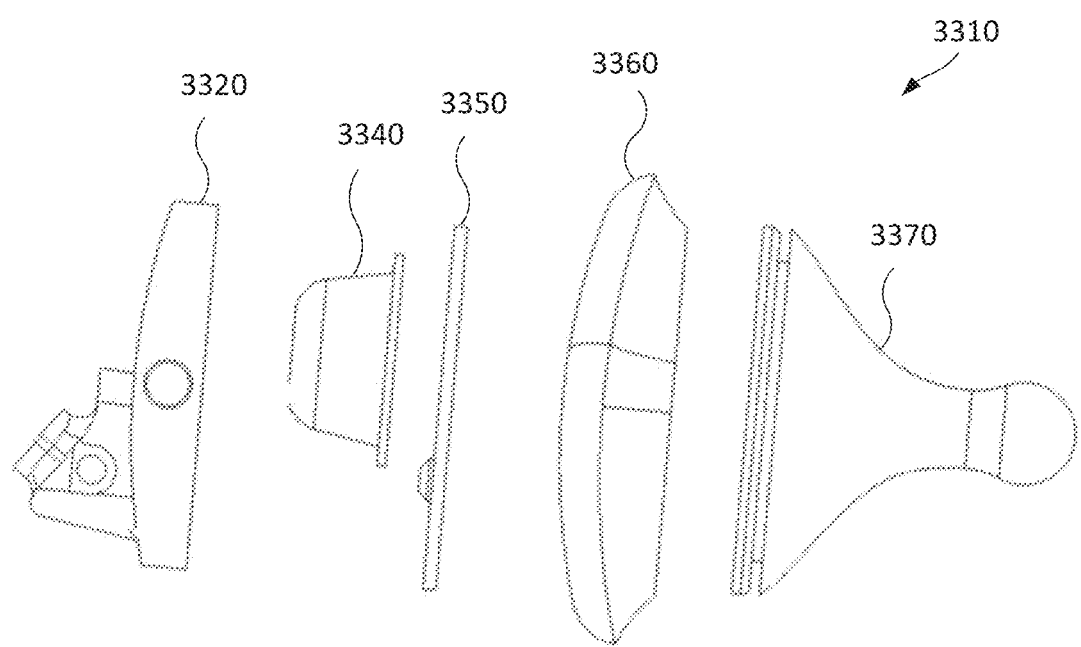
FIG. 33 illustrates aspects of a breastmilk pumping and feeding device, in accordance with some embodiments.
Figure 34A:
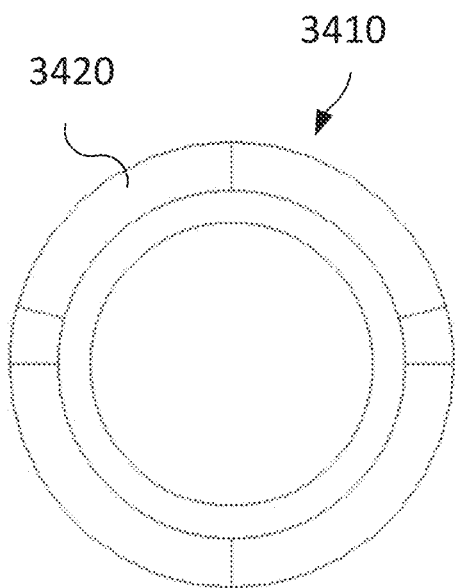
FIGS. 34A to 34E illustrate aspects of a breastmilk pumping and feeding device, in accordance with some embodiments.
Figure 34B:
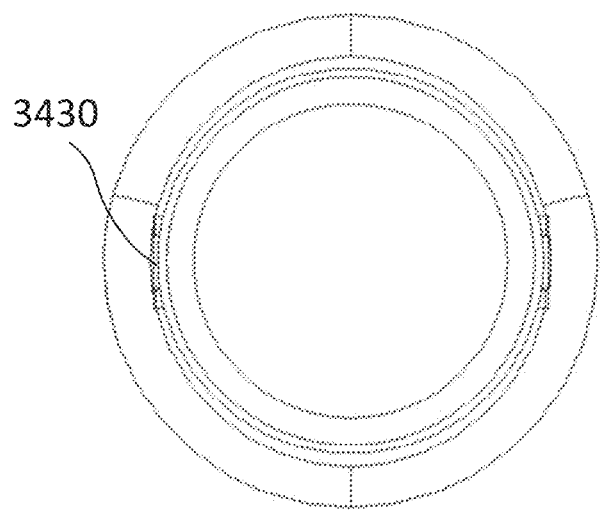
Figure 34C:
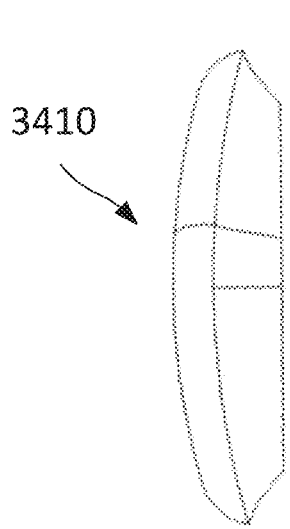
Figure 34D:
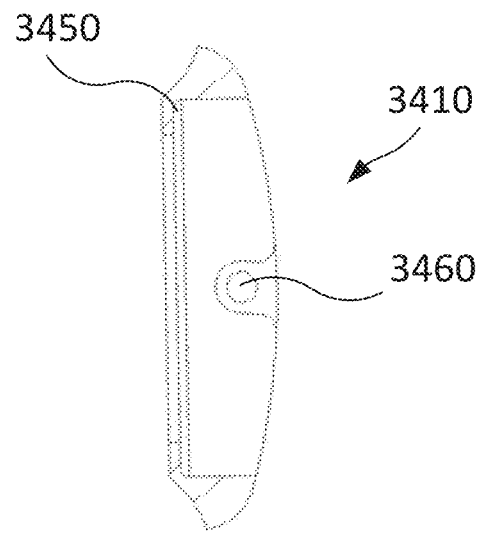
Figure 34E:
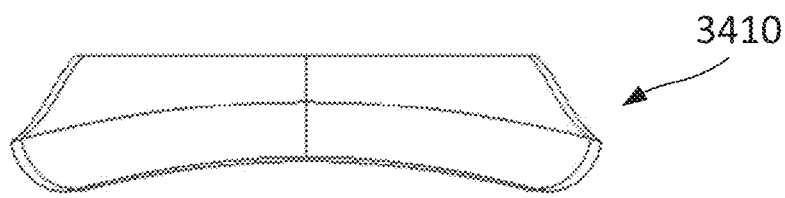
Figure 35A:
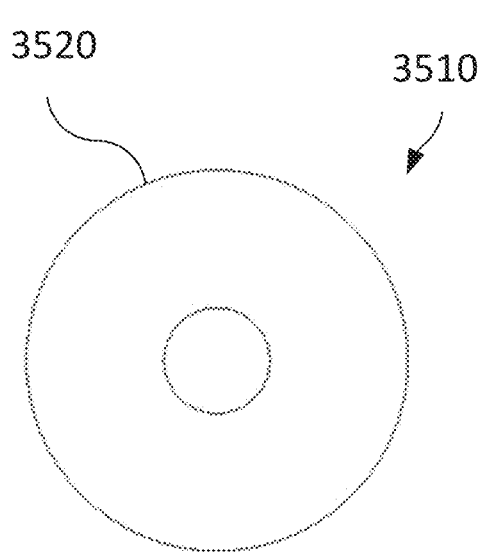
FIGS. 35A to 35D illustrate aspects of a breastmilk pumping and feeding device, in accordance with some embodiments.
Figure 35B:
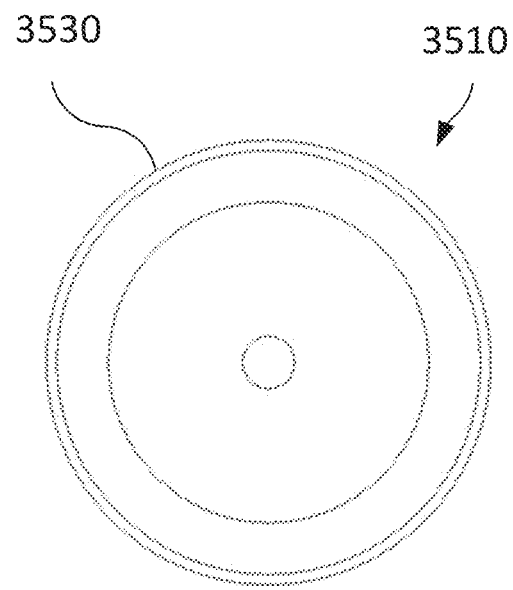
Figure 35C:
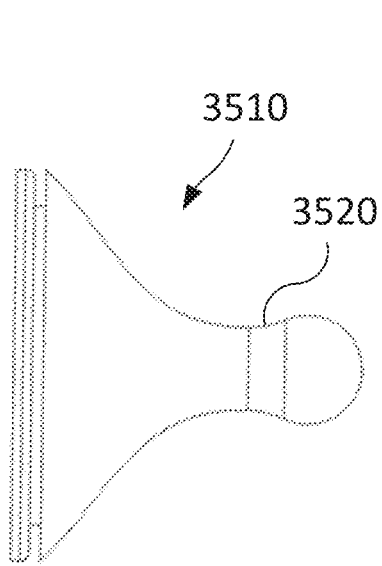
Figure 35D:
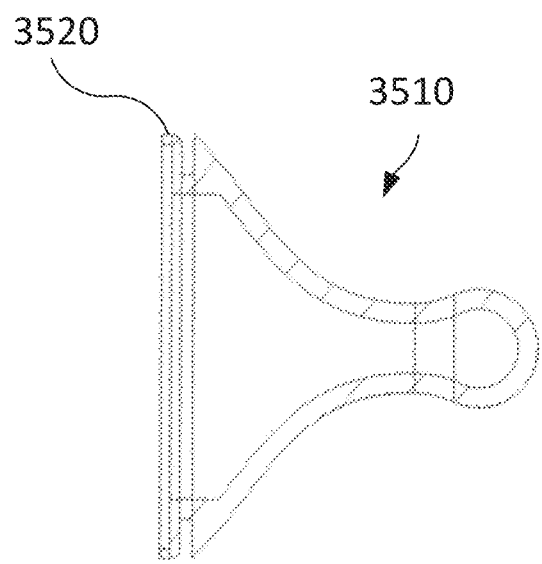
Figure 36A:
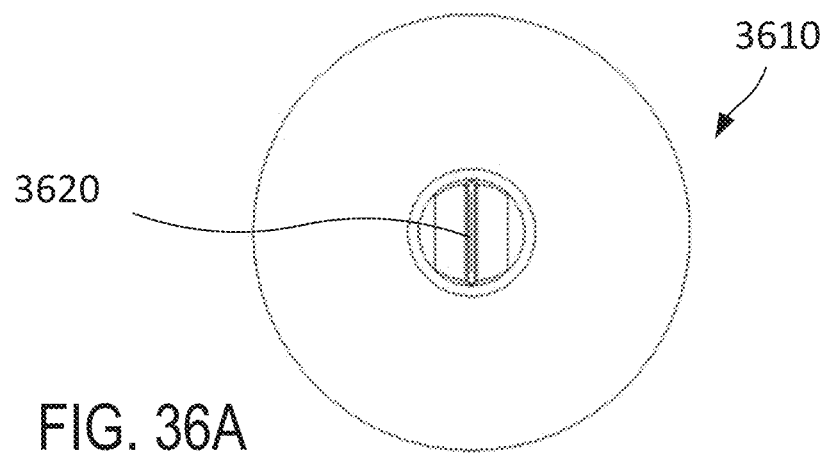
FIGS. 36A to 36D illustrate aspects of a breastmilk pumping and feeding device, in accordance with some embodiments.
Figure 36B:
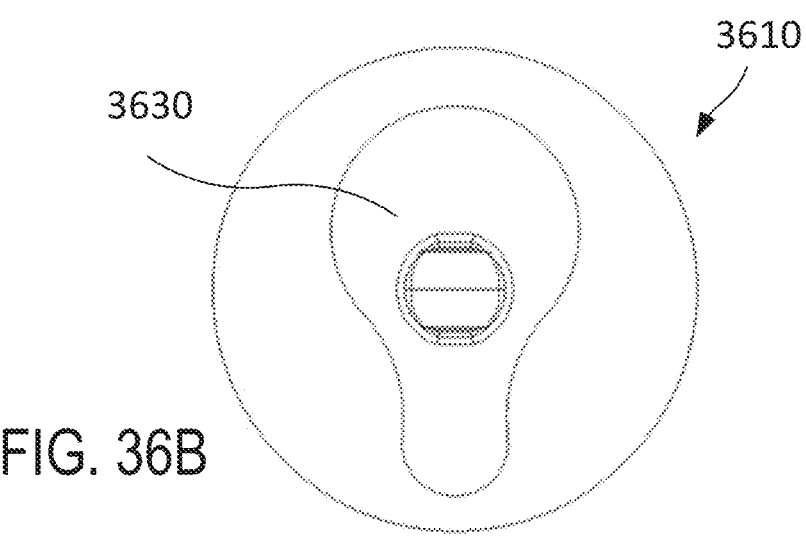
Figure 36C:
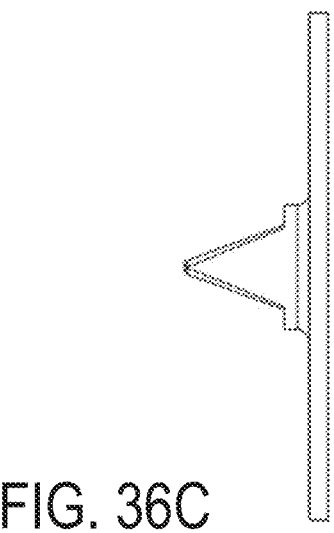
Figure 36D:
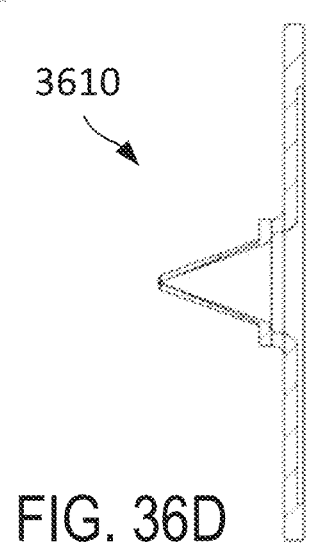
Figure 37A:
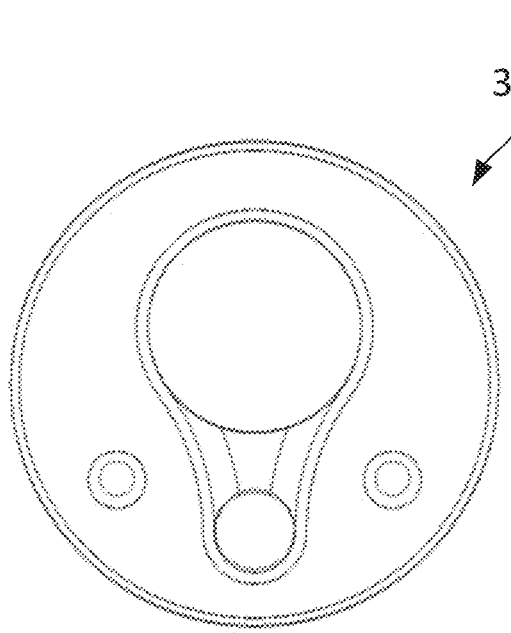
FIGS. 37A to 37D illustrate aspects of a breastmilk pumping and feeding device, in accordance with some embodiments.
Figure 37B:
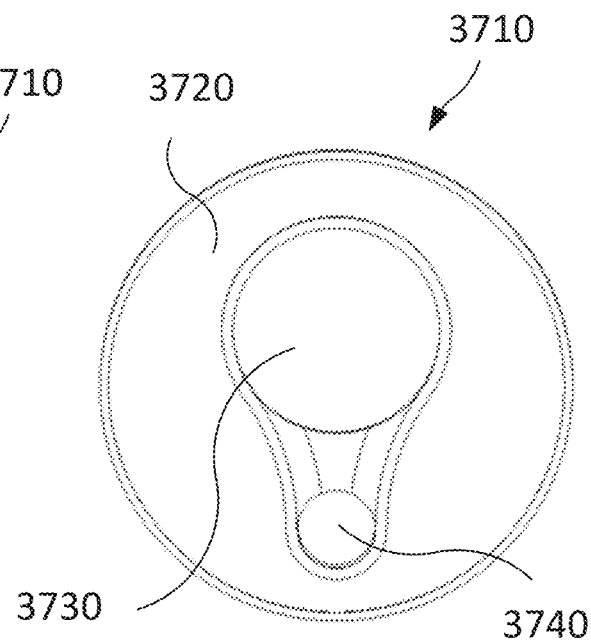
Figure 37C:
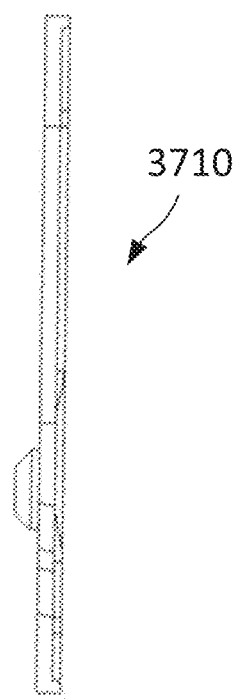
Figure 37D:
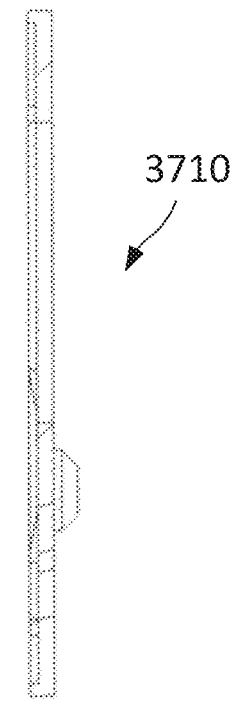
Figure 38A:
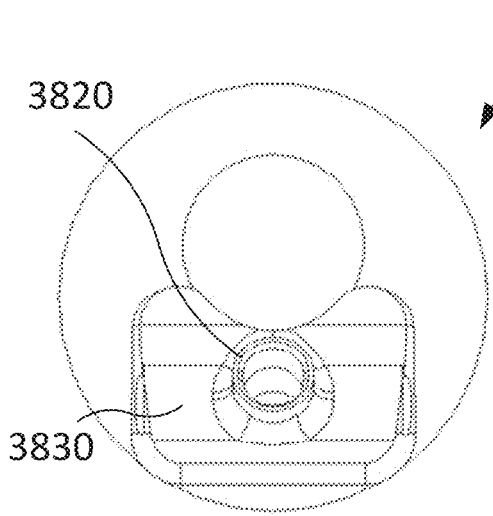
FIGS. 38A to 38F illustrate aspects of a breastmilk pumping and feeding device, in accordance with some embodiments.
Figure 38B:
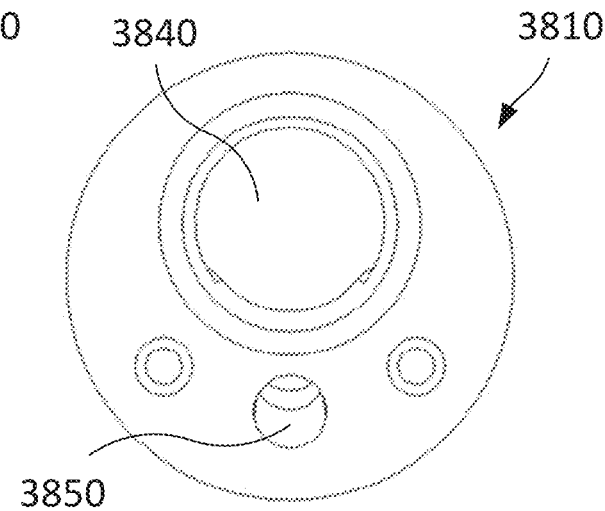
Figure 38C:
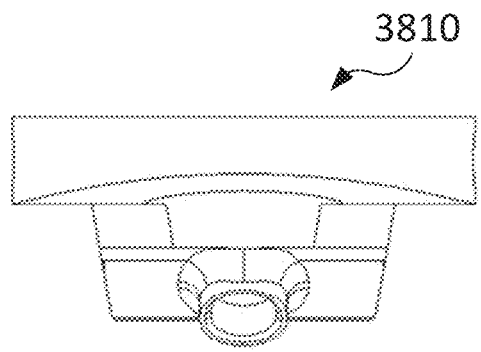
Figure 38D:
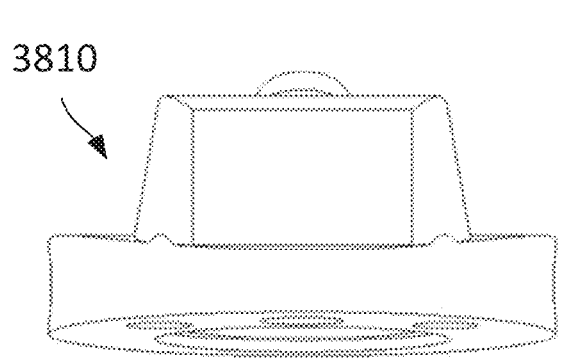
Figure 38E:
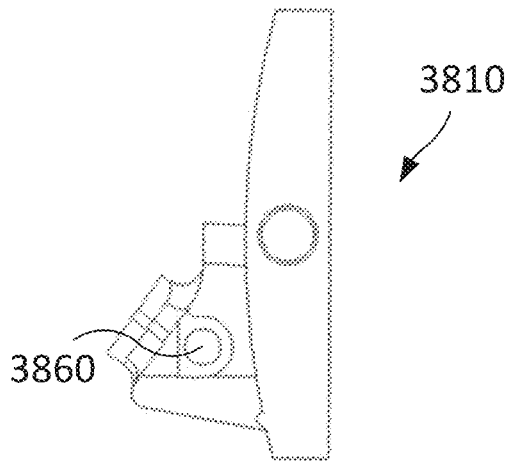
Figure 38F:
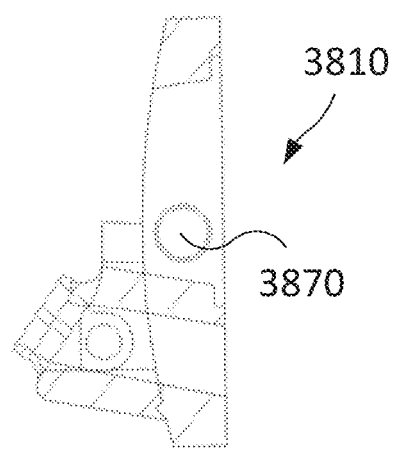

FIG. 33 depicts aspects of a nipple component subassembly 3310 of a breastmilk pumping and feeding device, according to embodiments of the present invention. As shown here, a nipple component subassembly 3310 can have a nipple ring component (first back portion) 3320, a feedbag component 3340, a nipple ring component (second back portion) 3350, a nipple ring component (front portion) 3360, and a nipple component 3370.

FIGS. 34A to 34E depict aspects of a nipple ring component (front) 3410 of a breastmilk pumping and feeding device, according to embodiments of the present invention. As shown here, nipple ring component (front) 3410 can have a front 3420, one or more retaining features 3430 that allow the back component of the nipple ring to be inserted into the front component, a lip 3450 on the front nipple ring that allows for a seal to be created on the nipple, and retaining features 3460.

FIGS. 35A to 35D depict aspects of a nipple component 3510 of a breastmilk pumping and feeding device, according to embodiments of the present invention. As shown here, nipple component 3510 has a circular profile 3520 that is well suited for babies to drink breastmilk therefrom. A bulbous side profile 3530 is well suited for babies to drink breastmilk therefrom. Lip features 3540 on the nipple allow for a seal to be created by the front component of the nipple ring.

FIGS. 36A to 36D depict aspects of a valve such as a one way duckbill valve 3610 of a breastmilk pumping and feeding device, according to embodiments of the present invention. As shown here, one way duckbill valve 3610 has a slit opening 3620 that allows fluid to pass through in one direction only. A one way valve such as a duckbill valve 3610 also has a back cutout 3630 with a shape that allows for fluid to move from a fluid connection path to a feedbag. Fluid can pass through the duckbill valve, but vacuum created by peristaltic action does not allow fluid to pass back through the valve.

FIGS. 37A to 37D depict aspects of a nipple ring component (second back portion) 3710 of a breastmilk pumping and feeding device, according to embodiments of the present invention. As shown here, nipple ring component (second back portion) 3710 includes one or more alignment features 3720 for a one way valve such as a duckbill valve which allow the user to insert the duckbill valve in the desired orientation, an opening 3730 for the feedbag components, and an opening 3740 for the fluid path connection component.

FIGS. 38A to 38F depict aspects of a nipple ring component (first back portion) 3810 of a breastmilk pumping and feeding device, according to embodiments of the present invention. As shown here, nipple ring component (first back portion) 3810 includes a fluid path connection 3820 on the back side thereof, as well as a protrusion 3830 on the back side thereof which serves as a feature for aligning the nipple assembly in the pump housing cavity. Further, the nipple ring component (first back portion) 3810 includes an opening 3840 for the feedbag component, an opening 3850 for the fluid path connection component, one or more channels 3860 on the back side thereof which allow for the subassembly to be aligned as desired in the nipple cavity on the pump housing, and one or more alignment features 3870 which secure the back component of the nipple into the front component.

Figure 39A:
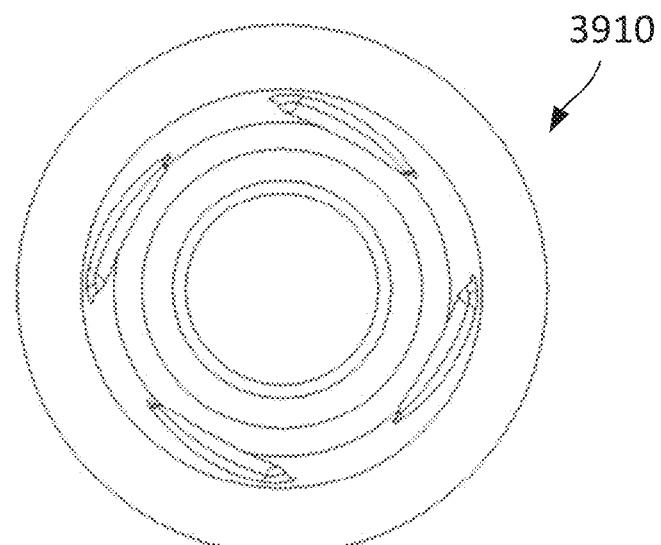
FIGS. 39A to 39C illustrate aspects of a breastmilk pumping and feeding device, in accordance with some embodiments.
Figure 39B:
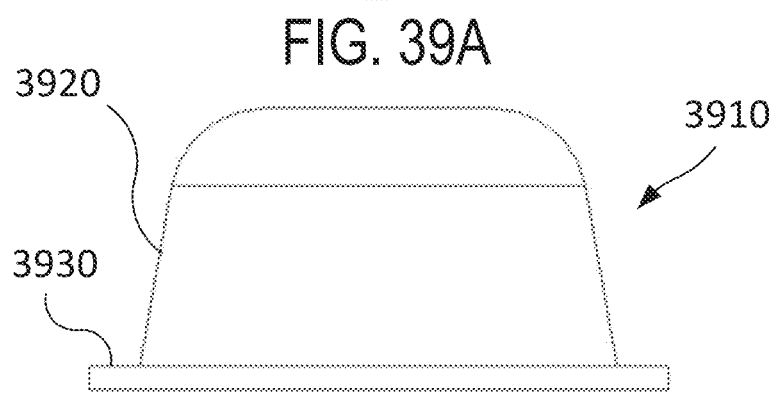
Figure 39C:
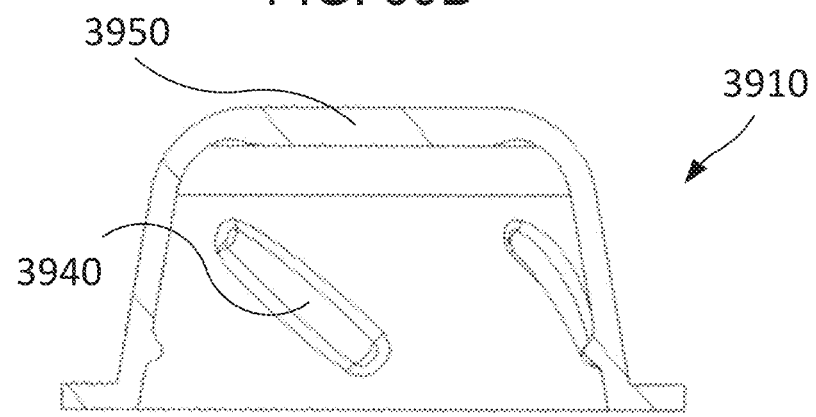
Figure 40A:
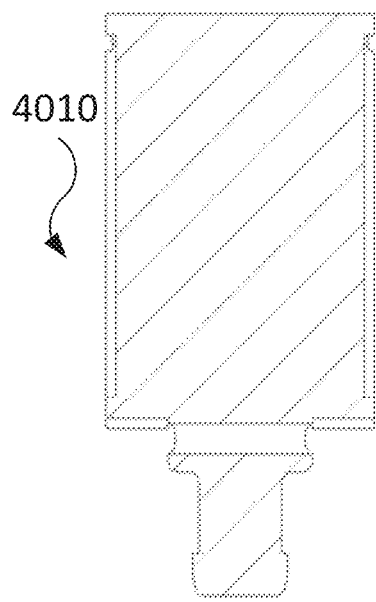
FIGS. 40A to 40E illustrate aspects of a breastmilk pumping and feeding device, in accordance with some embodiments.
Figure 40B:
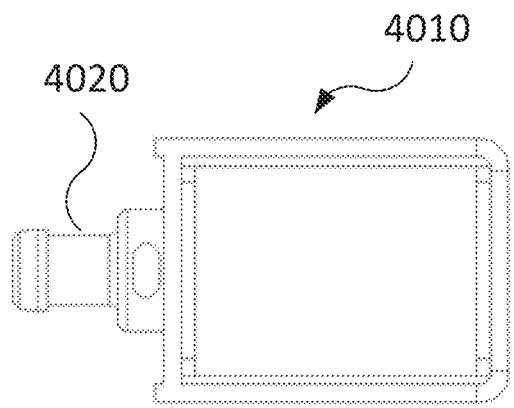
Figure 40C:
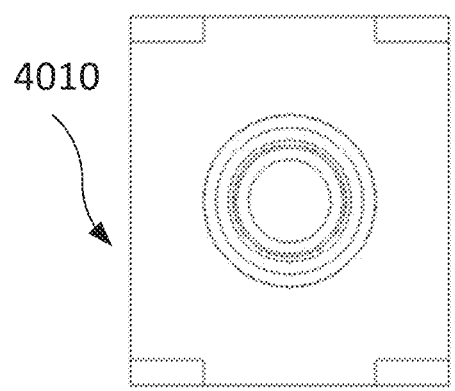
Figure 40D:
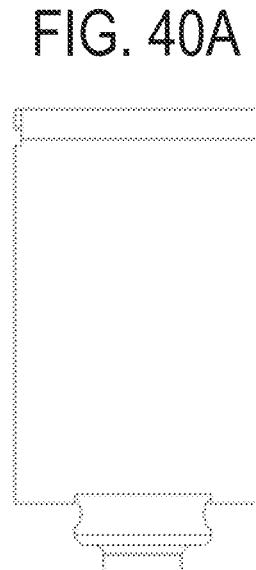
Figure 40E:
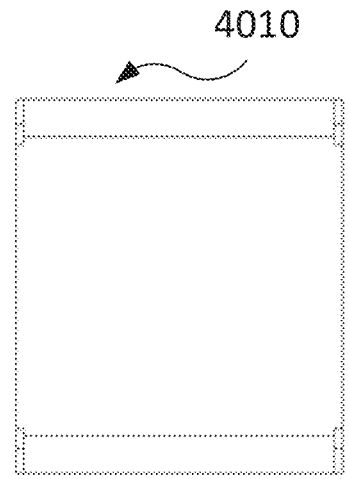
Figure 41A:
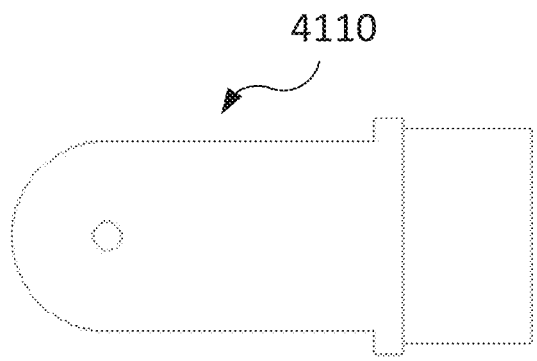
FIGS. 41A to 41F illustrate aspects of a breastmilk pumping and feeding device, in accordance with some embodiments.
Figure 41B:
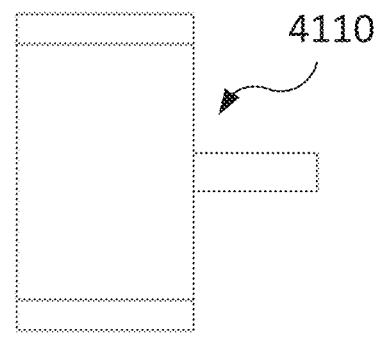
Figure 41C:
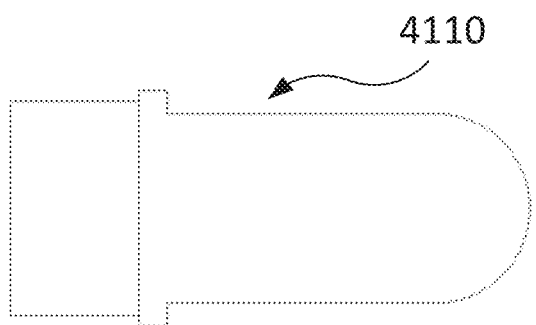
Figure 41D:
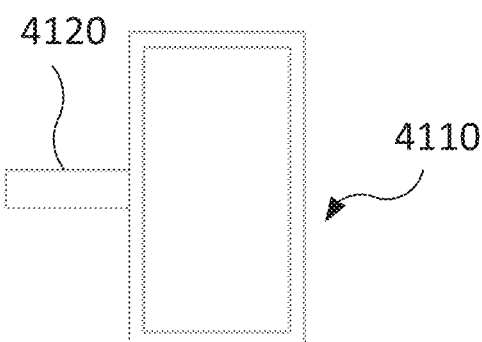
Figure 41E:
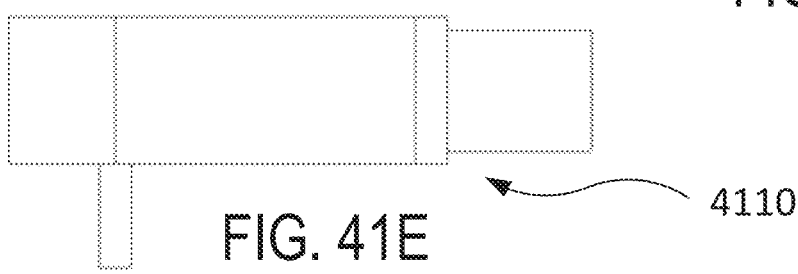
Figure 41F:
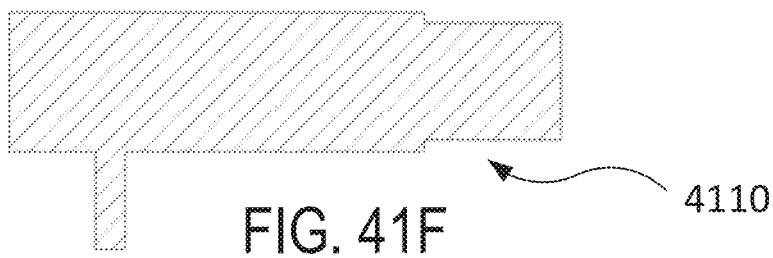
Figure 42A:
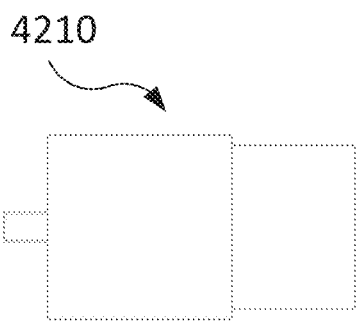
FIGS. 42A to 42G illustrate aspects of a breastmilk pumping and feeding device, in accordance with some embodiments.
Figure 42B:
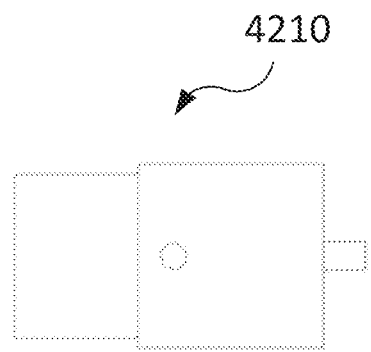
Figure 42C:
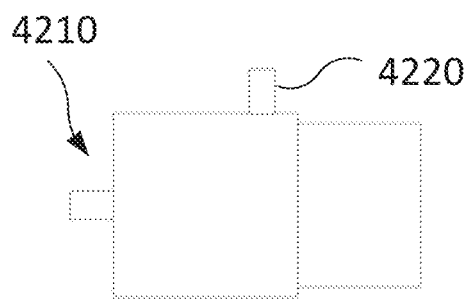
Figure 42D:
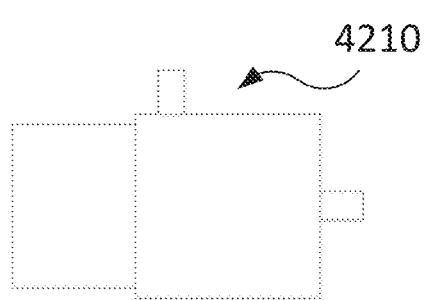
Figure 42E:
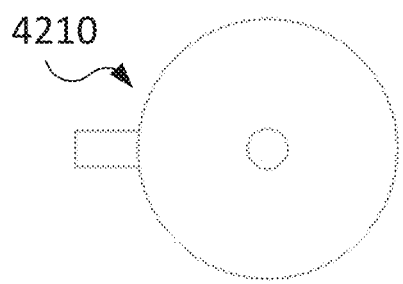
Figure 42F:
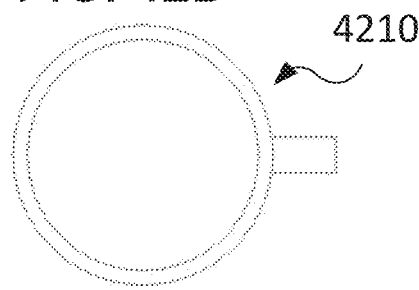
Figure 42G:
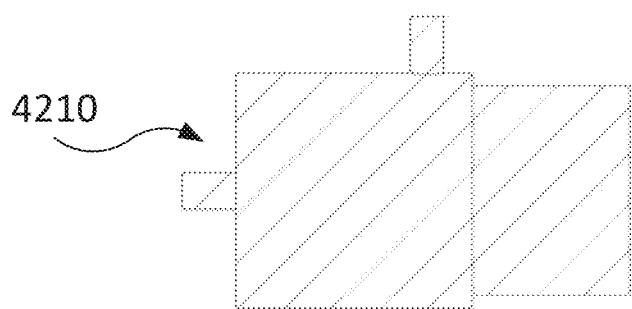

FIGS. 39A to 39C depict aspects of a feedbag component 3910 of a breastmilk pumping and feeding device, according to embodiments of the present invention. As shown here, feedbag component 3910 includes an angled profile 3920 that allows for easy insertion into a pump housing cavity, a lip feature 3930 that allows for overmolding, rib features 3940 on the interior of the feedbag which ensure that the component compresses along a linear axis, and a top portion 3950 that is thicker than the rest of the feedbag body, allowing for a magnet to be molded in place.

FIGS. 40A to 40E depict aspects of a solenoid valve component 4010 of a breastmilk pumping and feeding device, according to embodiments of the present invention. As shown here, solenoid valve component 4010 includes a barb 4020 that allows for connection to an air pump, thus allowing vacuum pressure to be released periodically.

FIGS. 41A to 41F depict aspects of a peristaltic pump motor 4110 of a breastmilk pumping and feeding device, according to embodiments of the present invention. As shown here, peristaltic pump motor 4110 includes a motor axis 4120 that can slot directly into a peristaltic wheel carrier component.

FIGS. 42A to 42G depict aspects of an air pump motor 4210 of a breastmilk pumping and feeding device, according to embodiments of the present invention. As shown here, air pump motor 4210 includes a connection mechanism 4220 that allows the air pump to connect via tubing to the barb feature on the cavity of the front pump housing.

Figure 43A:
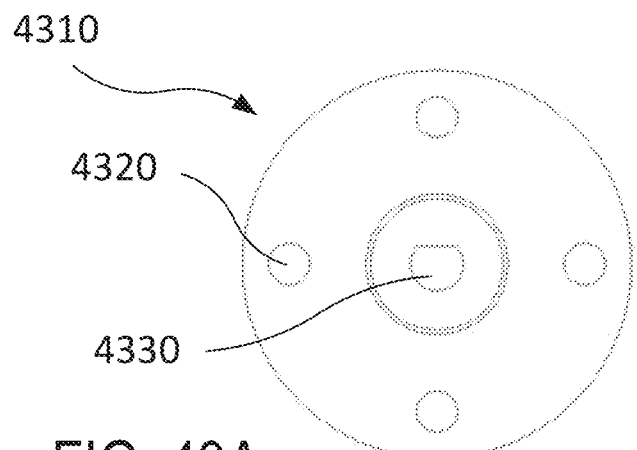
FIGS. 43A to 43C illustrate aspects of a breastmilk pumping and feeding device, in accordance with some embodiments.
Figure 43B:
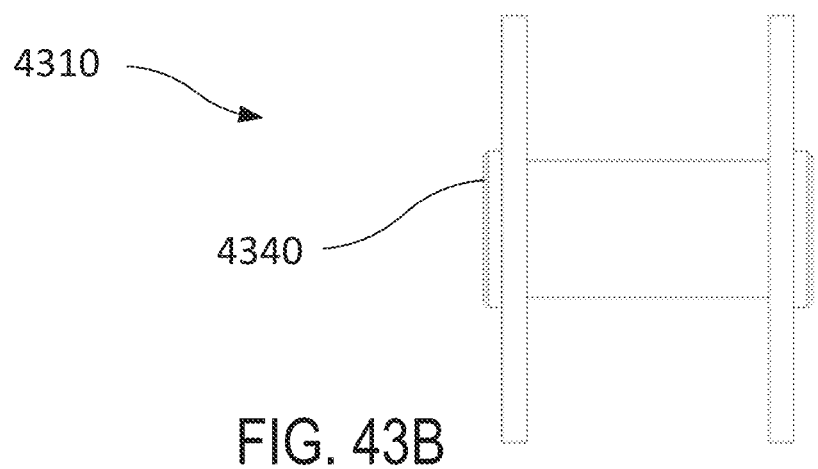
Figure 43C:
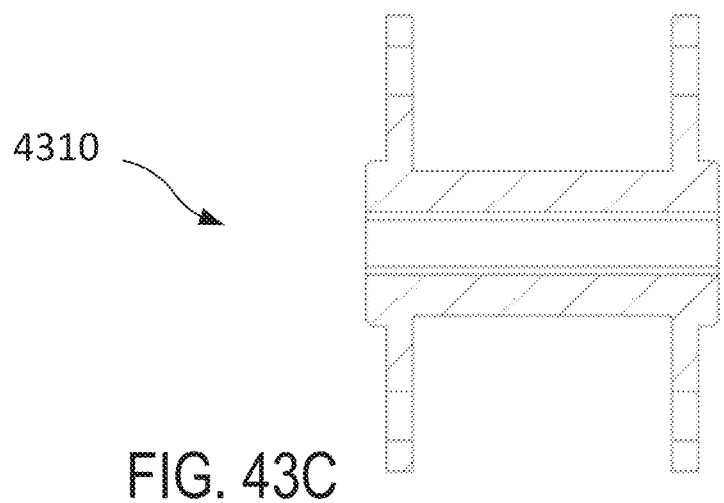

FIGS. 43A to 43C depict aspects of a peristaltic wheel carrier component 4310 of a breastmilk pumping and feeding device, according to embodiments of the present invention. As shown here, peristaltic wheel carrier component 4310 includes one or more holes 4320 to align and connect individual peristaltic roller components (e.g. 4 in total), a hole 4330 to insert a peristaltic motor shaft therein, and one or more protrusions 4340 that allow for alignment within friction reducing ball bearings or bushings.

Figure 44A:
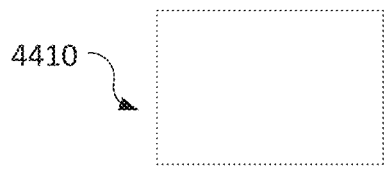
FIGS. 44A to 44C illustrate aspects of a breastmilk pumping and feeding device, in accordance with some embodiments.
Figure 44B:
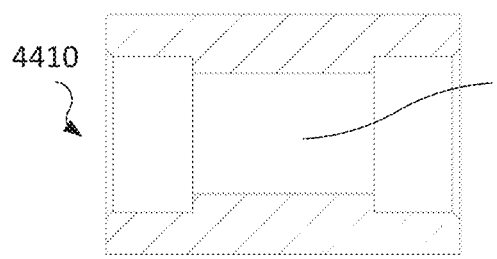
Figure 44C:
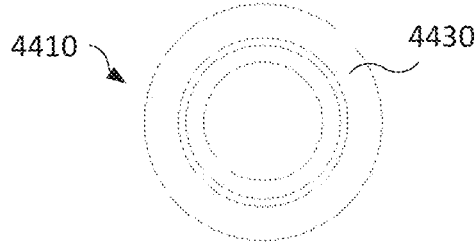

FIGS. 44A to 44C depict aspects of a peristaltic wheel roller 4410 of a breastmilk pumping and feeding device, according to embodiments of the present invention. As shown here, peristaltic wheel roller 4410 includes peristaltic rollers 4420 connected to a peristaltic wheel carrier component via ball bearing (or bushing component) and dowel pin elements. In some cases, the connection is via a bushing mechanism. In some cases, the connection includes a lubricious material. Peristaltic wheel roller 4410 can have a circular profile 4430 that creates minimal friction when compressing the peristaltic tubing.

Figure 45A:
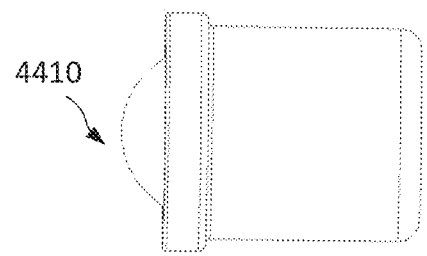
FIGS. 45A and 45B illustrate aspects of a breastmilk pumping and feeding device, in accordance with some embodiments.
Figure 45B:
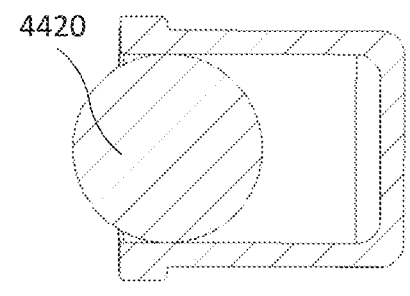

FIGS. 45A and 45B depict aspects of a ball detent component 4510 of a breastmilk pumping and feeding device, according to embodiments of the present invention. As shown here, ball detent component 4510 includes a spring loaded ball detent mechanism 4520 that allows for alignment and securing of components in place.

Figure 46:
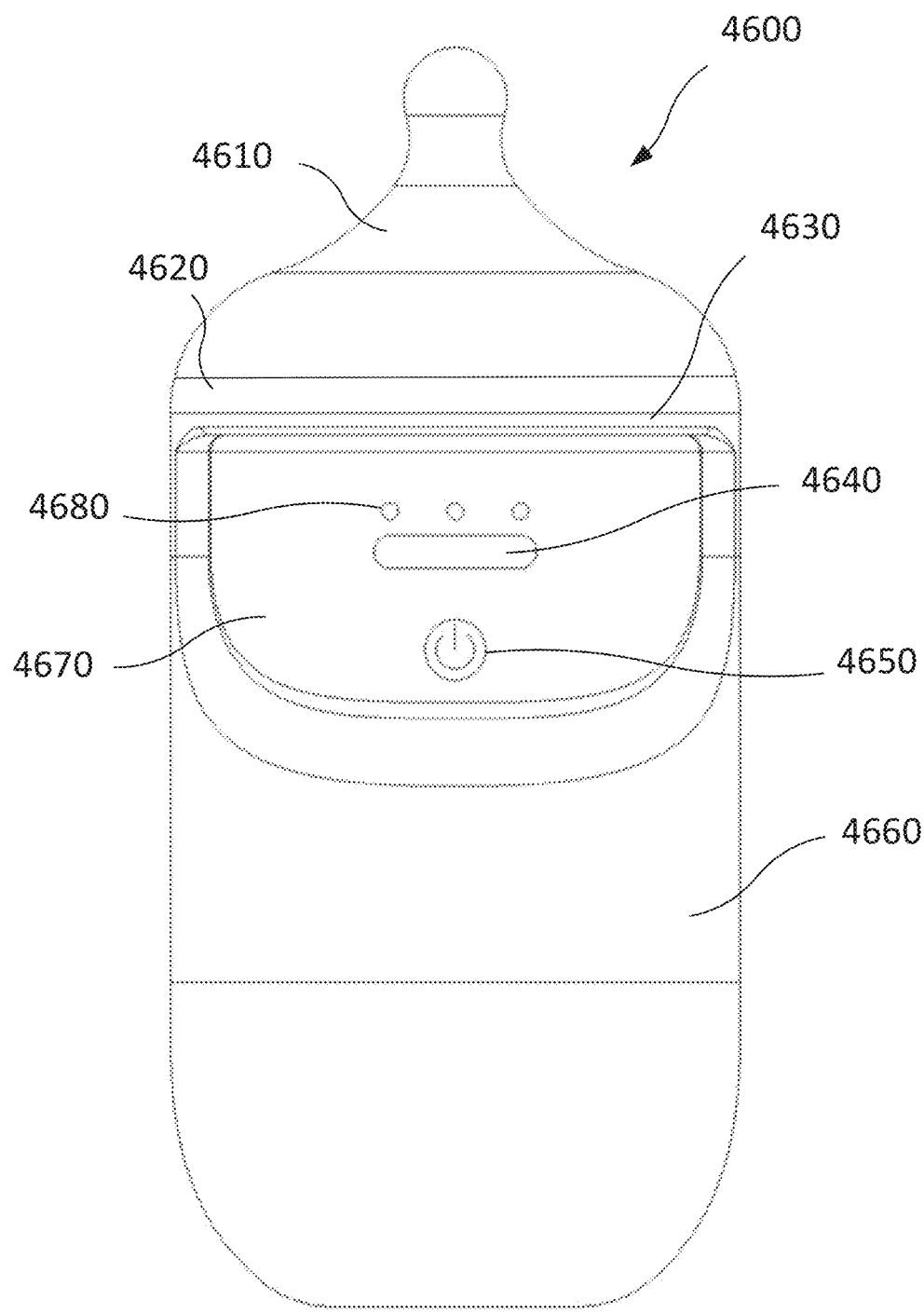
FIG. 46 illustrates aspects of a breastmilk pumping and feeding device, in accordance with some embodiments.
Figure 47A:
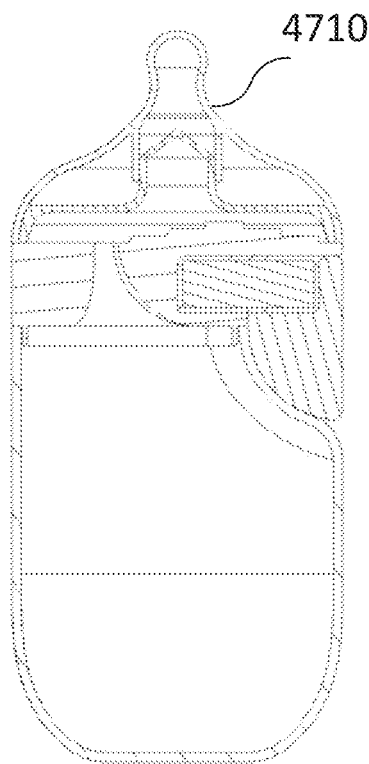
FIGS. 47A to 47D illustrate aspects of a breastmilk pumping and feeding device, in accordance with some embodiments.
Figure 47B:
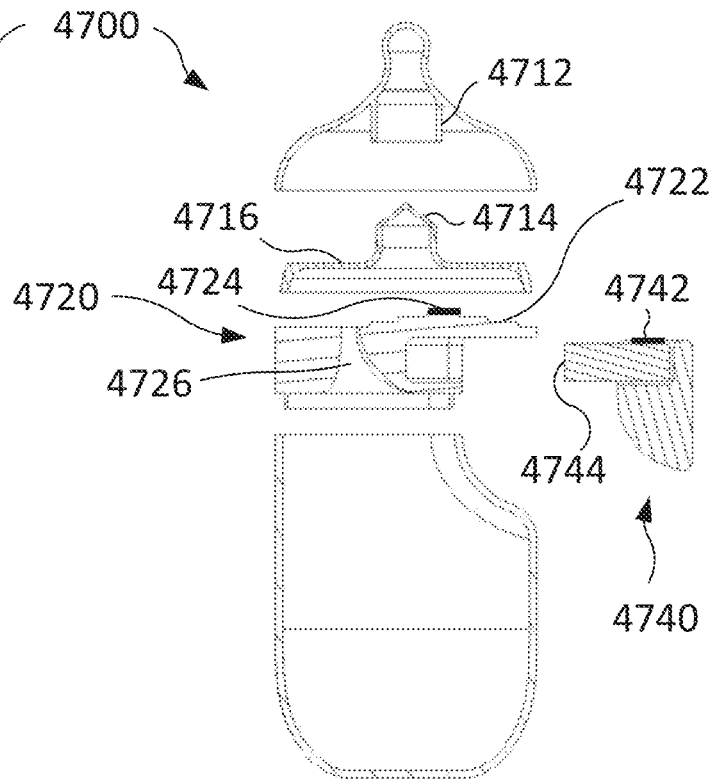
Figure 47C:
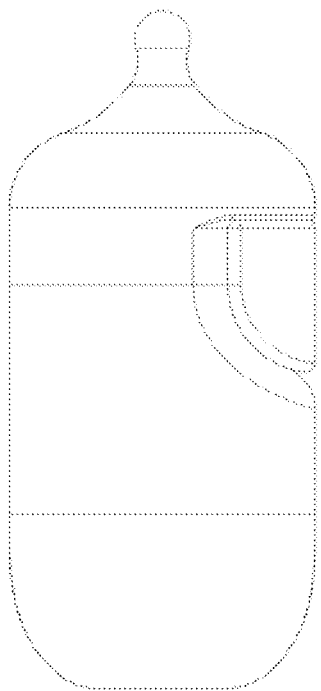
Figure 47D:
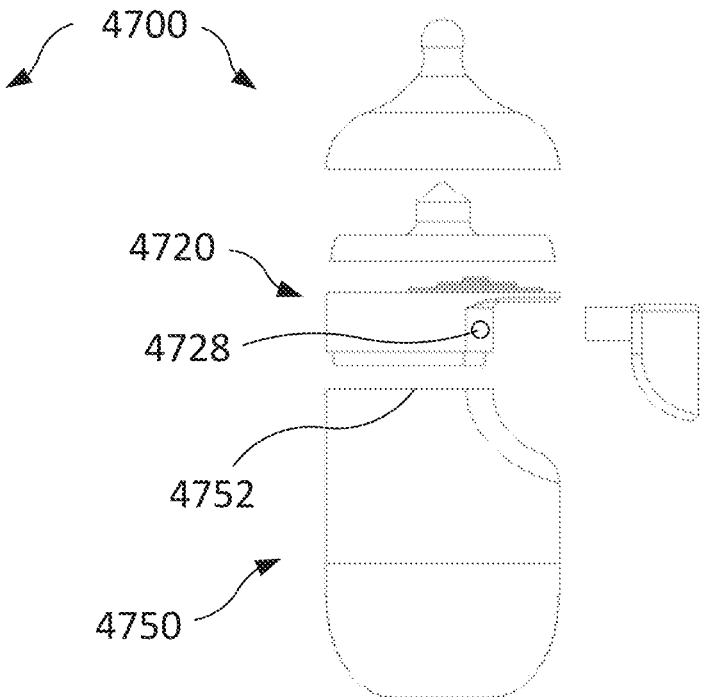

FIG. 46 depicts aspects of a live counting bottle system 4600 according to embodiments of the present invention. As shown here, a live counting bottle system 4600 can include a bottle nipple 4610, a one way valve assembly 4620, a fluid counter housing (top portion) 4630, a fed amount display 4640, a power on/off button 4650, a fluid container 4660, an electronic fluid counter 4670, and battery indicator lights 4680. In some cases, a live counting bottle system 4600 may not include a fed amount display. Relatedly, in some embodiments, a fed amount display can be displayed on a personal device (e.g. tablet or smartphone).

FIGS. 47A to 47D depict aspects of a live counting bottle system 4700 according to embodiments of the present invention. As shown here, a live counting bottle system 4700 can include a flexible bottle nipple 4710, an inner ring 4712 to limit a fluid path, the inner ring 4712 mating with a one way valve 4714 that is seated in a plate like housing 4716. System 4700 also includes a fluid counter housing 4720 having a flexible diaphragm 4722 with a magnet 4724 embedded therein, the diaphragm 4722 having an expanded configuration during negative pressure by sucking action. Housing 4720 also has a fluid pathway 4726 from the container, so fluid can enter the fluid counter housing. Further, housing 4720 includes a fluid exit point or conduit 4728 so that after being pushed by peristaltic rollers, fluid can be available on the top of the flexible diaphragm. System 4700 also includes an electronic fluid counter 4740 having a hall effect sensor 4742, peristaltic rollers 4744, and other operational mechanisms such as battery indicator lights, a fluid dispensed display, a power on/off button, a battery, a charging port, and a motor. System 4700 further includes a fluid container 4750 having threads 4752 that mate with a fluid counter housing.

Figure 48A:
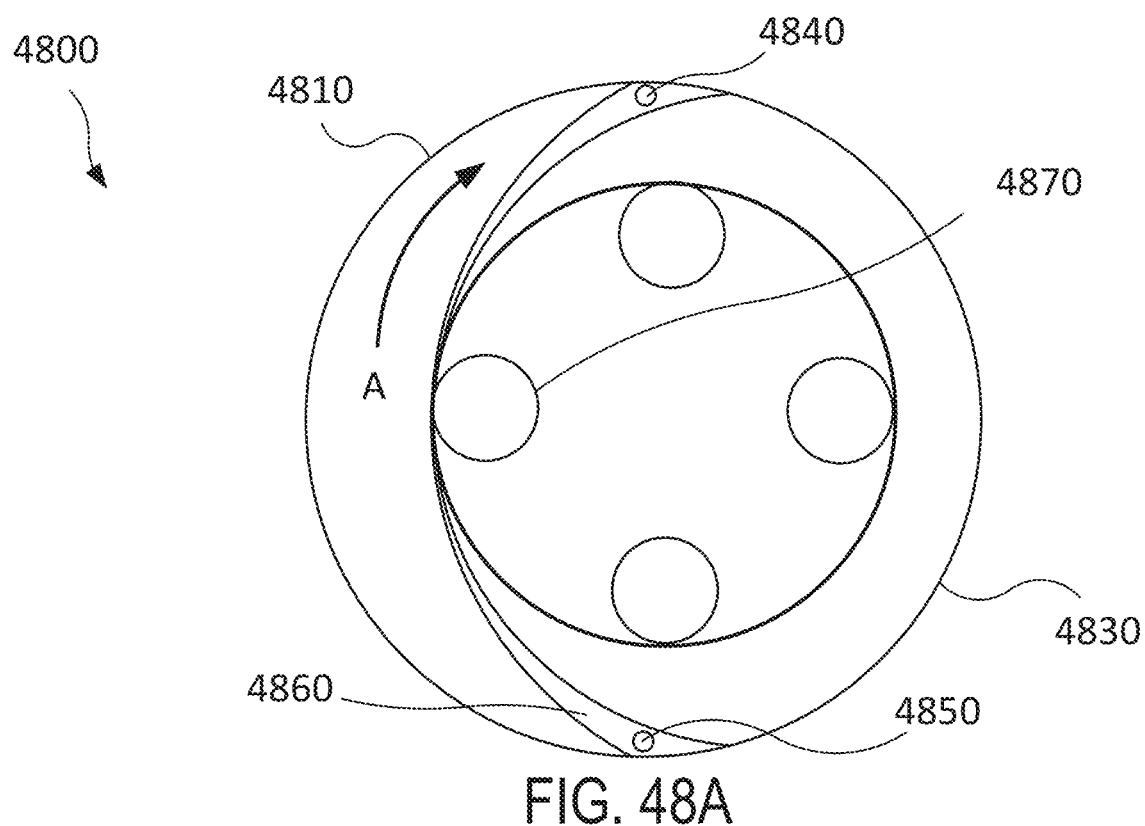
FIGS. 48A and 48B illustrate aspects of a breastmilk pumping and feeding device, in accordance with some embodiments.
Figure 48B:
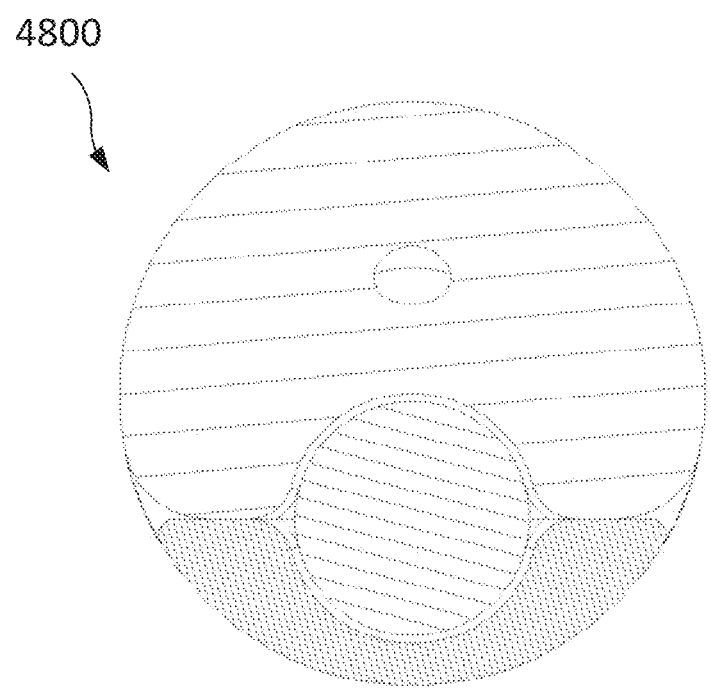

FIGS. 48A and 48B depict isolated aspects of a live counting bottle system 4800 according to embodiments of the present invention. As shown here, such isolated aspects of the system 4800 can include a fluid counter housing 4810 and an electronic fluid counter 4830. Further, system 4800 can include a fluid exit or conduit 4840 providing a pathway to a nipple, a fluid entrance or conduit 4850 providing a pathway from the fluid container, and peristaltic tubing or sheath 4860 that holds or defines a fluid pathway, whereby peristaltic rollers 4870 can propel fluid through the tubing 4860 (for example in the direction indicated by arrow A).

Figure 49:
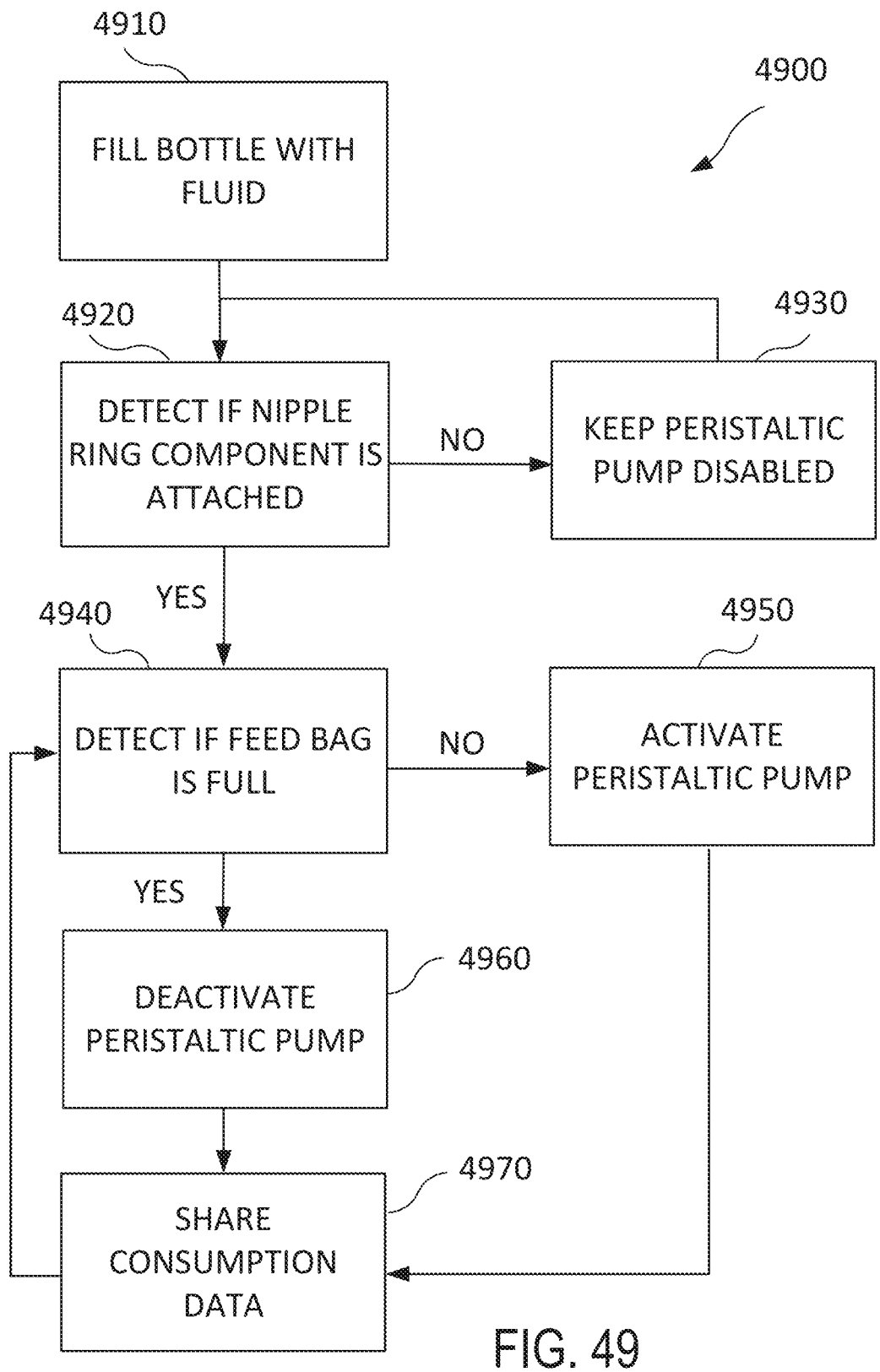
FIG. 49 illustrates aspects of a breastmilk feeding method, in accordance with some embodiments.
Figure 50A:
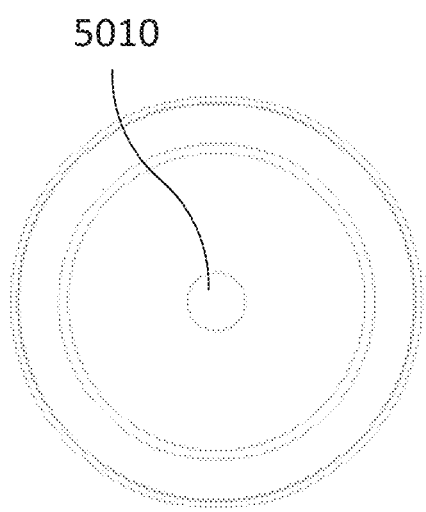
FIGS. 50A to 50D illustrate aspects of a breastmilk pumping and feeding device, in accordance with some embodiments.
Figure 50B:
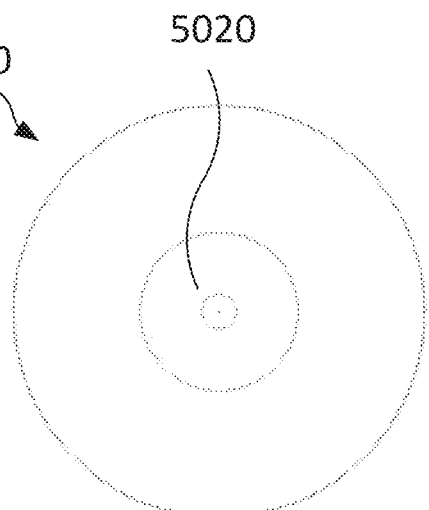
Figure 50C:
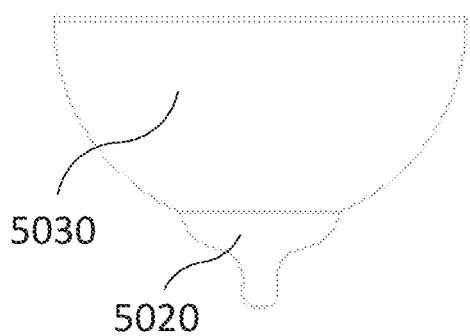
Figure 50D:
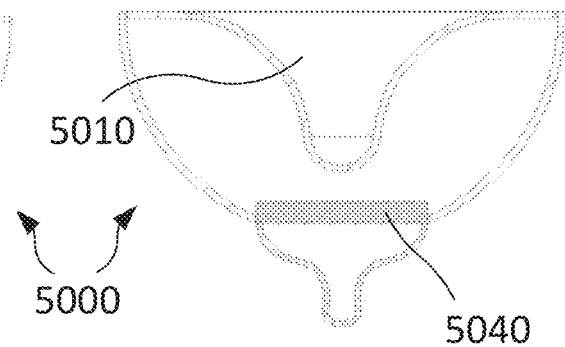
Figure 51A:
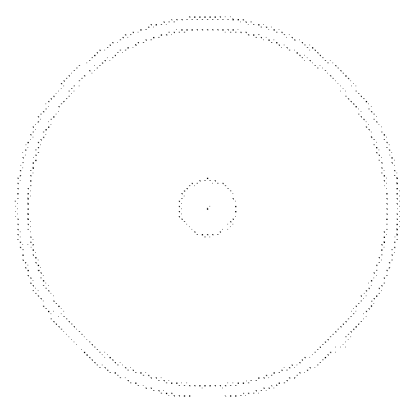
FIGS. 51A to 51D illustrate aspects of a breastmilk pumping and feeding device, in accordance with some embodiments.
Figure 51B:
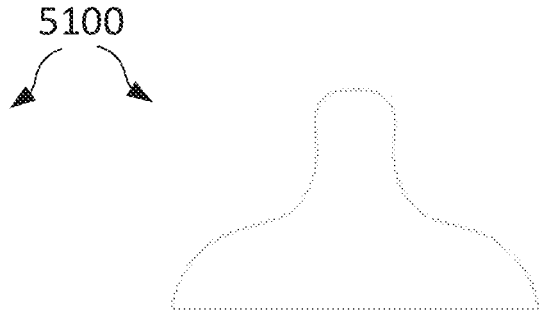
Figure 51C:
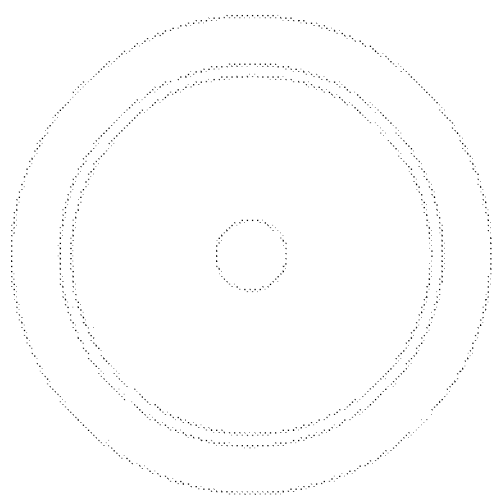
Figure 51D:
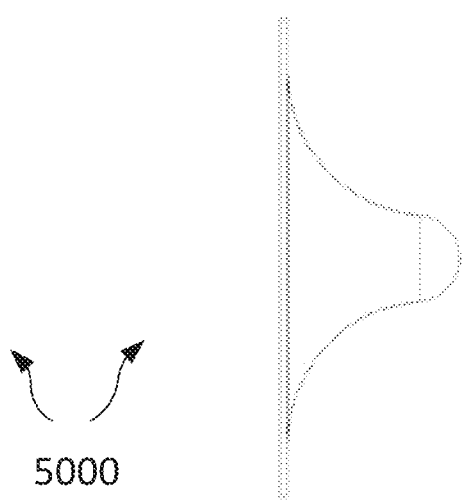

FIG. 49 depicts aspects of a method 4900 of operation for a feeding device such as a live counting bottle. Step 4910 can include filling a bottle with fluid. Step 4920 can include detecting if a nipple ring component is attached. If the nipple ring component is not attached, the method can include keeping the peristaltic pump disabled, as indicated in step 4930. If the nipple ring is attached, the method can include detecting if the feedbag is full, as indicated in step 4940. If the feedbag is full, the method can include activating the peristaltic pump, as indicated by step 4950, and sharing consumption data, as indicated by step 4970. If the feedbag is not full, the method can include deactivating the peristaltic pump, as indicated by step 4960, and sharing consumption data, as indicated by step 4970. After sharing consumption data, the method may include detecting if the feedbag is full, as indicated by step 4940.

FIGS. 50A to 50D depict isolated aspects of a feeding system 5000 having a counting sensor chip, according to embodiments of the present invention. As shown here, such isolated aspects of the system 5000 can include a flange 5010 as illustrated in the back view of FIG. 50A. A nipple 5020 can be attached to the front of a container 5030 to allow for a baby to drink, as illustrated in the front view of FIG. 50B. The container 5030 can hold expressed milk. The breast flange 5010 can create constriction for the mother's breast, and can be connected to an external pumping source. A milk counting sensor 5040 can be inserted between the container and the baby nipple, and can track flow of expressed milk into the baby's mouth.

FIGS. 51A to 51D depict isolated aspects of a feeding system 5100, according to embodiments of the present invention. A nipple side view is provided in FIG. 50B and a flange side view is provided in FIG. 50D.

Figure 52A:
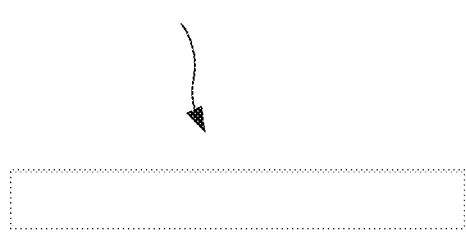
FIGS. 52A and 52B illustrate aspects of a breastmilk pumping and feeding device, in accordance with some embodiments.
Figure 52B:
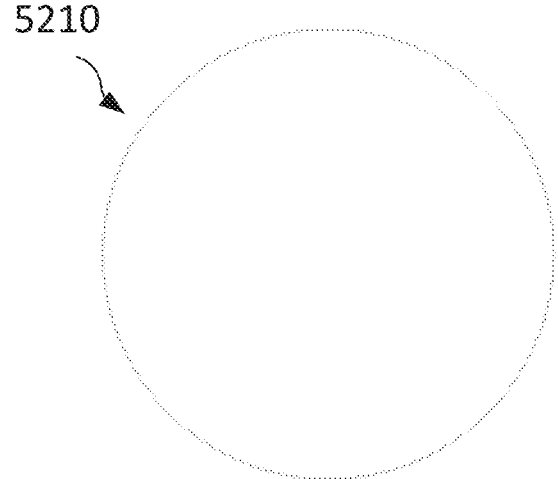
Figure 53A:
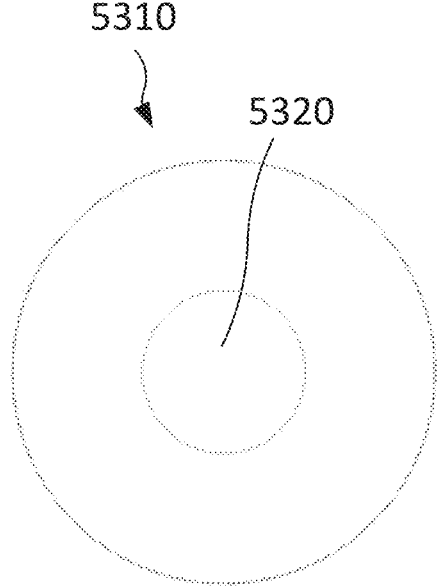
FIGS. 53A and 53B illustrate aspects of a breastmilk pumping and feeding device, in accordance with some embodiments.
Figure 53B:
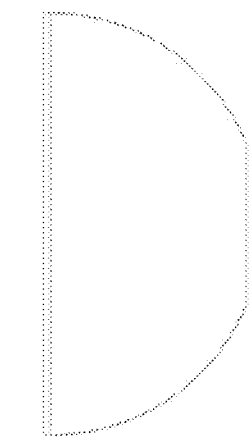
Figure 54A:
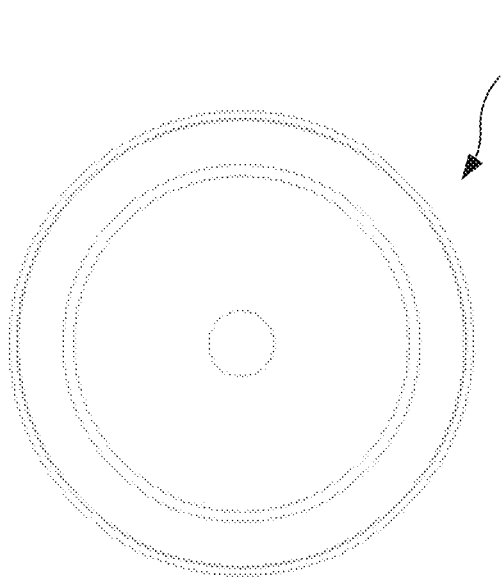
FIGS. 54A to 54D illustrate aspects of a breastmilk pumping and feeding device, in accordance with some embodiments.
Figure 54B:
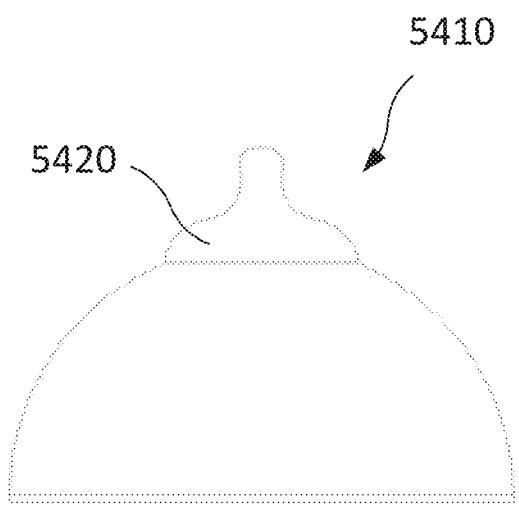
Figure 54C:
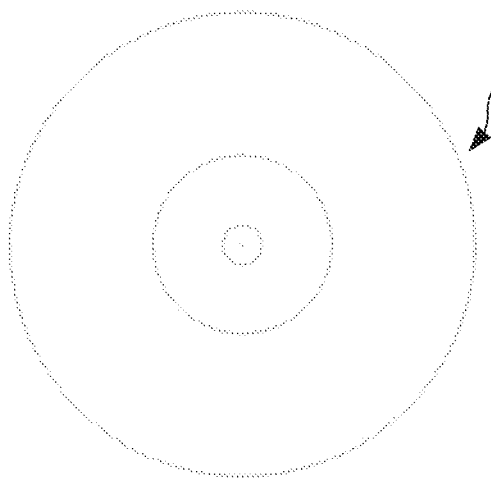
Figure 54D:
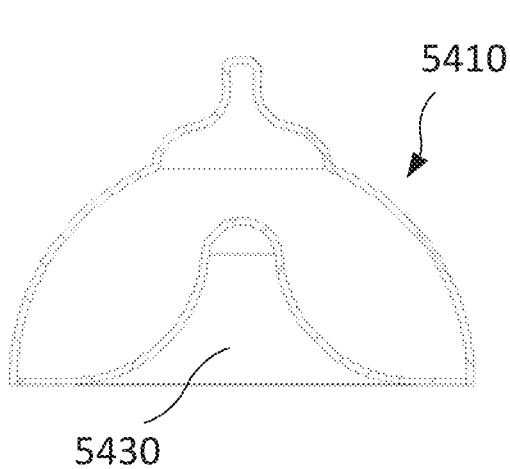

FIGS. 52A and 52B depict isolated aspects of an expressed milk flow sensor 5210 according to embodiments of the present invention. FIG. 52A provides a side view of sensor 5210 and FIG. 52B provides a front view of sensor 5210. FIGS. 53A and 53B depict isolated aspects of a container 5310 according to embodiments of the present invention. FIG. 53A illustrates an opening 5320 on the container where a baby nipple can be attached. FIG. 53B provides a side view of container 5310 with no sensor, flange, or baby nipple attached.

FIGS. 54A to 54D depict aspects of an integrated nipple assembly 5410 according to embodiments of the present invention. As shown in the pump assembly embodiment illustrated in FIG. 54B, the nipple 5420 can be integrated into the side of the container and there is no sensor that tracks the consumption of expressed milk. As shown in the pump assembly embodiment illustrated in FIG. 54D, the flange 5430 can attach into the milk container.

Figure 55A:
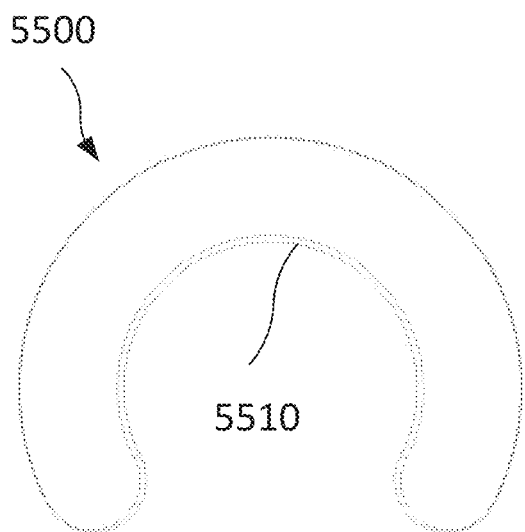
FIGS. 55A to 55D illustrate aspects of a breastmilk pumping and feeding device, in accordance with some embodiments.
Figure 55B:
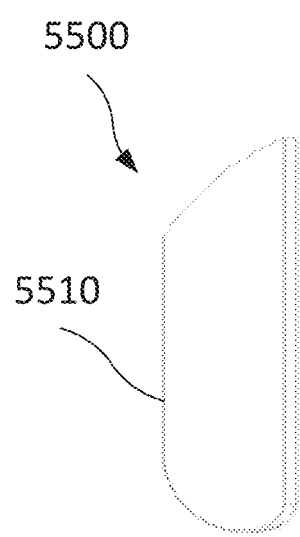
Figure 55C:
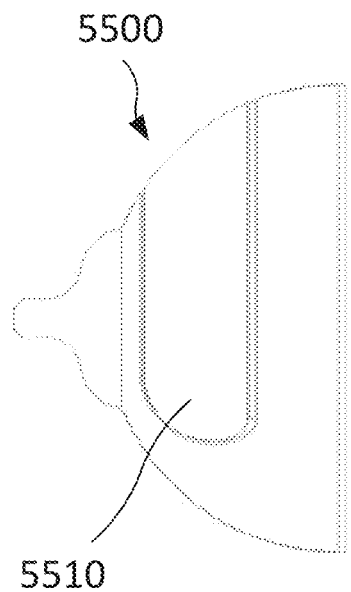
Figure 55D:
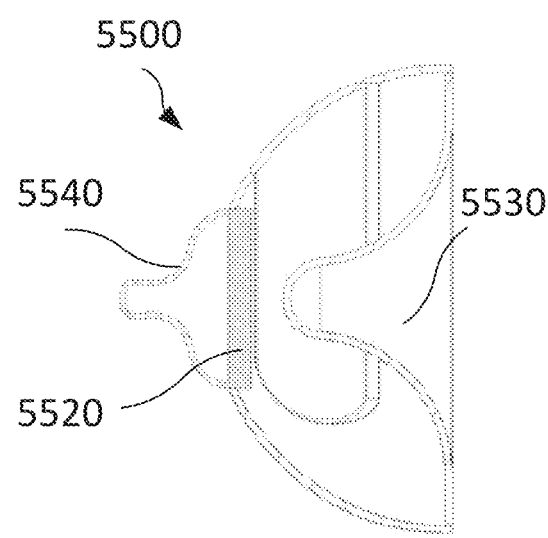

FIGS. 55A to 55D depict aspects of a manual expression pump assembly 5500 according to embodiments of the present invention. As shown here, an overmolded component 5510 of the assembly can be constructed of soft plastic, and can have a shape that follows the curvature of the container, making it appear to be in one continuous shape. As illustrated in FIG. 55C, the overmolded component 5510 can be overmolded or integrated into the container, and this can allow the mother to press the soft plastic part, creating a vacuum to manually express breast milk. As illustrated in FIG. 55D, this pump assembly can utilize a milk flow sensor 5520 as disclosed elsewhere herein, and can also include a nipple 5540 as disclosed elsewhere herein. The nipple 5540 and/or the sensor 5520 may be removable. A flange 5530 can attach to the milk container, and can have other flange features as disclosed elsewhere herein.

Figure 56A:
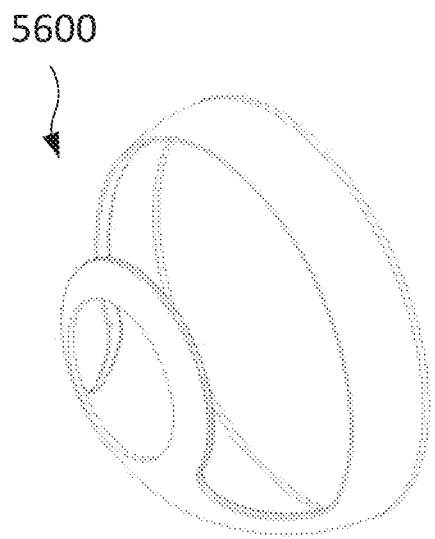
FIGS. 56A to 56D illustrate aspects of a breastmilk pumping and feeding device, in accordance with some embodiments.
Figure 56B:
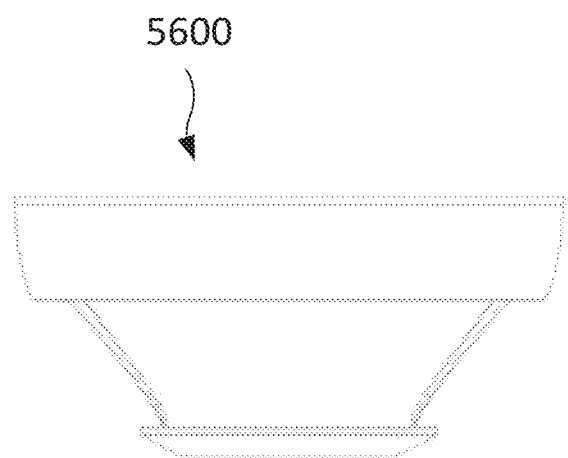
Figure 56C:
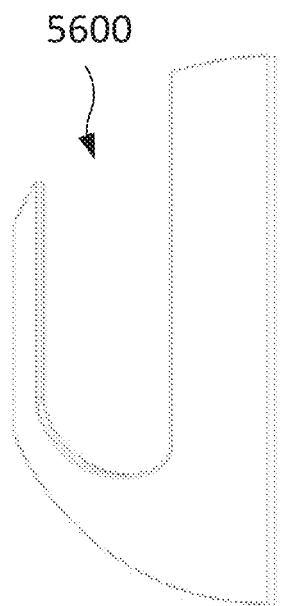
Figure 56D:
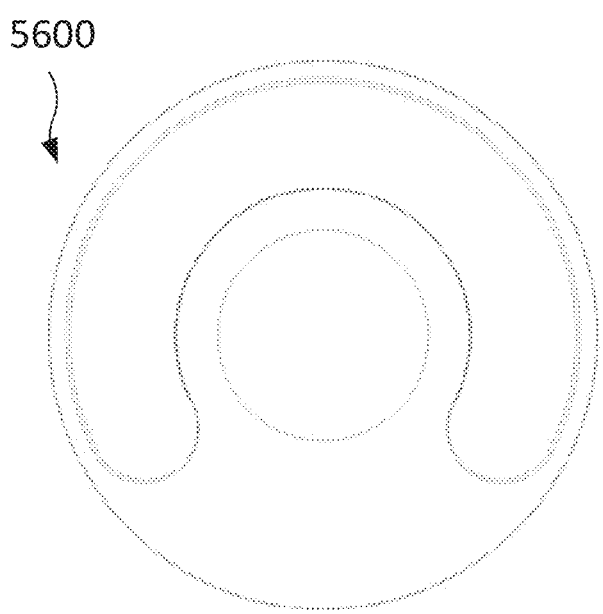

FIGS. 56A to 56D depict aspects of a container 5610 according to embodiments of the present invention. FIG. 56A provides a view of the container 5610 without an integrated softer plastic piece, or the flange and baby nipple components. As shown in FIG. 56C, the nipple and the milk counting sensor can both be removed.

Figure 57A:
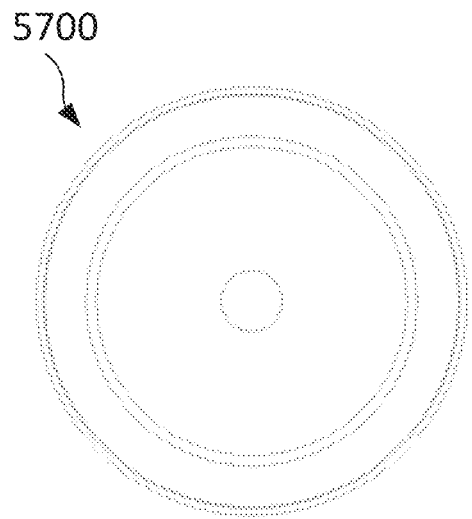
FIGS. 57A to 57D illustrate aspects of a breastmilk pumping and feeding device, in accordance with some embodiments.
Figure 57B:
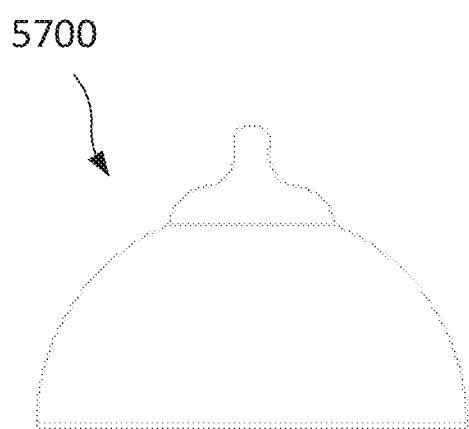
Figure 57C:
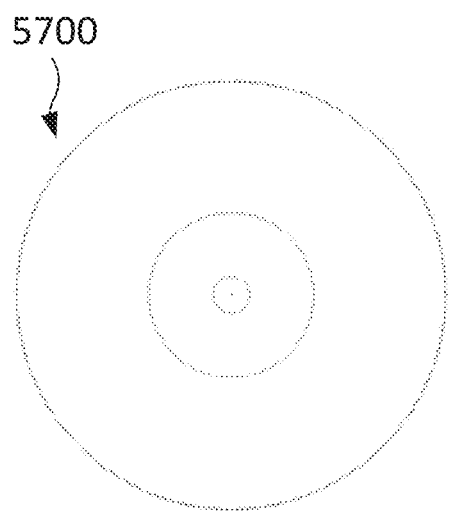
Figure 57D:
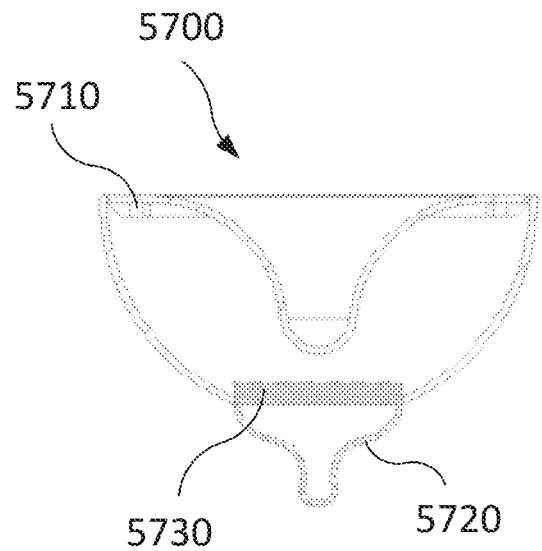

FIGS. 57A to 57D depict aspects of an infrared (IR) sensor pump assembly 5700 according to embodiments of the present invention. As shown in FIG. 57D, an IR sensor 5710 can take the shape of a ring around the interior of a flange component, and can track the amount of milk stored in the container (separate from a sensor 5720 that tracks how much the baby has consumed). Sensor 5720 is a milk flow sensor. In some embodiments, the baby nipple 5730 can have nipple features as disclosed elsewhere herein. The nipple 5730 and the sensor 5720 can be removed, in some embodiments.

Figure 58A:
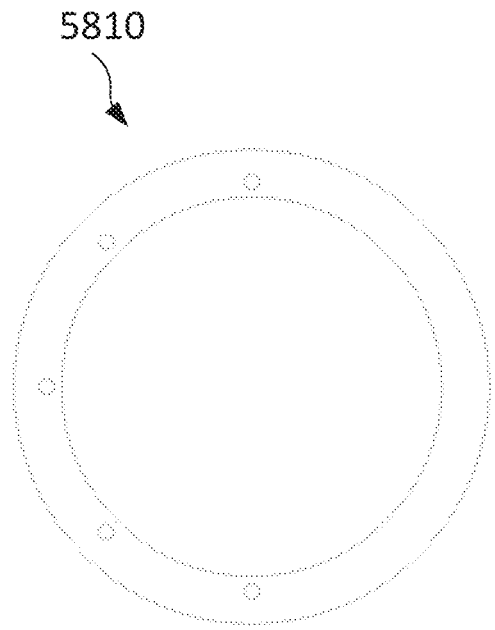
FIGS. 58A to 58C illustrate aspects of a breastmilk pumping and feeding device, in accordance with some embodiments.
Figure 58B:
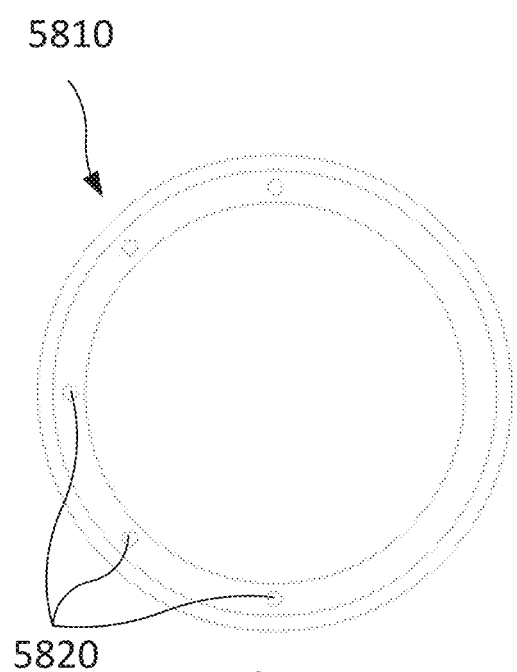
Figure 58C:
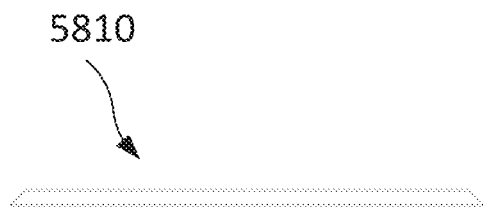

FIGS. 58A to 58C depict aspects of an infrared (IR) sensor 5810 according to embodiments of the present invention. As shown in the back view of FIG. 58A the sensor can have a ring shape to allow for an easy fit on the interior of a breast flange. As shown in the front view of FIG. 58B, the sensor can have one or more infrared light sources 5820. As the milk in the container fills up, it covers each of the infrared light sources one by one, which communicate vial Bluetooth with a phone to signal to the mother how much milk has been stored in the container.

Figure 59A:
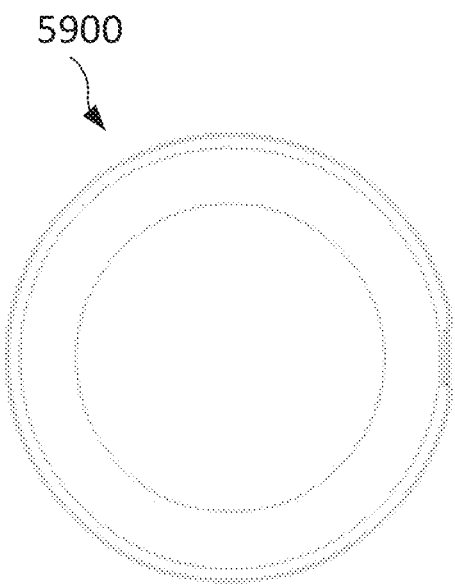
FIGS. 59A to 59D illustrate aspects of a breastmilk pumping and feeding device, in accordance with some embodiments.
Figure 59B:
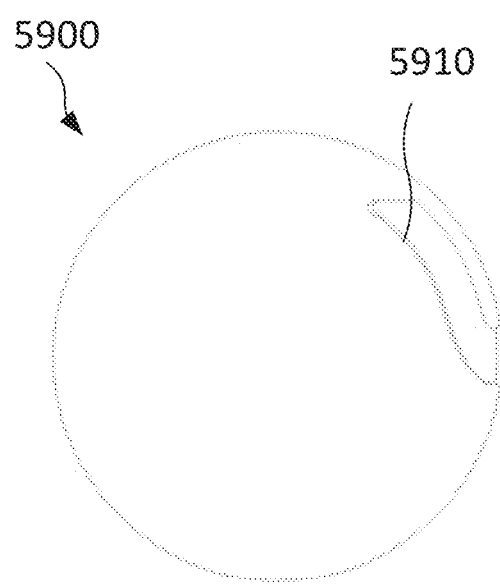
Figure 59C:
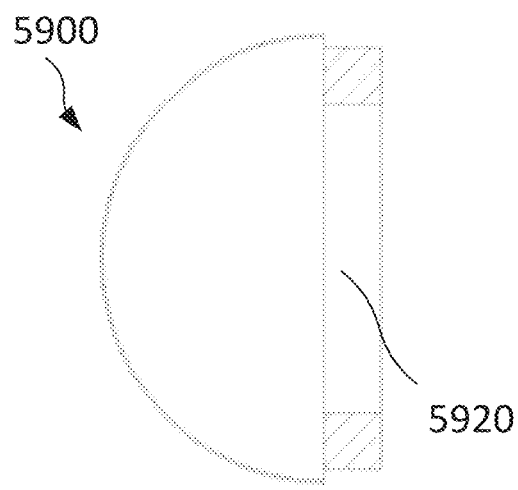
Figure 59D:
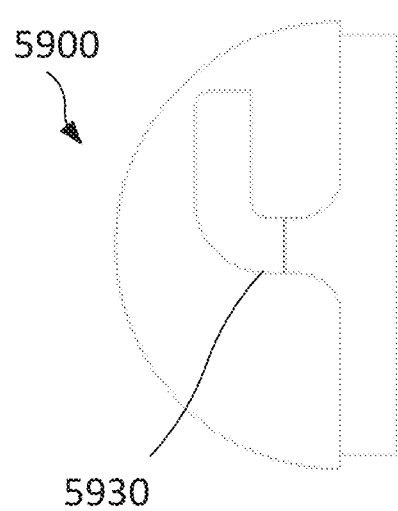

FIGS. 59A to 59D depict aspects of a capacitance sensor pump assembly 5900 according to embodiments of the present invention. As shown in the back view of a container depicted in FIG. 59A, an assembly can include a container and capacitance sensor, and a breast flange is not shown here. As shown in FIG. 59B, a capacitance sensor 5910 can be provided as a thin component that appears to wrap around the side of the container. A capacitance sensor 5910 can be in the form of a sticker, and can be used on the container to sense how much breast milk has been stored in the container. As shown in FIG. 59C, a component 5920 that fits onto the back of the container has an opening to allow for a flange to be inserted through it. As shown in FIG. 59D, a capacitance sensor can be powered by a component 5930 that fits on the back of the container, which provides power to the sensor and interprets data to send to a phone via Bluetooth.

Figure 60A:
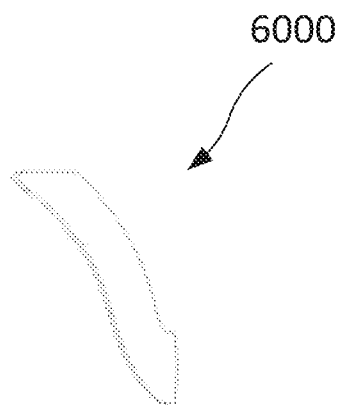
FIGS. 60A to 60D illustrate aspects of a breastmilk pumping and feeding device, in accordance with some embodiments.
Figure 60B:
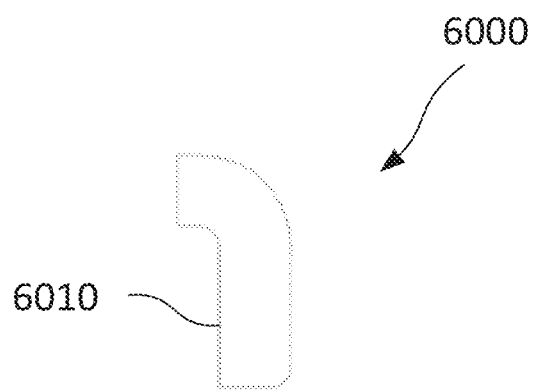
Figure 60C:
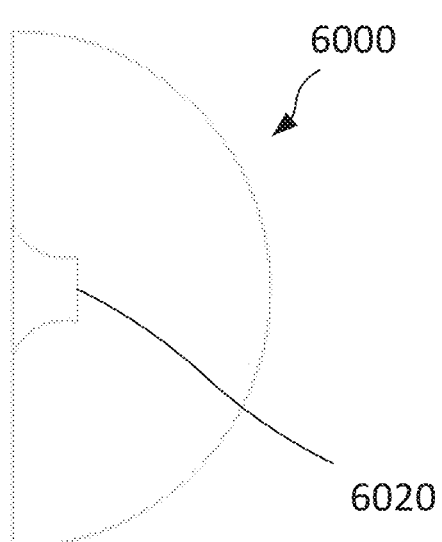
Figure 60D:
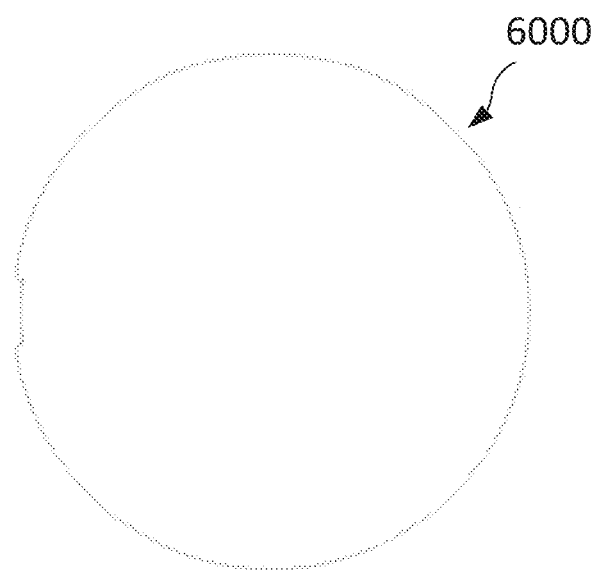

FIGS. 60A to 60D depict additional aspects of a capacitance sensor pump assembly 6000 according to embodiments of the present invention. Typically, the capacitance sensor is attached with the container. FIG. 60B depicts a detached capacitance sensor 6010. FIG. 60C illustrates the container without the capacitance sensor. A cutout 6020 on the side of the container can be a connection point for the back component that provides power to the capacitance sensor that is on the container.

Figure 61A:
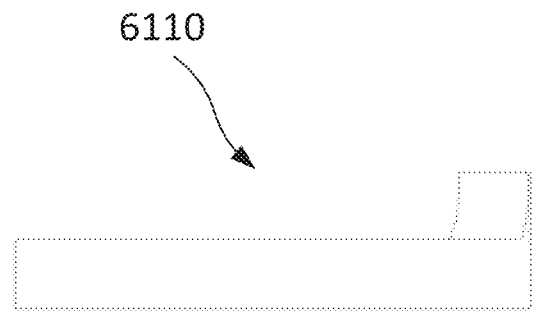
FIGS. 61A to 61C illustrate aspects of a breastmilk pumping and feeding device, in accordance with some embodiments.
Figure 61B:
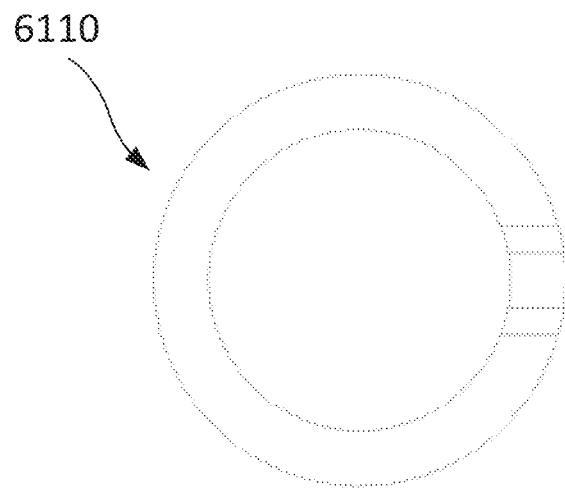
Figure 61C:
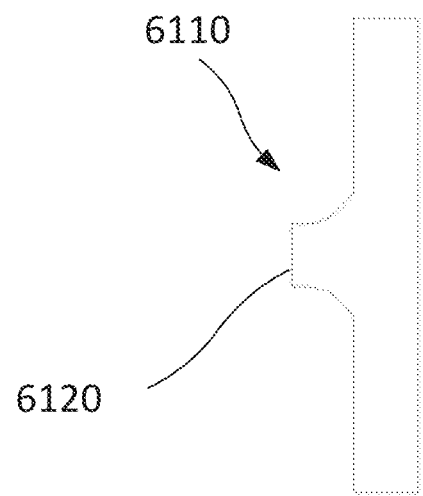

FIGS. 61A to 61C depict aspects of a back ring component 6110 that plugs into a container, providing power to a capacitance sensor. The component 6110 can include a protrusion 6120, at a point at which the back ring component interacts with the container, which can be the site of a plug mechanism or electrical connection.

Figure 62A:
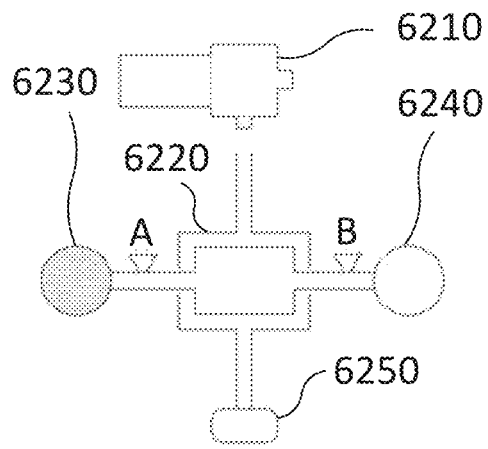
FIGS. 62A to 62E illustrate aspects of a breastmilk pumping and feeding device, in accordance with some embodiments.

FIGS. 62A to 62E depict aspects of a pumping feature, according to embodiments of the present invention. As depicted in FIG. 62A, the pumping feature includes an air pump 6210 that pumps air into a chamber 6220. The chamber holds a bag 6222 as depicted in FIG. 62A. With returning reference to FIG. 62A, milk begins at inlet 6230 and is drawn into the bag by negative pressure created by the pump. The bag is connected to the milk inlet, and is also connected to a milk outlet 6240. A solenoid valve 6250 serves to release air from the chamber, and the default position is CLOSED. Cutoff points A and B hold vacuum in the line from the inlet to the outlet.

Figure 62B:
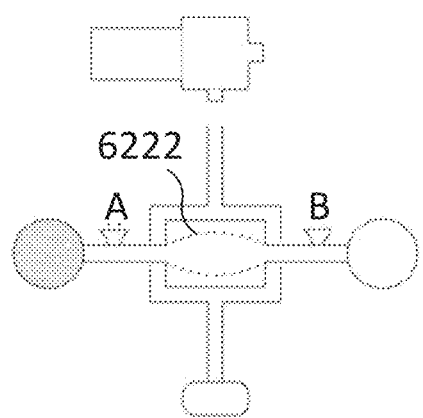

As shown in FIG. 62B, the air pump can push air into the chamber, thereby compressing the bag 6222 in the chamber, as indicated by the dashed lines.

Figure 62C:
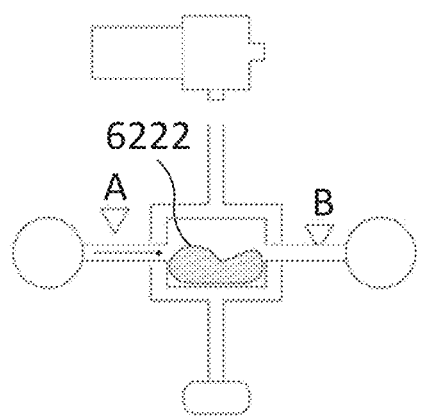

As shown in FIG. 62C, the cutoff point A releases, allowing milk to flow from the inlet into the bag. The bag can expand to the resting state with the release of the solenoid valve (which releases pressure), drawing milk through the inlet and into the bag.

Figure 62D:
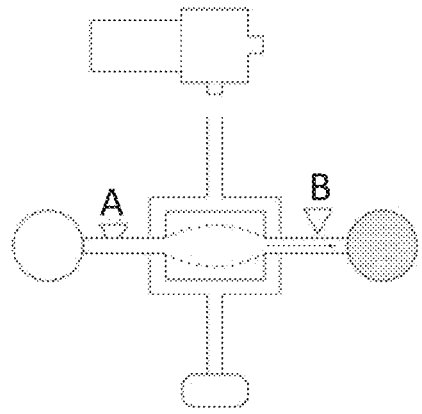

As shown in FIG. 62D, the air pump can pump air into the chamber, compressing the bag. Cutoff point A can close as air is pumped into the chamber. Cutoff point B can open as air is pumped into the chamber, allowing the milk from the bag to be pumped through the outlet. Milk can fill up the outlet chamber.

Figure 62E:
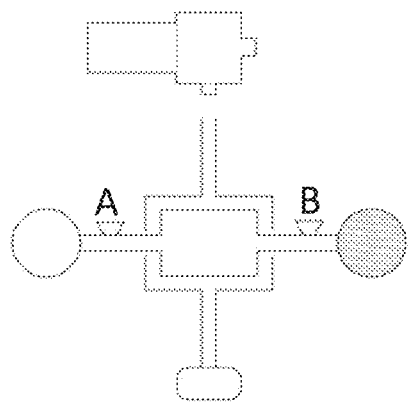

As shown in FIG. 62E, the air pump can be turned off, and cutoff points A and B can close the line to keep the milk stored in the outlet chamber.

In some cases, embodiments may involve systems and methods for counting without the need for venting. In some instances, such embodiments may involve the use of two venting bags and a switch. In some instances, such embodiments may involve the use of a peristaltic mechanism and one bag. In some instances, such embodiments may involve a counting bottle.

In some counting bottle embodiments, the on-demand suckling of a baby (or adult) mouth triggers the collapse of a chamber which contains a magnet on the distal end, such that when it collapses, the magnet demonstrates distance from a hall effect sensor. The indication of collapse triggers a bolus of milk to be sent into the chamber by peristaltic action, until the chamber is at its full size. The number of rotations of the peristaltic pump is counted by another hall effect sensor, which determines the amount of fluid that was made available to the infant. In some embodiments, the number of rotations of the peristaltic pump can be counted by a magnetic encoder. Embodiments of the present invention encompass the use of any of a variety of counting mechanisms for counting the number of rotations (or partial rotations) of the peristaltic pump. For a counting bottle, the source of the milk can be a bottle that can be held in hand, the fluid can be any fluid, and the amount of fluid actively consumed can either be displayed on the bottle directly, or on a connected device. This could be used to feed infants of any age, or attached to a larger bottle with a straw lead to accurately monitor drinking for adults as well. It could be of specific benefit to infants who are born prematurely, as the amount of intake is monitored by the mL. It could also be used to dose quantities of fluids or medications that are taken by mouth for any person.

Figure 63A:
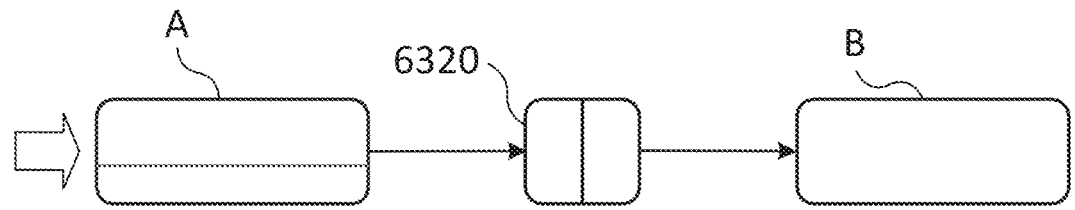
FIGS. 63A to 63D illustrate aspects of a breastmilk pumping and feeding device, in accordance with some embodiments.
Figure 63B:
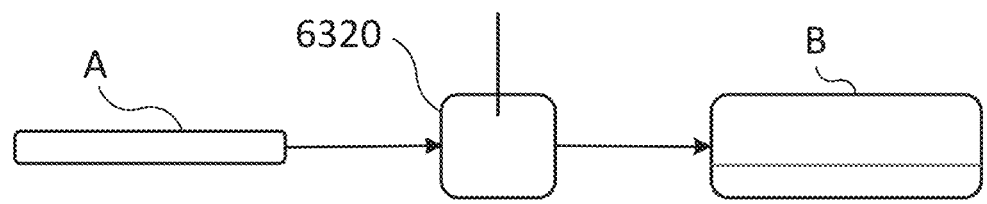
Figure 63C:
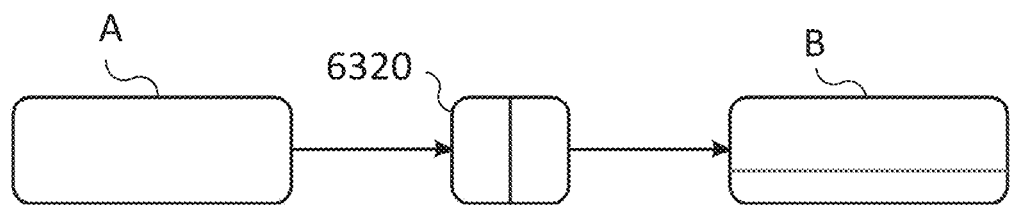
Figure 63D:
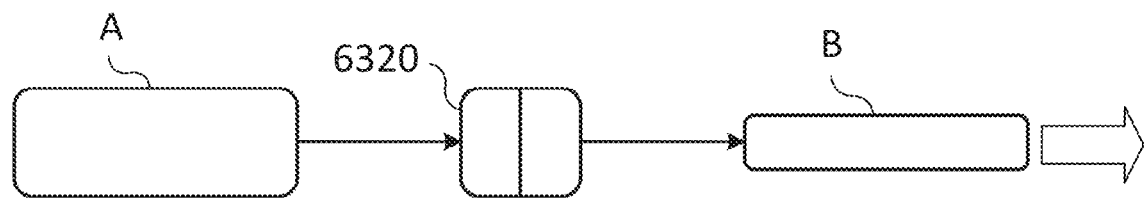

Some systems and method embodiments may involve alternating compression approaches. Exemplary breast pumps disclosed herein can provide alternating compression in between suction. This is based on the concept that a baby acts on the breast in two ways during effective breastfeeding, (a) by creating a local vacuum under the nipple by contorting the tongue into a bowl shape and (b) by releasing the bowl and causing the tongue to compress the areola between the tongue and the hard pallet (roof of mouth). The alternating method of these two actions both draws and squeezes milk out of the breast. Conventional negative pressure breast pumps act like the first action, while "hand expression" of milk work like the second action. Embodiments of the present invention encompass methods that involve mechanically incorporating the compression into a negative pressure device, including providing air filled pressure to the areola, and contortion of the flange, and the like. Hence, embodiments encompass the implementation of alternating compression to the areola/breast within a pumping device as disclosed herein. Such techniques can provide more effective expression and require less pumping time. In some cases, a feeding system can include a first compressible chamber and a second compressible chamber, and the first and second compressible chambers can alternate with filling and dispensing of feeding fluid throughout a feeding process or event. In some cases, two compressible chambers can alternate filling and dispensing. Relatedly, a feeding system can provide a fluid path extending from the nipple shield to the throughput aperture, the fluid path having two sections adjacent the throughput aperture, both having defined volumes, that alternate filling with fluid and dispensing fluid to the throughput aperture. FIGS. 63A to 63D illustrate aspects of a counting method embodiment, where two compressible chambers alternate to provide milk. As shown in FIG. 63A, in a first step, the switch 6320 can be closed, and compressible bag A can be filled with feeding fluid. As shown in FIG. 63B, in a second step, the switch 6320 is open, compressible bag A is compressed or collapsed, and feeding fluid flows into compressible bag B. As shown in FIG. 63C, in a third step, the switch 6320 is closed, compressible bag A returns to a neutral position or configuration, and the infant can drink or received feeding fluid from compressible bag B. As shown in FIG. 63D, in a fourth step, the switch 6320 is closed, and compressible bag B is compressed or collapsed as the infant drinks or receives feeding fluid from it. Both compressible bag A and compressible bag B can have magnets that are embedded in them, which allows their positions or configurations to be measured or detected, using sensors such as hall effect sensors.

Some systems and method embodiments may involve configurations that include a double counter connected to a dislocated negative pressure source. Exemplary embodiments may include two counter/feeder/collectors (one on each breast), connected centrally to a detached vacuum source that could be positioned anywhere (for example in between the breasts, on the upper half of each breast, on the shoulder or back of neck, or away from the body, and the like). Each counter/feeder/collector could have its own detached negative pressure source as well.

Some systems and method embodiments may involve configurations that include a massage feature. Exemplary embodiments can encompass a device or components thereof that are wearable in each bra, sitting on the upper half of the breast, or elsewhere. Some embodiments can have a massage feature which intends to provide massage to the breast for better expression of milk. This may or may not be through the external sensation caused by the motors involved in the device or may be a separate massage/vibration that can be independently controlled.

Some systems and method embodiments may involve configurations that include an inversed milk bag for the baby nipple. Exemplary embodiments may involve a milk bag with a magnet that collapses when the infant drinks and that works in an inversed fashion, so that the bag is flat at rest like the diaphragm component, and then expands into the cavity of the nipple as the baby suctions.

Some systems and methods embodiments may involve configurations that include a pace/breast mode. Exemplary embodiments provide for the ability to choose a setting on the pump or computer application in which the pace of the milk delivered to the baby nipple milk bag is capped such that it replicated the pace in which a baby could extract milk from a breast. The intention can be to prevent the infant from receiving milk at a faster pace than they would at normal breastfeeding, and become used to this pace, resulting in either rejecting the breast in the future, choking from receiving too much milk too quickly, or overfeeding.

Some systems and methods embodiments may involve configurations that include a pacify mode. Exemplary embodiments enable the feeding function to be purposefully shut off by the mother, disabling the peristaltic motor and thereby creating a pacifier out of the nipple attachment. As examples, this feature can be used to promote sleep, to limit consumption, or to allow the infant to engage in non-nutritive sucking, which can aid their digestion by triggering peristalsis of the GI tract.

System and method embodiments disclosed herein can be used to add other fluids typically administered to a baby through a bottle, dropper, or syringe, such as formula, vitamins, medicines, and water. This may be done on its own or in combination with breastmilk.

Some systems and methods embodiments may involve configurations that include an infant nipple apparatus. Exemplary embodiments can include a magnet and hall effect displaying distance from the no rest position of the compressible compartment, and can be used separate or with the device to determine relative suction power of the infant's mouth.

Embodiments of the present invention may incorporate the operation of a backflow valve, such as a one-way valve within the infant nipple apparatus that prevents air from entering the compressible feeding chamber and falsely indicating that, because the bag is not compressed, additional milk is not needed. With regard to feeding and/or tracking embodiments, a device can include a companion phone application that connects via Bluetooth to the device. The estimated amount of milk consumed by the infant can be tracked on the device and displayed on the phone application, which can also store feeding data from each individual pumping session. This allows the mother to keep track of how much milk the baby has drank over a span of time. This also allows a new set of automated data to be collected on when and how much a mother is feeding a child, how many mothers are using an aid for feeding, at what ages, and which infant/mother dyads could use other forms of breastfeeding assistance. Associating this with user provided demographics such as maternal age, geographic location, and the like, and provides market knowledge to service mothers. In some embodiments, the device can pump milk from the mother's breast, while at the same time, allowing the mother to feed her infant the freshly expressed breast milk, in a breastfeeding position. The feeding occurs via a nipple attached to the breast pump and occurs automatically in response to the baby sucking at the nipple. In some cases, the mother can also switch off the feeding function manually if chosen. In some embodiments, the device can use a feeding mechanism that is driven by the infant. Relatedly, in some embodiments, the device only makes milk available for the baby to drink when the infant is sucking at the nipple attachment, much like a breast. In some cases, integrated sensors can operate to only make milk available to the infant if expressed breast milk is present, and will not push air if milk is not available. In that manner, the device can operate as a "low-colic" system that provides little air to the infant. Embodiments disclosed herein can incorporate various feeding mechanism features. For example, with regard to peristaltic pumping, the expressed breast milk can be transferred from the milk container to the nipple attachment via a peristaltic pumping mechanism acting on a tube. This mechanism allows the milk to be transferred hygienically from the milk container to the nipple attachment, only when the baby requests it. With regard to dosing tube and priming chamber features, the expressed breast milk can be transferred from the milk container to the nipple attachment via a series of priming chambers and dosing tubes. The priming chambers can hold expressed breast milk, and can transfer that milk to the nipple attachment via a dosing tube controlled by a series of valves and sensors. With regard to compressible bag features, expressed milk can be transferred from the milk container to the nipple attachment via a compressible bag that pulls expressed milk from the milk chamber to the nipple attachment via suction that is actuated by a vacuum pump. Such a compressible bag can have a series of cutoff points that allow the suction mechanism to pull milk from the container into the bag, then push the milk from the bag into the nipple attachment. With regard to storage, the device can operate to store milk in the container that remains uncontaminated from the baby's saliva, and thus maintains longer CDC recommended shelf life. This can be accomplished by operation of a one way valve in an infant nipple. For example, a one way valve within the nipple can prevent the infant from transferring contaminated milk (milk that has been in the infant's mouth) back into the nipple attachment. With regard to peristaltic action, a one directional flow of the peristaltic motor action can further inhibit the flow of milk back into the tank. With regard to liquid sensing, the device can include a sensor or series of sensors that track the amount of expressed breast milk accumulated in the milk container. This sensor can provide readings by indicating the presence or absence of milk at different heights along the milk container, corresponding to ounces of milk present as the milk container fills up. With regard to pumping, the device can use a pumping mechanism to create vacuum at the breast, causing breast milk to be expressed and stored in a milk container. The user can control the pumping strength and speed using physical buttons on the device or by their mobile device. With regard to wearable embodiments, the entire device can be wearable, and can be used by placing in a pumping bra that sits directly over the breast. The nipple attachment can be positioned on the device such that it can protrude from the opening in the pumping bra.

According to some embodiments, the infant's on-demand sucking at the bottle like nipple, automatically drives the flow of further milk made available to the infant.

Although the preceding description contains significant detail in relation to certain preferred embodiments, it should not be construed as limiting the scope of the invention but rather as providing illustrations of the preferred embodiments.

Embodiments of the present invention encompass kits having breastmilk pumping and feeding devices as disclosed herein. In some embodiments, the kit includes one or more breastmilk pumping and feeding devices, along with instructions for using the device(s) for example according to any of the methods disclosed herein.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims. In addition, each reference provided herein in incorporated by reference in its entirety to the same extent as if each reference was individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

What is claimed is:

1. A system for indicating an amount of a feeding fluid that is dispensed to an individual, comprising:
   a chamber that stores feeding fluid;
   a dosing mechanism that receives feeding fluid from the chamber, and dispenses discrete packets of feeding fluid, each discrete packet having a discrete packet volume;
   a collapsible chamber that receives the discrete packets of feeding fluid dispensed by the dosing mechanism;
   a feeding apparatus having a nipple interior that receives feeding fluid from the collapsible chamber and that allows feeding fluid to flow from the nipple interior to the individual's mouth through an outlet of the feeding apparatus;
   a one-way valve disposed between the collapsible chamber and the nipple interior, wherein the one-way valve allows fluid flow from the collapsible chamber to the nipple interior and prevents fluid flow from the nipple interior to the collapsible chamber;
   a sensor assembly that determines when the collapsible chamber is available to receive a new discrete packet of feeding fluid dispensed from the dosing mechanism; and
   a counting mechanism that registers a count for each dispensing event performed by the dosing mechanism.

2. The system according to claim 1, further comprising a processor that determines the amount of feeding fluid that is dispensed to the individual based on the discrete packet volume and the number of registered counts.

3. The system according to claim 1, wherein the dosing mechanism comprises a peristaltic pump, wherein the sensor assembly comprises a hall effect sensor, and wherein the system further comprises:
   a magnet in operative association with the collapsible chamber,
   wherein the sensor assembly determines that the peristaltic pump should dispense the new discrete packet of feeding fluid when the magnet reaches a first distance away from the hall effect sensor and that the peristaltic pump should pause when the magnet reaches a second distance away from the hall effect sensor, the first distance being greater than the second distance.

4. The system according to claim 1, wherein the dosing mechanism comprises a gate and a tube, wherein the sensor assembly comprises a full sensor and an empty sensor, wherein the gate allows passage of feeding fluid through the tube when the empty sensor indicates the tube is empty of feeding fluid, and wherein the gate prevents passage of feeding fluid through the tube when the full sensor indicates the tube is full of feeding fluid.

5. The system according to claim 1, wherein the dosing mechanism comprises a first compressible chamber and a second compressible chamber, and wherein the first and second compressible chambers alternate with filling and dispensing of feeding fluid.

6. The system according to claim 1, further comprising a sensor selected from the group consisting of a capacitance sensor and an infrared sensor, wherein the sensor is configured to detect a feeding fluid amount present in the chamber, and wherein the system is configured to signal additional feeding fluid to enter the chamber based on the detected feeding fluid amount.

7. The system according to claim 1, further comprising a breast flange in fluid communication with the chamber, wherein the breast flange defines a breast flange axis, the feeding apparatus defines a feeding apparatus axis, and the breast flange axis is either in-line with or superior to the feeding apparatus axis.

8. The system according to claim 1, further comprising a breast flange in fluid communication with the chamber, wherein the dosing mechanism comprises a peristaltic wheel, and a center of the peristaltic wheel is positioned posterior to an anterior portion of the breast flange and anterior to a posterior portion of the breast flange.

9. The system according to claim 1, further comprising a breast flange in fluid communication with the chamber, wherein the chamber is positioned within a housing, and the feeding apparatus is attached with the housing and positioned inferior to the breast flange.

10. The system according to claim 9, wherein the feeding apparatus is removable from the housing.

11. The system according to claim 1, wherein the dosing mechanism comprises a peristaltic pump having a peristaltic tubing, and at least a portion of the tubing is positioned inferior to the nipple interior of the feeding apparatus.

12. A method for indicating an amount of a feeding fluid that is dispensed to an individual, the method comprising:
storing feeding fluid in a chamber;
receiving feeding fluid from the chamber at a dosing mechanism;
dispensing discrete packets of feeding fluid, each discrete packet having a discrete packet volume, from the dosing mechanism;
receiving, at a collapsible chamber, the discrete packets of feeding fluid dispensed by the dosing mechanism;
allowing the discrete packets of feeding fluid to flow from the collapsible chamber, through a one-way valve, and into a nipple interior of a feeding apparatus, wherein the one-way valve allows fluid flow from the collapsible chamber to the nipple interior and prevents fluid flow from the nipple interior to the collapsible chamber;
determining, with a sensor assembly, when the collapsible chamber is available to receive a new discrete packet of feeding fluid dispensed from the dosing mechanism; and
registering, with a counting mechanism, a count for each dispensing event performed by the dosing mechanism.

13. The method according to claim 12, further comprising determining, with a processor, the amount of feeding fluid that is dispensed to the individual based on the discrete packet volume and the number of registered counts.

14. The method according to claim 12, wherein the dosing mechanism comprises a peristaltic pump, wherein the sensor assembly comprises a hall effect sensor,
wherein the collapsible chamber is coupled with a magnet, wherein the sensor assembly determines that the peristaltic pump should dispense the new discrete packet of feeding fluid when the magnet reaches a first distance away from the hall effect sensor and that the peristaltic pump should pause when the magnet reaches a second distance away from the hall effect sensor, the first distance being greater than the second distance.

15. The method according to claim 12, wherein the dosing mechanism comprises a gate and a tube, wherein the sensor assembly comprises a full sensor and an empty sensor, and wherein the method further comprises:
allowing, with the gate, passage of feeding fluid through the tube when the empty sensor indicates the tube is empty of feeding fluid; and
preventing, with the gate, passage of feeding fluid through the tube when the full sensor indicates the tube is full of feeding fluid.

16. The method according to claim 12, wherein the dosing mechanism comprises a first compressible chamber and a second compressible chamber, and wherein the method further comprises alternating filling and dispensing of feeding fluid by the first and second compressible chambers.

17. The method according to claim 12, further comprising:
detecting, with a capacitance sensor, a feeding fluid amount present in the chamber; and
signaling the entrance of additional feeding fluid into the chamber based on the detected feeding fluid amount.

18. The method according to claim 1, further comprising:
detecting, with an infrared sensor, a feeding fluid amount present in the chamber; and
signaling the entrance of additional feeding fluid into the chamber based on the detected feeding fluid amount.

19. The method according to claim 12, further comprising:
displaying, on a graphical user interface of a screen of a mobile computing device, a representation of the amount of feeding fluid that is consumed by the individual.

20. The method according to claim 19, wherein the representation comprises the amount of feeding fluid consumed by the individual during one feeding session.

21. The method according to claim 19, wherein the representation comprises the amount of feeding fluid consumed by the individual during multiple feeding sessions.

22. The method according to claim 12, further comprising engaging a breast flange with a breast of a nursing mother, wherein the breast flange is in fluid communication with the chamber and defines a breast flange axis, the feeding apparatus defines a feeding apparatus axis, and the breast flange axis is either in-line with or superior to the feeding apparatus axis.

23. The method according to claim 12, further comprising engaging a breast flange with a breast of a nursing mother, wherein the breast flange is in fluid communication with the chamber, the dosing mechanism comprises a peristaltic wheel, and a center of the peristaltic wheel is positioned posterior to an anterior portion of the breast flange and anterior to a posterior portion of the breast flange.

24. The method according to claim 12, further comprising engaging a breast flange with a breast of a nursing mother, wherein the chamber is positioned within a housing, and the feeding apparatus is attached with the housing and positioned inferior to the breast flange.

25. The method according to claim 24, wherein the feeding apparatus is removable from the housing.

26. The method according to claim 12, wherein the dosing mechanism comprises a peristaltic pump having a peristaltic tubing, and at least a portion of the tubing is positioned inferior to the nipple interior of the feeding apparatus.

* * * * *